United States Patent
Tessari et al.

(10) Patent No.: US 11,464,830 B2
(45) Date of Patent: Oct. 11, 2022

(54) TREATMENT OF INFLAMMATORY CONDITIONS BY DELIVERY OF INTERLEUKIN-1 RECEPTOR ANTAGONIST FUSION PROTEIN

(71) Applicant: Regeneron Pharmaceuticals, Inc., Tarrytown, NY (US)

(72) Inventors: Eben Tessari, Lexington, MA (US); John Paolini, Lexington, MA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 17/527,956

(22) Filed: Nov. 16, 2021

(65) Prior Publication Data
US 2022/0072102 A1 Mar. 10, 2022

Related U.S. Application Data

(62) Division of application No. 17/208,409, filed on Mar. 22, 2021, which is a division of application No. 16/143,391, filed on Sep. 26, 2018, now Pat. No. 11,026,997.

(60) Provisional application No. 62/563,387, filed on Sep. 26, 2017, provisional application No. 62/616,819, filed on Jan. 12, 2018, provisional application No. 62/625,075, filed on Feb. 1, 2018, provisional application No. 62/639,425, filed on Mar. 6, 2018, provisional application No. 62/654,291, filed on Apr. 6, 2018, provisional application No. 62/691,552, filed on Jun. 28, 2018, provisional application No. 62/716,331, filed on Aug. 8, 2018.

(51) Int. Cl.
| | |
|---|---|
| A61K 38/20 | (2006.01) |
| A61K 47/68 | (2017.01) |
| A61K 38/17 | (2006.01) |
| A61P 9/00 | (2006.01) |
| A61K 39/395 | (2006.01) |

(52) U.S. Cl.
CPC ...... *A61K 38/2006* (2013.01); *A61K 38/1709* (2013.01); *A61K 38/1793* (2013.01); *A61K 39/395* (2013.01); *A61K 47/68* (2017.08); *A61K 47/6811* (2017.08); *A61K 47/6813* (2017.08); *A61P 9/00* (2018.01)

(58) Field of Classification Search
CPC .... A61K 38/2006; A61K 47/6813; A61P 9/00
See application file for complete search history.

(56) References Cited

U.S. PATENT DOCUMENTS

2006/0171948 A1   8/2006   Weinstein et al.

FOREIGN PATENT DOCUMENTS

WO   WO 2012/078101 A1   6/2012

OTHER PUBLICATIONS

Anonymous, "Clinical Trial: RHAPSODY Phase 3 Study to Assess the Efficacy and Safety of Rilonacept Treatment in Subjects With Recurrent Pericarditis", Nov. 9, 2018 (Nov. 9, 2018), Retrieved from the Internet: URL:https://clinicaltrials.gov/ct2/Show/NCT03737110.
Anonymous, "Utilisation des anti-IL1 dans la PR", Dec. 1, 2012 (Dec. 1, 2012), XP055525909, Retrieved from the Internet <URL:http://www.cri-net.com/ckfinder/userfiles/files/fiches-pratiques/antiIL1/F15A_ANTI-IL1.pdf> [retrieved on Nov. 22, 2018].
Arend, William P., "Interleukin 1 Receptor Antagonist—A New Member of the Interleukin 1 Family" Perspectives—Interleukin 1 Receptor Antagonist, J. Clin. Invest. © The American Society for Clinical Investigation, Inc. vol. 88, Nov. 1991, 1445-1451.
Baskar, Shankar et al., "The Use of IL-1 Receptor Antagonist (Anakinra) in Idiopathic Recurrent Pericarditis: A Narrative Review" Hindawi Publishing Corporation, Cardiology Research and Practice, vol. 2016, Article ID 7840724, 6 pages.
Brucato et al., "Effect of Anakinra on Recurrent Pericarditis Among Patients With Colchicine Resistance and Corticosteroid Dependence : The AIRTRIP Randomized Clinical Trial", JAMA the Journal of the American Medical Association, vol. 316, No. 18, Nov. 8, 2016 (Nov. 8, 2016), p. 1906.
Buckley, Leo F., et al. "Interleukin-1 blockade for the treatment of pericarditis" European Society of Cardiology, European Heart Journal—Cardiovascular Pharmacotherapy (2018) 4, 46-53.
Calabuig et al., "Recurrent Pericarditis as the Presenting Form of Adult Still's Disease", Revista Espanola De Cardiologia, vol. 70, No. 3, Mar. 1, 2017 (Mar. 1, 2017), p. 208-209.
Chang et al., "Dual biological functions of an interleukin-1 receptor antagonist-interleukin-10 fusion protein and its suppressive effects on joint inflammation", Immunology, vol. 112, No. 4, Aug. 1, 2004 (Aug. 1, 2004), p. 643-650.
Dauphin, Claire et al. "Recurrent pericarditis: current challenges and future prospects" Research Reports in Clinical Cardiology Jul. 18, 2016:7 99-108.
International Search Report and Written Opinion for PCT/US18/52985, dated Feb. 27, 2019.

(Continued)

*Primary Examiner* — Ruixiang Li
(74) *Attorney, Agent, or Firm* — Proskauer Rose LLP; Fangli Chen

(57) ABSTRACT

The present invention provides, among other things, methods of treating post-cardiac injury syndrome (PCIS) or pericarditis, comprising a step of administering to a subject in need of treatment an interleukin-1 receptor-Fc fusion protein at a therapeutically effective dose and an administration interval for a treatment period sufficient to improve, stabilize or reduce one or more signs and symptoms of pericarditis relative to a control.

16 Claims, 20 Drawing Sheets

Specification includes a Sequence Listing.

(56) References Cited

OTHER PUBLICATIONS

Jaworska-Wilczynska et al., "Post-cardiac injury syndrome", Polish Journal of Cardio-Thoracic Surgery, vol. 1, Jan. 1, 2013 (Jan. 1, 2013), p. 20-26.
Kontzias, "Anakinra: A Promising Therapy For Refractory Idiopathic Recurrent Pericarditis", Dec. 9, 2015 (Dec. 9, 2015), Retrieved from the Internet: URL:https://www.acc.org/latest-in-cardiology/articles/2015/12/09/12/19/anakinra-a-promising-therapy-for-refractory-idiopathic-recurrent-pericarditis.
Lachmann, Helen J. et al., "In vivo regulation of interleukin 1β in patients with cryopyrin-associated periodic syndromes" The Journal of Experimental Medicine, Med. vol. 206 No. 5 1029-1036.
Lazaros et al., "The Therapeutic Role of Interleukin-1 Inhibition in Idiopathic Recurrent Pericarditis: Current Evidence and Future Challenges", Frontiers in Medicine, vol. 4, Jun. 12, 2017 (Jun. 12, 2017).
Prescribing Information for Arcalyst (Rilonacept).
Prescribing Information for Kineret (Anakinra).
Soler-Soler, Jordi et al., "General Cardiology—Relapsing Pericarditis" Heart 2004; 90:1364-1368.
Theodoropoulou, K., et al., "A case of corticosteroid-dependent recurrent pericarditis with different response to two IL-1 blocking agents," Pediatric Rheumatology 2015 13(Suppl 1):P155.
Van Tassell et al., "Targeting Interleukin-1 in Heart Disease", Circulation,vol. 128, No. 17, Oct. 22, 2013 (Oct. 22, 2013), p. 1910-1923.

| Subject | Parameter | SCV1 | SCV2 | Week 1 Day 0 | Day 3 Day 3 (+/-1) | Week 2 Day 7 (+/-1) | Week 3 Day 14 (+/-1) | Week 4 Day 21 (+/-1) | Week 5 Day 28 (+/-1) | Week 6 Day 35 (+/-1) | Week 7 Day 42 (+/-6) | Week 10 Day 63 (+/-1) | Week 14 Day 91 (+/-1) | Week 18 Day 119 (+/-1) | Week 22 Day 147 (+/-1) | Week 25 Day 168 (+/-1) |
|---|---|---|---|---|---|---|---|---|---|---|---|---|---|---|---|---|
| | Visit Day Visit Window | | | | | | | | | | | | | | | |
| Group 1, Subject A | Pain NRS Score | NR* | NR* | 6 | NR | 1 | 1 | 0 | 0 | 0 | 0 | 0 | 0 | 0 | 0 | 0 |
| | CRP (mg/dL) | NR* | NR* | 8.85 | | 0.66 | 0.6 | 0.25 | 0.11 | 0.08 | 0.1 | 0.05 | 0.07 | 0.09 | 0.07 | 0.09 |
| | Presence of Effusion | NR* | NR* | Yes | | | | | | | No | | | No | | No |
| | ECG Changes | NR* | NR* | PR depression | | | | | | | Normal | | | Normal | | Normal |
| | QoL Total | 31 | | 31 | | | | | | | 42 | | | 34 | | 36 |
| Group 1, Subject C | Pain NRS Score | 6 | 6 | 5 | NR | 0 | 2 | 1 | 1 | 0 | 0 | 0 | 0 | 0 | 0 | 0 |
| | CRP (mg/dL) | 6.71 | 4.14 | 4.68 | | 0.22 | 0.2 | 0.5 | 0.14 | 1.63 | 0.06 | 0.05 | NA* | 0.1 | 0.11 | 0.13 |
| | Presence of Effusion | Yes | NR* | Yes | | | | Yes | | | No | | | No | | NA |
| | ECG Changes | Normal | Normal | Normal | | | | Normal | | | Normal | | | Normal | | NA |
| | QoL Total | 23 | | 25 | | | | 29 | | | 32 | | | 27 | | 29 |
| Group 1, Subject B | Pain NRS Score | 3 | NR* | 3 | 2 | 2 | 0 | 0 | 0 | 0 | 0 | 0 | 0 | 0 | 0 | |
| | CRP (mg/dL) | 1.05 | NR* | 1.06 | | 0.8 | 0.57 | 0.46 | 0.57 | 0.63 | 0.51 | 0.55 | 0.38 | 0.7 | 0.82 | Not recorded yet |
| | Presence of Effusion | No | NR* | No | | | | | | | No | | | | | |
| | ECG Changes | Normal | NR* | Normal | | | | | | | Normal | | | | | |
| | QoL Total | 42 | | 43 | | | | | | | 43 | | | | | |
| Group 1, Subject D | Pain NRS Score | 2 | NR* | 3 | 6 | | 1 | 1 | 1 | 1 | 1 (same as Wed. 6) | | 4 | 0 | 0 | |
| | CRP (mg/dL) | 2.73 | NR* | 2.73 | | NA* | 0.35 | 0.27 | 0.24 | 0.28 | 0.28 | 0.26 | 0.17 | 0.13 | | Not recorded yet |

FIGURE 5

| Subject | Parameter | SCV1 | SCV2 | Week 1 Day 0 | Day 3 (+/-1) | Week 2 Day 7 (+/-1) | Week 3 Day 14 (+/-1) | Week 4 Day 21 (+/-1) | Week 5 Day 28 (+/-1) | Week 6 Day 35 (+/-1) | Week 7 Day 42 (+/-6) | Week 10 Day 63 (+/-1) | Week 14 Day 91 (+/-1) | Week 18 Day 119 (+/-1) | Week 22 Day 147 (+/-1) | Week 25 Day 168 (+/-1) |
|---|---|---|---|---|---|---|---|---|---|---|---|---|---|---|---|---|
| | Visit Day Visit Window | | | | | | | | | | | | | | | |
| | Presence of Effusion | No | NR* | No | | | | | | | NA | | | | | |
| | ECG Changes | Normal | NR* | Normal | | | | | | | NA | | | | | |
| | QoL Total | 27 | | 27 | | | | | | | 29 | | | | | |
| Group 1, Subject E | Pain NRS Score | NR* | NR* | 3 | 0 | 0 | 0 | 0 | 0 | 0 | 1 | 0 | 0 | | | |
| | CRP (mg/dL) | NR* | NR* | 0.77† | | 0.12 | 0.15 | 0.11 | 0.13 | 0.09 | 0.12 | 0.09 | 0.1 | | | |
| | Presence of Effusion | NR* | NR* | No | | | | | | | No | | | Not recorded yet | Not recorded yet | Not recorded yet |
| | ECG Changes | NR* | NR* | PR depression | | | | | | | PR depression (*normal) | | | | | |
| | QoL Total | NR* | NR* | 35 | | | | | | | 33 | | | | | |
| Group 1, Subject F | Pain NRS Score | 6 | NR* | 5 | 3 | 4 | 6 | 3 | 2 | 5 | 4 | 2 | 2 | | | |
| | CRP (mg/dL) | 2.56 | NR* | 1.56 | | 0.19 | 0.62 | 0.33 | 0.21 | 0.69 | 0.42 | 0.28 | 0.55 | | | |
| | Presence of Effusion | Yes | NR* | Yes | | | | | | | No | | | Not recorded yet | Not recorded yet | Not recorded yet |
| | ECG Changes | ST elevation | NR* | ST elevation | | | | | | | Normal | | | | | |
| | QoL Total | 12 | | 12 | | | | | | | 19 | | | | | |
| Group 1, Subject G | Pain NRS Score | 2 | NR* | 6 | 8 | 3 | 3 | 0 | 1 | 0 | 0 | 0 | Not recorded yet | Not recorded yet | Not recorded yet | Not recorded yet |
| | CRP (mg/dL) | 0.97 | NR* | 1.22 | | 0.44 | 0.18 | 0.24 | 0.33 | 0.26 | 0.26 | 0.25 | | | | |

FIGURE 5 (Continued)

| Subject | Parameter | SCV1 | SCV2 | Week 1 Day 0 | Day 3 Day 3 (+/-1) | Week 2 Day 7 (+/-1) | Week 3 Day 14 (+/-1) | Week 4 Day 21 (+/-1) | Week 5 Day 28 (+/-1) | Week 6 Day 35 (+/-1) | Week 7 Day 42 (+/-6) | Week 10 Day 63 (+/-1) | Week 14 Day 91 (+/-1) | Week 18 Day 119 (+/-1) | Week 22 Day 147 (+/-1) | Week 25 Day 168 (+/-1) |
|---|---|---|---|---|---|---|---|---|---|---|---|---|---|---|---|---|
| | Visit Day Visit Window | | | | | | | | | | | | | | | |
| Group 1, Subject H | Presence of Effusion | No | NR* | No | | | | NA | | No | No | | | | | |
| | ECG Changes | Normal | NR* | Normal | | | | Normal | | Normal | Normal | | | | | |
| | QoL Total | 29 | 8 | 36 | | | | 38 | | 42 | 42 | | | | | |
| | Pain NRS Score | 8 | 8 | 8 | 4 | 3 | 2 | 2 | | | | | | | | |
| | CRP (mg/dL) | 9.12 | NR* | 19.84 | | 0.67 | 0.08 | 0.04 | | | | | | | | |
| | Presence of Effusion | NA | NR* | NA | | | | No | | | | | | | | |
| | ECG Changes | Normal | NR* | ST elevatio n | | | | Normal | | | | | | | | |
| Group 1, Subject I | QoL Total | 21 | NR* | 19 | 0 | | | 21 | | | | | | | | |
| | Pain NRS Score | 4 | NR* | 5 | | Not recorded yet | Not recorded yet | Not recorded yet | Not recorded yet | Not recorded yet | Not recorded yet | Not recorded yet | Not recorded yet | | | |
| | CRP (mg/dL) | NA | NR* | NA | | | | | | | | | | | | |
| | Presence of Effusion | NA | NR* | NA | | | | | | | | | | | | |
| | ECG Changes | NA | NR* | NA | | | | | | | | | | | | |
| Group 2, Subject A | QoL Total | NA | NR* | NA | | | | | | | | | | | | |
| | Pain NRS Score | 4 | NR* | 4 | 4 | 1 | 3 | 2 | 1 | 0 | 0 | 0 | 0 | Not recorded yet | Not recorded yet | Not recorded yet |
| | CRP (mg/dL) | 0.34 | NR* | 0.30†† | | 0.14 | 0.26 | 0.25 | 0.31 | 0.58 | 0.55 | 0.58 | 0.5 | Not recorded yet | Not recorded yet | Not recorded yet |
| | Presence of Effusion | No | NR* | No | | | | No | | | No | | No | Not recorded yet | Not recorded yet | Not recorded yet |
| | ECG Changes | Normal | NR* | Normal | | | | Normal | | | Normal | | NA | Not recorded yet | Not recorded yet | Not recorded yet |

FIGURE 5 (Continued)

| Subject | Parameter | SCV1 | SCV2 | Week 1 Day 0 | Day 3 Day 3 (+/-1) | Week 2 Day 7 (+/-1) | Week 3 Day 14 (+/-1) | Week 4 Day 21 (+/-1) | Week 5 Day 28 (+/-1) | Week 6 Day 35 (+/-3) | Week 7 Day 42 (+/-6) | Week 10 Day 63 (+/-1) | Week 14 Day 91 (+/-1) | Week 18 Day 119 (+/-1) | Week 22 Day 147 (+/-1) | Week 25 Day 168 (+/-1) |
|---|---|---|---|---|---|---|---|---|---|---|---|---|---|---|---|---|
| | Visit Day | | | | | | | | | | | | | | | |
| | Visit Window | | | | | | | | | | | | | | | |
| Group 2, Subject B | QoL Total | 26 | | 26 | | | | 40 | | | 40 | | 38 | | | |
| | Pain NRS Score | NR* | NR* | 2 | 2 | 1 | 1 | 1 | 0 | 0 | 0 | | | | | |
| | CRP (mg/dL) | NR* | NR* | 0.09 | | 0.02 | 0.04 | 0.03 | 0.06 | 0.03 | 0.05 | | | | | |
| | Presence of Effusion | NR* | NR* | No | | | | | | | No | Not recorded yet | Not recorded yet | Not recorded yet | Not recorded yet | Not recorded yet |
| | ECG Changes | NR* | NR* | Normal | | | | | | | Normal | | | | | |
| | QoL Total | NR* | NR* | 33 | | | | | | | 37 | | | | | |
| Group 3, Subject A | Pain NRS Score | NR* | NR* | 2 | 3 | 4 | 2 | 2 | 1 | 2 | 2 | | | | | |
| | CRP (mg/dL) | NR* | NR* | 0.17 | | 0.06 | 0.16 | 0.07 | 0.06 | 0.06 | 0.06 | | | | | |
| | Presence of Effusion | NR* | NR* | Yes | | | | | | | No | | | | | |
| | ECG Changes | NR* | NR* | Normal | | | | | | | Normal | | | | | |
| | QoL Total | NR* | NR* | 21 | | | | | | | 31 | | | | | |
| Group 3, Subject B | Pain NRS Score | NR* | NR* | 1 | 2 | 4 | 4 | 3 | 2 | 0 | 1 | 0 | 0 | NA | | |
| | CRP (mg/dL) | NR* | NR* | 0.34 | | 0.16 | 0.11 | 0.11 | 0.13 | 0.08 | 0.10 | 0.08 | 0.12 | 0.06 | | |
| | Presence of Effusion | NR* | NR* | No | | | | | | | No | | | | | |
| | ECG Changes | NR* | NR* | Normal | | | | | | | Abnorm al NCS | | | | | |
| | QoL Total | NR* | NR* | 19 | | | | | | | 27 | | | | | |
| Group 3, Subject C | Pain NRS Score | NR* | NR* | 0 | 0 | 0 | 0 | 0 | 0 | 0 | 0 | NA | 0 | NA | Not recorded yet | Not recorded yet |
| | CRP (mg/dL) | NR* | NR* | 0.16 | | 0.08 | 0.07 | 0.1 | 0.07 | 0.27 | 0.12 | 0.06 | 0.12 | 0.06 | | |

FIGURE 5 (Continued)

| | Parameter | SCV1 | SCV2 | Week 1<br>Day 0 | Day 3<br>Day 3<br>(+/-1) | Week 2<br>Day 7<br>(+/-1) | Week 3<br>Day 14<br>(+/-1) | Week 4<br>Day 21<br>(+/-1) | Week 5<br>Day 28<br>(+/-1) | Week 6<br>Day 35<br>(+/-1) | Week 7<br>Day 42<br>(+/-6) | Week 10<br>Day 63<br>(+/-1) | Week 14<br>Day 91<br>(+/-1) | Week 18<br>Day 119<br>(+/-1) | Week 22<br>Day 147<br>(+/-1) | Week 25<br>Day 168<br>(+/-1) |
|---|---|---|---|---|---|---|---|---|---|---|---|---|---|---|---|---|
| | Visit Day | | | | | | | | | | | | | | | |
| | Visit Window | | | | | | | | | | | | | | | |
| Subject | Presence of Effusion | NR* | NR* | No | | | | | | | No | | | | | |
| | ECG Changes | NR* | NR* | Abnormal NCS | | | | | | | Normal | | | | | |
| | QoL Total | 39 | | 39 | | | | | | | 37 | | | | | |

■ =Not Required per protocol
■ =Not Participating in Extension
NA=Collected, Not Available at time of data cut-off (19 September 2018)
NA*=Subject lab sample was not processed due to unexpected circumstances
NR=Not Required as per protocol prior to protocol amendment 2.0
NR*=Not Required as screening visits were combined with Day 0 as allowed per protocol
†=The local lab value drawn during the screening visit for subject qualification was 1.5 mg/dL. This value was drawn on the same day as the central lave value referenced in the table.
††=This is the local lab value. The central lab value drawn during the screening visit was 7.36 mg/dL. This value was drawn on the same day as the local lab value referenced in the table.

FIGURE 5 (Continued)

SEQUENCE LISTING

```
<160> NUMBER OF SEQ ID NOS: 5

<210> SEQ ID NO 1
<211> LENGTH: 880
<212> TYPE: PRT
<213> ORGANISM: Artificial Sequence
<220> FEATURE:
<223> OTHER INFORMATION: Synthetic Polypeptide

<400> SEQUENCE: 1
```

```
Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
                35                  40                  45

Ile Trp Tyr Trp Thr Arg Gln Asp Arg Asp Leu Glu Glu Pro Ile Asn
50                      55                  60

Phe Arg Leu Pro Glu Asn Arg Ile Ser Lys Glu Lys Asp Val Leu Trp
65                          70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
            115                 120                 125

Leu Tyr Ile Glu Tyr Gly Ile Gln Arg Ile Thr Cys Pro Asn Val Asp
        130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
            195                 200                 205

Leu Thr Val Lys Val Val Gly Ser Pro Lys Asn Ala Val Pro Pro Val
210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
            290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu Lys Cys Lys Glu Arg Glu Lys Ile Ile Leu Val Ser
                340                 345                 350

Ser Ala Asn Glu Ile Asp Val Arg Pro Cys Pro Leu Asn Pro Asn Glu
            355                 360                 365

His Lys Gly Thr Ile Thr Trp Tyr Lys Asp Asp Ser Lys Thr Pro Val
            370                 375                 380

Ser Thr Glu Gln Ala Ser Arg Ile His Gln His Lys Glu Lys Leu Trp
385                 390                 395                 400

Phe Val Pro Ala Lys Val Glu Asp Ser Gly His Tyr Tyr Cys Val Val
            405                 410                 415

Arg Asn Ser Ser Tyr Cys Leu Arg Ile Lys Ile Ser Ala Lys Phe Val
```

```
            420                425                430
Glu Asn Glu Pro Asn Leu Cys Tyr Asn Ala Gln Ala Ile Phe Lys Gln
            435                440                445
Lys Leu Pro Val Ala Gly Asp Gly Leu Val Cys Pro Tyr Met Glu
    450                455                460
Phe Phe Lys Asn Glu Asn Glu Leu Pro Lys Leu Gln Trp Tyr Lys
465                470                475                480
Asp Cys Lys Pro Leu Leu Leu Asp Asn Ile His Phe Ser Gly Val Lys
                485                490                495
Asp Arg Leu Ile Val Met Asn Val Ala Glu Lys His Arg Gly Asn Tyr
            500                505                510
Thr Cys His Ala Ser Tyr Thr Tyr Leu Gly Lys Gln Tyr Pro Ile Thr
        515                520                525
Arg Val Ile Glu Phe Ile Thr Leu Glu Glu Asn Lys Pro Thr Arg Pro
        530                535                540
Val Ile Val Ser Pro Ala Asn Glu Thr Met Glu Val Asp Leu Gly Ser
545                550                555                560
Gln Ile Gln Leu Ile Cys Asn Val Thr Gly Gln Leu Ser Asp Ile Ala
                565                570                575
Tyr Trp Lys Trp Asn Gly Ser Val Ile Asp Glu Asp Asp Pro Val Leu
                580                585                590
Gly Glu Asp Tyr Tyr Ser Val Glu Asn Pro Ala Asn Lys Arg Arg Ser
        595                600                605
Thr Leu Ile Thr Val Leu Asn Ile Ser Glu Ile Glu Ser Arg Phe Tyr
        610                615                620
Lys His Pro Phe Thr Cys Phe Ala Lys Asn Thr His Gly Ile Asp Ala
625                630                635                640
Ala Tyr Ile Gln Leu Ile Tyr Pro Val Thr Asn Ser Gly Asp Lys Thr
                645                650                655
His Thr Cys Pro Pro Cys Pro Ala Pro Glu Leu Leu Gly Gly Pro Ser
            660                665                670
Val Phe Leu Phe Pro Pro Lys Pro Lys Asp Thr Leu Met Ile Ser Arg
        675                680                685
Thr Pro Glu Val Thr Cys Val Val Val Asp Val Ser His Glu Asp Pro
        690                695                700
Glu Val Lys Phe Asn Trp Tyr Val Asp Gly Val Glu Val His Asn Ala
705                710                715                720
Lys Thr Lys Pro Arg Glu Glu Gln Tyr Asn Ser Thr Tyr Arg Val Val
                725                730                735
Ser Val Leu Thr Val Leu His Gln Asp Trp Leu Asn Gly Lys Glu Tyr
            740                745                750
Lys Cys Lys Val Ser Asn Lys Ala Leu Pro Ala Pro Ile Glu Lys Thr
        755                760                765
Ile Ser Lys Ala Lys Gly Gln Pro Arg Glu Pro Gln Val Tyr Thr Leu
        770                775                780
Pro Pro Ser Arg Asp Glu Leu Thr Lys Asn Gln Val Ser Leu Thr Cys
785                790                795                800
Leu Val Lys Gly Phe Tyr Pro Ser Asp Ile Ala Val Glu Trp Glu Ser
                805                810                815
Asn Gly Gln Pro Glu Asn Asn Tyr Lys Thr Thr Pro Val Leu Asp
            820                825                830
Ser Asp Gly Ser Phe Phe Leu Tyr Ser Lys Leu Thr Val Asp Lys Ser
            835                840                845
```

```
Arg Trp Gln Gln Gly Asn Val Phe Ser Cys Ser Val Met His Glu Ala
    850                 855                 860

Leu His Asn His Tyr Thr Gln Lys Ser Leu Ser Leu Ser Pro Gly Lys
865                 870                 875                 880

<210> SEQ ID NO 2
<211> LENGTH: 900
<212> TYPE: PRT
<213> ORGANISM: Artificial Sequence
<220> FEATURE:
<223> OTHER INFORMATION: Synthetic Polypeptide

<400> SEQUENCE: 2

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335
```

```
Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
            355                 360                 365

Ile Leu Val Ser Ser Ala Asn Glu Ile Asp Val Arg Pro Cys Pro Leu
370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
            435                 440                 445

Ala Lys Phe Val Glu Asn Glu Pro Asn Leu Cys Tyr Asn Ala Gln Ala
        450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
            515                 520                 525

Arg Gly Asn Tyr Thr Cys His Ala Ser Tyr Thr Tyr Leu Gly Lys Gln
        530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
        610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Asp Lys Thr His Thr Cys Pro Pro Cys Pro Ala Pro Glu Leu Leu
            675                 680                 685

Gly Gly Pro Ser Val Phe Leu Phe Pro Pro Lys Pro Lys Asp Thr Leu
        690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750
```

```
Tyr Arg Val Val Ser Val Leu Thr Val Leu His Gln Asp Trp Leu Asn
            755                 760                 765

Gly Lys Glu Tyr Lys Cys Lys Val Ser Asn Lys Ala Leu Pro Ala Pro
770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
835                 840                 845

Pro Val Leu Asp Ser Asp Gly Ser Phe Phe Leu Tyr Ser Lys Leu Thr
        850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900

<210> SEQ ID NO 3
<211> LENGTH: 339
<212> TYPE: PRT
<213> ORGANISM: Artificial Sequence
<220> FEATURE:
<223> OTHER INFORMATION: Synthetic Polypeptide

<400> SEQUENCE: 3

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
            85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
            165                 170                 175

Leu Ser Phe Leu Ile Ala Leu Ile Ser Asn Asn Gly Asn Tyr Thr Cys
        180                 185                 190

Val Val Thr Tyr Pro Glu Asn Gly Arg Thr Phe His Leu Thr Arg Thr
    195                 200                 205
```

-continued

```
Leu Thr Val Lys Val Val Gly Ser Pro Lys Asn Ala Val Pro Val
210                 215                 220
Ile His Ser Pro Asn Asp His Val Val Tyr Glu Lys Glu Pro Gly Glu
225                 230                 235                 240
Glu Leu Leu Ile Pro Cys Thr Val Tyr Phe Ser Phe Leu Met Asp Ser
                245                 250                 255
Arg Asn Glu Val Trp Trp Thr Ile Asp Gly Lys Lys Pro Asp Asp Ile
                260                 265                 270
Thr Ile Asp Val Thr Ile Asn Glu Ser Ile Ser His Ser Arg Thr Glu
                275                 280                 285
Asp Glu Thr Arg Thr Gln Ile Leu Ser Ile Lys Lys Val Thr Ser Glu
290                 295                 300
Asp Leu Lys Arg Ser Tyr Val Cys His Ala Arg Ser Ala Lys Gly Glu
305                 310                 315                 320
Val Ala Lys Ala Ala Lys Val Lys Gln Lys Val Pro Ala Pro Arg Tyr
                325                 330                 335
Thr Val Glu

<210> SEQ ID NO 4
<211> LENGTH: 312
<212> TYPE: PRT
<213> ORGANISM: Artificial Sequence
<220> FEATURE:
<223> OTHER INFORMATION: Synthetic Polypeptide

<400> SEQUENCE: 4

Lys Cys Lys Glu Arg Glu Lys Ile Ile Leu Val Ser Ser Ala Asn
1               5                   10                  15
Glu Ile Asp Val Arg Pro Cys Pro Leu Asn Pro Asn Glu His Lys Gly
                20                  25                  30
Thr Ile Thr Trp Tyr Lys Asp Asp Ser Lys Thr Pro Val Ser Thr Glu
            35                  40                  45
Gln Ala Ser Arg Ile His Gln His Lys Glu Lys Leu Trp Phe Val Pro
    50                  55                  60
Ala Lys Val Glu Asp Ser Gly His Tyr Tyr Cys Val Val Arg Asn Ser
65                  70                  75                  80
Ser Tyr Cys Leu Arg Ile Lys Ile Ser Ala Lys Phe Val Glu Asn Glu
                85                  90                  95
Pro Asn Leu Cys Tyr Asn Ala Gln Ala Ile Phe Lys Gln Lys Leu Pro
                100                 105                 110
Val Ala Gly Asp Gly Gly Leu Val Cys Pro Tyr Met Glu Phe Phe Lys
            115                 120                 125
Asn Glu Asn Asn Glu Leu Pro Lys Leu Gln Trp Tyr Lys Asp Cys Lys
130                 135                 140
Pro Leu Leu Leu Asp Asn Ile His Phe Ser Gly Val Lys Asp Arg Leu
145                 150                 155                 160
Ile Val Met Asn Val Ala Glu Lys His Arg Gly Asn Tyr Thr Cys His
                165                 170                 175
Ala Ser Tyr Thr Tyr Leu Gly Lys Gln Tyr Pro Ile Thr Arg Val Ile
                180                 185                 190
Glu Phe Ile Thr Leu Glu Glu Asn Lys Pro Thr Arg Pro Val Ile Val
            195                 200                 205
Ser Pro Ala Asn Glu Thr Met Glu Val Asp Leu Gly Ser Gln Ile Gln
210                 215                 220
Leu Ile Cys Asn Val Thr Gly Gln Leu Ser Asp Ile Ala Tyr Trp Lys
```

```
            225                 230                 235                 240

Trp Asn Gly Ser Val Ile Asp Glu Asp Pro Val Leu Gly Glu Asp
                245                 250                 255

Tyr Tyr Ser Val Glu Asn Pro Ala Asn Lys Arg Arg Ser Thr Leu Ile
                260                 265                 270

Thr Val Leu Asn Ile Ser Glu Ile Glu Ser Arg Phe Tyr Lys His Pro
                275                 280                 285

Phe Thr Cys Phe Ala Lys Asn Thr His Gly Ile Asp Ala Ala Tyr Ile
                290                 295                 300

Gln Leu Ile Tyr Pro Val Thr Asn
305                 310

<210> SEQ ID NO 5
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly Lys
225
```

TREATMENT OF INFLAMMATORY CONDITIONS BY DELIVERY OF INTERLEUKIN-1 RECEPTOR ANTAGONIST FUSION PROTEIN

RELATED APPLICATIONS

This application is a Divisional Application of U.S. application Ser. No. 17/208,409, filed Mar. 22, 2021, which is a Divisional Application of U.S. application Ser. No. 16/143,391, filed Sep. 26, 2018, issued as U.S. Pat. No. 11,026,997, which claims priority to U.S. Provisional Applications Ser. No. 62/563,387, filed on Sep. 26, 2017; Ser. No. 62/616,819, filed on Jan. 12, 2018; Ser. No. 62/625,075, filed on Feb. 1, 2018; Ser. No. 62/639,425, filed on Mar. 6, 2018; Ser. No. 62/654,291, filed on Apr. 6, 2018; Ser. No. 62/691,552, filed on Jun. 28, 2018; and Ser. No. 62/716,331, filed on Aug. 8, 2018, the disclosures of all of which are hereby incorporated by reference.

SEQUENCE LISTING

The present specification makes reference to a Sequence Listing (submitted electronically as a .txt file named "KPL-010US3_ST5" on Nov. 15, 2021). The .txt file was generated on Nov. 14, 2021 and is bytes 24 KB in size. The entire contents of the Sequence Listing are hereby incorporated by reference.

BACKGROUND

IL-1α and IL-1β provoke potent, pro-inflammatory events by engaging the IL-1α and IL-1β receptor. Following tissue insult, the release of IL-1α acts as the primary initiating signal to coordinate the mobilization of immune cells to the damaged area, while IL-1β is secreted mostly by macrophages and is a prototypical cytokine of the canonical inflammasome. IL-1α and IL-1β signaling results in a dramatic increase in the production of cytokines that orchestrate the proliferation and recruitment of phagocytes to the site of damage, resulting in inflammation. Moreover, IL-1α and IL-1β signaling also affect other immune-system cells, such as T-cells and B-cells.

IL-1β's role in the inflammation process has been extensively studied, while in comparison, much is still unknown about the independent function of IL-1α in disease pathology. Despite driving similar immunological outcomes, IL-1α and IL-1β differ substantially in their expression and regulation, and non-redundant roles for IL-1α and IL-1β have been demonstrated in multiple inflammatory diseases. There are disease states in which IL-1β inhibition alone does not appear to be sufficient for disease remission in the absence of IL-1α inhibition. Published studies suggest certain autoinflammatory diseases may, in fact, be pathologically driven primarily by IL-1α.

Post-cardiac injury syndrome (PCIS) is an aetiologic heterogeneous group of autoimmune-mediated conditions of pericardial, epicardial, and myocardial inflammation. Pericarditis is the inflammation of the pericardium, the thin, two-layered, fluid-filled, sac surrounding the heart. Pericarditis often causes chest pain and sometimes other symptoms. The sharp chest pain associated with pericarditis occurs when the irritated layers of the pericardium rub against each other. Signs and symptoms of pericarditis may include some or all of the following: sharp, piercing chest pain over the center or left side of the chest, which is generally more intense when breathing in or reclining; shortness of breath when reclining; heart palpitations; low-grade fever; an overall sense of weakness, fatigue or feeling sick; cough; and abdominal or leg swelling.

Currently available treatments for pericarditis include medications to reduce the inflammation and swelling associated with pericarditis. These medications include non-steroidal anti-inflammatory drugs, such as aspirin, ibuprofen or indomethacin; colchicine, which reduces inflammation; and corticosteroids, if a patient doesn't respond to pain relievers or colchicine or if a patient has current symptoms or pericarditis. Colchicine can reduce the duration of pericarditis symptoms and decrease the risk that the condition will recur, but the medication is not safe for patients with pre-existing health conditions like liver or kidney disease or for patients taking certain medications and may cause side effects, including nausea and diarrhea, that can lead to discontinuation of treatment. Steroids are known to cause significant side effects, particularly with long-term use. Patients with refractory symptoms can be particularly challenging to manage, and as a result, there is a significant and very long-standing need to identify new agents with favorable benefit to risk ratios that can be given systemically to treat pericarditis.

SUMMARY OF THE INVENTION

The present invention provides, among other things, methods of treating post-cardiac injury syndromes (PCISs) and pericarditis with an interleukin-1 receptor-Fc fusion protein. In particular, the present invention is based on the therapeutic efficacy observed in human pericarditis patients, especially patients with recurrent pericarditis, after administrating a recombinant IL-1 receptor/IL-1 accessory protein-Fc fusion protein (e.g., IL-1 receptor-Fc fusion protein). Without wishing to be bound by any theory, it is contemplated that the recombinant IL-1-Fc fusion protein used in the present invention acts as a soluble decoy receptor binding IL-1α/IL-1β and prevents their interaction with the IL-1 cell surface receptor. As demonstrated in the Examples below, administration of such a recombinant IL-1 receptor-Fc fusion protein resulted in clinically significant reduction of pericarditis associated inflammation and pain, and clinically significant improvement in cardiac pathology. Moreover, the use of a recombinant IL-1 receptor-Fc fusion protein according to the present invention resulted in positive safety and tolerability profile. Thus, the present invention addresses the unmet need in pericarditis treatment by providing a highly safe and efficacious drug for this disease.

In one aspect, the present invention provides a method of treating post-cardiac injury syndrome (PCIS) comprising a step of administering to a subject in need of treatment an interleukin-1 receptor-Fc fusion protein at a therapeutically effective dose and an administration interval for a treatment period sufficient to improve, stabilize or reduce one or more symptoms of PCIS relative to a control. In another aspect, the present invention provides methods of treating pericarditis, comprising a step of administering to a subject in need of treatment an interleukin-1 receptor-Fc fusion protein at a therapeutically effective dose and an administration interval for a treatment period sufficient to improve, stabilize or reduce one or more symptoms of pericarditis relative to a control. In one embodiment, the pericarditis is recurrent pericarditis. In another embodiment, the pericarditis is refractory pericarditis. In one embodiment, the pericarditis is idiopathic pericarditis. In one embodiment, the idiopathic pericarditis is recurrent idiopathic pericarditis. In another embodiment, the pericarditis is non-idiopathic pericarditis, including, for example, pericarditis associated with a PCIS. In some embodiments, the pericarditis is recurrent non-idiopathic pericarditis. In some embodiments, the idiopathic pericarditis is refractory idiopathic pericarditis. In some embodiments, the pericarditis is refractory non-idiopathic pericarditis.

In some embodiments, the PCIS is selected from myocardial infarction pericarditis, post-myocardial infarction pericarditis, post-pericardiotomy syndrome (PPS) or post-traumatic pericarditis. In certain embodiments, the post-myocardial infarction pericarditis is early post-myocardial infarct-associated pericarditis (pericarditis epistenocardica) or late post-myocardial infarction pericarditis (Dressler's Syndrome). In other embodiments, the post-traumatic pericarditis is non-iatrogenic trauma or iatrogenic trauma. In one embodiment, the idiopathic pericarditis is associated with Adult-Onset Still's Disease. In one embodiment, the pericarditis is recurrent, non-idiopathic pericarditis.

In some embodiments, the subject in need of treatment has recurrent pericarditis. In some embodiments, the subject in need of treatment has recurrent idiopathic pericarditis. In some embodiments, the subject in need of treatment has recurrent non-idiopathic pericarditis.

In one embodiment, the subject has refractory pericarditis. In one embodiment, the subject has refractory idiopathic or non-idiopathic pericarditis.

In one embodiment, the subject has post-cardiac injury syndrome (PCIS). In certain embodiments, the subject has post-myocardial infarction pericarditis, post-pericardiotomy syndrome (PPS) or post-traumatic pericarditis, early post-myocardial infarct-associated pericarditis (pericarditis epistenocardica) or late post-myocardial infarction pericarditis (Dressler's Syndrome). In other embodiments, the post-traumatic pericarditis is non-iatrogenic trauma or iatrogenic trauma. In one embodiment, the subject has pericarditis associated with Adult-Onset Still's Disease.

In one embodiment, the subject has pericarditis. In one embodiment, the subject has pericarditis as a symptom, or associated with PCSI. In one embodiment, the subject has recurrent or refractory pericarditis. In one embodiment, the subject has idiopathic pericarditis. In one embodiment, the subject has recurrent idiopathic pericarditis.

In one embodiment, the step of administering comprises subcutaneous administration. In one embodiment, the subcutaneous administration is through subcutaneous injection. In one embodiment, the step of administering comprises an initial loading dose, followed by at least one maintenance dose. In one embodiment, the initial loading dose is greater than the at least one maintenance dose. In one embodiment, the initial loading dose is twofold greater in dosage than the dosage of the at least one maintenance dose. In one embodiment, the initial loading dose is delivered as two injections of equal dosage. In one embodiment, the therapeutically effective dose comprises an initial loading dose or a maintenance dose. In one embodiment, the therapeutically effective dose is equal to or greater than 320 mg. In one embodiment, the therapeutically effective dose comprises an initial loading dose equal to or greater than 320 mg. In one embodiment, the initial loading dose is delivered as two injections of 160 mg. In one embodiment, the therapeutically effective dose is equal to or greater than 160 mg. In one embodiment, the therapeutically effective dose comprises a maintenance dose equal to or greater than 160 mg. In one embodiment, the therapeutically effective dose comprises an initial loading dose equal to or greater than 160 mg. In one embodiment, the initial loading dose is delivered as two injections of 80 mg. In one embodiment, the therapeutically effective dose is equal to or greater than 80 mg. In one embodiment, the therapeutically effective dose comprises a maintenance dose equal to or greater than 80 mg.

In one embodiment, the therapeutically effective dose is equal to or greater than 4 mg/kg. In one embodiment, the therapeutically effective dose comprises an initial loading dose equal to or greater than 4 mg/kg. In a particular embodiment, the initial loading dose is equal to or greater than 4.4 mg/kg. In some embodiments, the initial loading dose is delivered as a single injection. In some embodiments, the initial loading dose is delivered as two injections of 2.2 mg/kg. In one embodiment, the therapeutically effective dose is equal to or greater than 2 mg/kg. In another embodiment, the therapeutically effective dose comprises a maintenance dose equal to or greater than 2 mg/kg. In a particular embodiment, the maintenance dose is equal to or greater than 2.2 mg/kg.

In one embodiment, the therapeutically effective dose is delivered as a volume of less than or equal to 2 mL.

In one embodiment, the administration interval is once every week. In one embodiment, the administration interval is at least five days. In one embodiment, the administration interval is once every two weeks. In one embodiment, the administration interval is once every three weeks. In one embodiment, the administration interval is once every four weeks. In one embodiment, the administration interval is once every five weeks.

In one embodiment, the subject in need of treatment is 18 years of age or older. In a particular embodiment, the initial loading dose is delivered as two injections of 160 mg each and the maintenance dose is delivered 160 mg per week to a subject 18 years of age or older. In some embodiments, a subject is re-administered a loading dose of 320 mg. In some embodiments, a subject is administered double the quantity of loading dose of 320 mg. In some embodiments, a subject is administered about 720 mg of IL-1 receptor-Fc fusion protein.

In another embodiment, the subject in need of treatment is younger than 18 years of age. In one embodiment, the subject in need of treatment is 6 to <18 years of age. In a particular embodiment, the initial loading dose is delivered as two injections of 2.2 mg/kg each and the maintenance dose is delivered 2.2 mg/kg per week to a subject 6 to <18 years of age.

In one embodiment, the one or more symptoms of pericarditis are assessed by a Numerical Rating Scale (NRS) for assessment of pericarditis pain. In one embodiment, the one or more signs of pericarditis are assessed by an echocardiogram. In one embodiment, the one or more signs of pericarditis assessed by an echocardiogram comprise pericardial effusion. In one embodiment, the one or more signs of pericarditis are assessed by an electrocardiogram (ECG). In one embodiment, the one or more symptoms of pericarditis assessed by an ECG comprise widespread ST-elevation and/or PR depression. In one embodiment, the one or more signs of pericarditis comprise fever and/or pericardial rub. In one embodiment, the one or more signs of pericarditis are assessed by cardiac magnetic resonance imaging (MM). In one embodiment, the one or more symptoms of pericarditis are assessed by measuring blood levels of C-reactive protein (CRP). In one embodiment, measuring blood levels of CRP comprises measuring blood levels of CRP at several time points after an administering an initial loading dose of the interleukin-1 receptor-Fc fusion protein, wherein a linear regression is performed to determine the change of CRP levels from baseline, change of CRP levels from baseline adjusted for placebo effect and/or the slope of blood levels of CRP over time. In some embodiments, change of blood CRP level is not measured. In one embodiment, the one or more symptoms of pericarditis are assessed by a Quality of Life Questionnaire. In one embodiment, the administration of the interleukin-1 receptor-Fc fusion protein results in a statistically-significant drop on a Numerical Rating Scale (NRS) for assessment of pericarditis pain. In one embodiment, the control is indicative of the one or more symptoms of pericarditis in the subject before the treatment. In one embodiment, the one or more symptoms of pericarditis in the subject before the treatment comprise a CRP value greater than 1 mg/dL.

In one embodiment, the subject in need of treatment has had an index episode of pericarditis. As used herein, the term "index" is used interchangeably with "incident" and in each case represents the first incident of pericarditis in the subject. In one embodiment, the index episode of pericarditis met at least two criteria for an acute pericarditis event, wherein the criteria comprise pericarditic chest pain, pericardial rubs, new widespread ST-segment elevation or PR-segment depression on ECG, and new or worsening pericardial effusion. In one embodiment, the subject in need of treatment has had at least one recurrent episode of pericarditis. In one embodiment, the subject in need of treatment has an ongoing symptomatic episode of pericarditis. In one embodiment, the control is indicative of the one or more symptoms of pericarditis in a control subject with the same disease status without treatment. In one embodiment, the control is indicative of the one or more symptoms of pericarditis as determined by evaluating health information from pericarditis patients over time, demonstrating the natural progress of the condition, which can be obtained, for example, from a natural history study of pericarditis. In some embodiments, a control is indicative of the disease state when a subject having the disease receives a standard of care therapy, in absence of IL-1 receptor-Fc fusion protein administration.

In one embodiment, the administration results in no serious adverse events in the subject. In one embodiment, the administration results in serious adverse events that are acceptable in view of the specific treatment benefits. In one embodiment, the administration does not result in an adverse effect selected from the group consisting of injection-site reaction, upper respiratory tract infection, headache, nausea, vomiting, diarrhea, sinusitis, arthralgia, flu-like symptoms, abdominal pain, pyrexia, nasopharyngitis, ischemic optic neuropathy and combinations thereof.

In one embodiment, the interleukin-1 receptor-Fc fusion protein comprises an amino acid sequence of SEQ ID NO: 1. In one embodiment, the interleukin-1 receptor-Fc fusion protein comprises an amino acid sequence at least 90% identical to SEQ ID NO: 1. In one embodiment, the interleukin-1 receptor-Fc fusion protein comprises CH1 and CH2 domains derived from a human IgG1.

In one embodiment, the treatment allows for the withdrawal or weaning of a concurrent therapy selected from the group consisting of NSAIDs, colchicine, corticosteroid and combinations thereof.

In one embodiment, the subject is diagnosed with recurrent or refractory pericarditis. In one embodiment, the subject is diagnosed with idiopathic pericarditis. In one embodiment, the subject is diagnosed with recurrent idiopathic pericarditis. In one embodiment, the subject is diagnosed with refractory idiopathic pericarditis. In one embodiment, the subject is diagnosed with non-idiopathic pericarditis. In one embodiment, the subject is diagnosed with recurrent non-idiopathic pericarditis. In one embodiment, the subject is diagnosed with refractory non-idiopathic pericarditis. In one embodiment, the subject is diagnosed with post-cardiac injury syndrome (PCIS). In certain embodiments, the subject is diagnosed with post-myocardial infarction pericarditis, post-pericardiotomy syndrome (PPS) or post-traumatic pericarditis. In certain embodiments, the post-myocardial infarction pericarditis is early post-myocardial infarct-associated pericarditis (pericarditis epistenocardica) or late post-myocardial infarction pericarditis (Dressler's Syndrome). In other embodiments, the post-traumatic pericarditis is non-iatrogenic trauma or iatrogenic trauma. In one embodiment, the subject is diagnosed with Adult-Onset Still's Disease.

In one embodiment, the interleukin-1 receptor-Fc fusion protein is rilonacept.

In one embodiment, the subject is colchicine-resistant, corticosteroid-dependent, corticosteroid-intolerant, corticosteroid-refractory and combinations thereof.

In one embodiment, the subject a symptomatic subject with pericarditis with an elevated level of a marker of systemic inflammation, where the CRP level is ≥1 mg/dL; or, is a symptomatic subject with pericarditis with non-elevated levels of an inflammatory marker and with pericardial inflammation present using an imaging technique; the subject being NSAID-, corticosteroid- and/or colchicine-resistant or intolerant; or a subject with NSAID-, corticosteroid- and/or colchicine-dependent pericarditis but does not experience symptoms that would meet the diagnostic criteria for a flare of pericarditis; or a symptomatic subject with PCIS with or without an elevated marker of systemic inflammation; where the subject is NSAID-, corticosteroid- and/or colchicine-resistant or intolerant; and/or with NSAID, corticosteroid- and/or colchicine-dependent PCIS but does not experience symptoms that would meet the diagnostic criteria for PCIS, such as, for example, criteria for a flare of pericarditis.

In one embodiment, administration of the interleukin-1 receptor-Fc fusion protein results in a reduced CRP level selected from less than about 2 mg/dL, less than about 1.5 mg/dL, less than about 1 mg/dL, less than about 0.8 mg/dL, less than about 0.6 mg/dL, less than about 0.5 mg/dL, less than about 0.4 mg/dL, less than about 0.3 mg/dL, less than about 0.2 mg/dL, or less than about 0.1 mg/dL in the subject. In some embodiments, the reduced CRP level is less than about 1 mg/dL. In some embodiments, the reduced CRP level ranges from about 0.3-1 mg/dL. In some embodiments, the reduced CRP level is less than 0.3 mg/dL.

In one embodiment, the CRP level is reduced to less than 1 mg/dL within 2 weeks, within 1 week, within 6 days, within 5 days, within 4 days, within 3 days, within 2 days, or within 1 day from the first administration of the interleukin-1 receptor-Fc fusion protein. In some embodiments, the CRP level is reduced to less than 1 mg/dL within 1 week from the first administration of the interleukin-1 receptor-Fc fusion protein. In some embodiments, the CRP level is maintained at less than 1 mg/dL for more than about 2 weeks, more than about 4 weeks, more than about 1 month, more than about 2 months, more than about 3 months more than about 4 months, more than about 5 months, more than about 6 months, more than about 7 months, more than about 8 months, more than about 10 months, or more than about 1 year. In some embodiments, the CRP level is maintained at less than 1 mg/dL for more than about 2 weeks, more than about 4 weeks, more than about 1 month, more than about 2 months, more than about 3 months more than about 4 months, more than about 5 months, more than about 6 months, more than about 7 months, more than about 8 months, more than about 10 months, or more than about 1 year, while the patient continues to receive a therapeutic dose of interleukin-1 receptor-Fc fusion protein at an administration interval and treatment period according to the invention. In some embodiments, the CRP level is maintained at less than 1 mg/dL for the above-indicated periods while the subject receives interleukin-1 receptor-Fc fusion protein in absence of any concurrent therapy.

In some embodiments, the CRP level is reduced to less than 0.3 mg/dL within 3 weeks from the first administration of the interleukin-1 receptor-Fc fusion protein. In some embodiments, the CRP level is maintained at less than 0.3 mg/dL for more than about 1 week, more than about 2 weeks, more than about 3 weeks, more than about 1 month, more than about 2 months, more than about 3 months more than about 4 months, more than about 5 months, more than about 6 months, more than about 8 months, or more than about 1 year. In some embodiments, the CRP level is maintained at less than 0.3 mg/dL for the above-indicated periods continues to receive a therapeutic dose of interleukin-1 receptor-Fc fusion protein at an administration interval and treatment period according to the invention. In some embodiments, the CRP level is maintained at less than 0.3 mg/dL for the above-indicated periods while the subject receives interleukin-1 receptor-Fc fusion protein in absence of any concurrent therapy.

In one embodiment, administration of the interleukin-1 receptor-Fc fusion protein results in reduction of NRS score to 2 or less.

In one embodiment, the NRS score is reduced to 2 or less within 3 weeks, within 2 weeks or within 1 week from the first administration of the interleukin-1 receptor-Fc fusion protein.

In some embodiments, the NRS score is maintained at 2 or less for more than about 1 week, more than about 2 weeks, more than about 3 weeks, more than about 1 month, more than about 2 months, more than about 3 months more than about 4 months, more than about 5 months, more than about 6 months, more than about 8 months, or more than about 1 year. In some embodiments, the NRS level is maintained at 2 or less for the above-indicated periods while the patient continues to receive a therapeutic dose of interleukin-1 receptor-Fc fusion protein at an administration interval and treatment period according to the invention. In some embodiments, the NRS level is maintained at 2 or less for the above-indicated periods while the subject receives interleukin-1 receptor-Fc fusion protein in absence of any concurrent therapy.

In some embodiments, the interleukin-1 receptor-Fc fusion protein results in a reduced NRS score of 1 or less.

In some embodiments, the NRS score is reduced to 1 or less within 5 weeks, within 4 weeks, within 3 weeks, within 2 weeks, or within 1 week from the first administration of the interleukin-1 receptor-Fc fusion protein at an administration interval and treatment period according to the invention.

In some embodiments, the NRS score is maintained at 1 or less for more than about 1 week, more than about 2 weeks, more than about 3 weeks, more than about 1 month, more than about 2 months, more than about 3 months more than about 4 months, more than about 5 months, more than about 6 months, more than about 8 months, or more than about 1 year. In some embodiments, the NRS level is maintained at 1 or less for the above-indicated periods while the subject receives interleukin-1 receptor-Fc fusion protein at an administration interval and treatment period according to the invention. In some embodiments, the NRS level is maintained at 1 or less for the above-indicated periods while the subject receives interleukin-1 receptor-Fc fusion protein in absence of any concurrent therapy.

In some embodiments, administration of the interleukin-1 receptor-Fc fusion protein results in decreased pericardiac effusion compared to a control. In some embodiments, a control is a baseline pericardiac effusion level measured in the subject prior to the treatment. In some embodiments, a control is a pericardiac effusion level measured in a subject with comparable disease status but treated with a placebo. In some embodiments, a control is a reference value indicative of pericardiac effusion in a subject with comparable disease status without treatment. In some embodiments, a control is indicative of the disease state when a subject having the disease receives a standard of care therapy, in absence of IL-1 receptor-Fc fusion protein administration.

In some embodiments, administration of the interleukin-1 receptor-Fc fusion protein results in absence of pericardiac effusion.

In some embodiments, the decreased or absence of pericardiac effusion is maintained for more than about 2 weeks, more than about 4 weeks, more than about 1 month, more than about 2 months, more than about 3 months more than about 4 months, more than about 5 months, more than about 6 months, more than about 8 months, or more than about 1 year. In some embodiments, the decrease or absence of pericardiac effusion is maintained for the above-indicated period, while the subject continues to receive a therapeutic dose of interleukin-1 receptor-Fc fusion protein at an administration interval and treatment period according to the invention. In some embodiments, the decrease or absence of pericardiac effusion is maintained for the above-indicated period, while the subject receives interleukin-1 receptor-Fc fusion protein in absence of any concurrent therapy.

In some embodiments, administration of the interleukin-1 receptor-Fc fusion protein results in improved cardiac electrical conductivity in the subject as determined by ECG as compared to a control. In some embodiments, the improved cardiac electrical conductivity as determined by ECG comprises reduced ST-elevation and/or reduced SR depression.

In some embodiments, administration of the interleukin-1 receptor-Fc fusion protein results in normalized cardiac electrical conductivity in the subject as determined by an ECG evaluation.

In some embodiments, administration of the interleukin-1 receptor-Fc fusion protein results in improved cardiac effusion in the subject as determined by echocardiographic evaluation (ECHO) as compared to a control.

In some embodiments, administration of the interleukin-1 receptor-Fc fusion protein results in normalized cardiac function in the subject as determined by ECHO evaluation.

In some embodiments, a control is a baseline cardiac parameter (e.g., determined by ECG or ECHO, respectively) measured in the subject prior to the treatment. In some embodiments, a control is a cardiac parameter (e.g., determined by ECG or ECHO, respectively) measured in a subject with comparable disease status but treated with a placebo. In some embodiments, a control is a reference indicative of the cardiac parameter in a subject with comparable disease status without interleukin-1 receptor-Fc fusion protein treatment. In some embodiments, a control is a reference indicative of the cardiac parameter in a subject with comparable disease status, receiving a standard of care treatment, and without the interleukin-1 receptor-Fc fusion protein administration.

In some embodiments, the improved or normalized cardiac parameter is maintained for more than about 2 weeks, more than about 4 weeks, more than about 1 month, more than about 2 months, more than about 3 months more than about 4 months, more than about 5 months, more than about 6 months, more than about 8 months, or more than 1 year. In some embodiments, the normalized cardiac parameter is maintained for the above-indicated period while the subject receives interleukin-1 receptor-Fc fusion protein at an administration interval and treatment period according to the invention. In some embodiments, the normalized cardiac parameter is maintained for the above-indicated period while the subject receives interleukin-1 receptor-Fc fusion protein in absence of any concurrent therapy.

In some embodiments, administration of the interleukin-1 receptor-Fc fusion protein results in improved QoL scores in the subject as compared to a control. In some embodiments, a control is baseline QoL scores determined in the subject prior to the treatment. In some embodiments, a control is reference QoL scores in a subject with comparable disease status but treated with a placebo. In some embodiments, a control is a reference indicative of the QoL scores in a subject with comparable disease status without treatment. In some embodiments, a control is indicative of the QoL when a subject having the disease receives a standard of care therapy, in absence of IL-1 receptor-Fc fusion protein administration.

In some embodiments, the improved QoL scores comprise one or more assessments selected from: Patient Global Impression of Pericarditis Severity (PGIPS); Physician Global Assessment of Pericarditis Activity (PGA-PA); 36-Item Short Form Health Survey (SF-36); 5-Level EuroQoL-5D (EQ-5D-5L) and Insomnia severity Index (ISI).

In some embodiments, the improved QoL scores comprise a reduced ISI indicative of clinically insignificant insomnia having a score value of less than 7 in the 5-point Likert scale.

In some embodiments, the improved QoL scores are maintained for more than 2 weeks, more than 3 weeks, more than 1 month, more than 2 months, more than 3 months, more than 4 months, more than 5 months, more than 6 months, more than 8 months, or more than 1 year from the date of first administration. In some embodiments, the improved QoL scores are maintained for the above-indicated periods while the subject receives interleukin-1 receptor-Fc fusion protein. In some embodiments, the improved QoL scores are maintained for the above-indicated periods while the subject receives interleukin-1 receptor-Fc fusion protein in absence of any concurrent therapy.

In some embodiments, administration of the interleukin-1 receptor-Fc fusion protein results in a period of recurrence-free survival of the subject in absence of other standard of care (SOC) medicines. In some embodiments, the recurrence-free period is at least a month, at least five weeks, at least six weeks, at least seven weeks, at least eight weeks, at least three months, at least four months, at least five months, at least six months, or at least one year.

In some embodiments, the treatment period with interleukin-1 receptor-Fc fusion protein lasts for 1 week. In some embodiments the treatment period with interleukin-1 receptor-Fc fusion protein lasts for 2 weeks, 3 weeks, 4 weeks, 5 weeks, 6 weeks, 7 weeks, 8 weeks, 9 weeks or 10 weeks. In some embodiments, the treatment period lasts 2 months, 3 months, 4 months, 5 months, 6 months, 7 months, 8 months, 9 months, 10 months, 11 months or 1 year. In some embodiments, the treatment period lasts for more than 1 year. In some embodiments, the treatment period encompasses an administration of a dose and a time interval in accordance to the invention.

In some aspects, the invention provides a method of treating post-pericardiotomy syndrome (PPS), the method comprising a step of administering to a subject in need of treatment an interleukin-1 receptor-Fc fusion protein at a therapeutically effective dose and an administration interval for a treatment period sufficient to improve, stabilize or reduce one or more symptoms of post-pericardiotomy pericarditis relative to a control.

In some embodiments, the invention provides a method of treating pericarditis, PCIS or PPS by administering an interleukin-1 (IL-1) antagonist a therapeutically effective dose and an administration interval for a treatment period sufficient to improve, stabilize or reduce one or more symptoms of post-pericardiotomy pericarditis relative to a control. In some embodiments, the interleukin-1 antagonist is an IL-1α, IL-1β or IL-1 receptor binding protein (e.g., an anti-IL-1α antibody or a fragment thereof), a soluble receptor for interleukin-1, IL-1ra or an interleukin-1 receptor fusion protein.

It is to be understood that all embodiments as described above are applicable to all aspects of the present invention.

BRIEF DESCRIPTION OF THE DRAWINGS

The drawings are for illustration purposes only not for limitation.

FIG. 1A-I depicts serum CRP levels and pain in NRS units in nine patients, designated as Subjects A-I respectively after being administered 320 mg loading dose of interleukin-1 receptor-Fc fusion protein at day 0, followed by 160 mg once a week. X-axis shows days after treatment. Subjects A-I were enrolled under Group 1. The respective concurrent treatments and duration are designated graphically below the X-axis.

FIG. 5 is a representative table of additional outcome measures, such as presence of effusion, QoL and ECG changes, acquired from subjects in Groups 1-3 from the phase II clinical trial described in Example 2.

DEFINITIONS

Figure 1A:
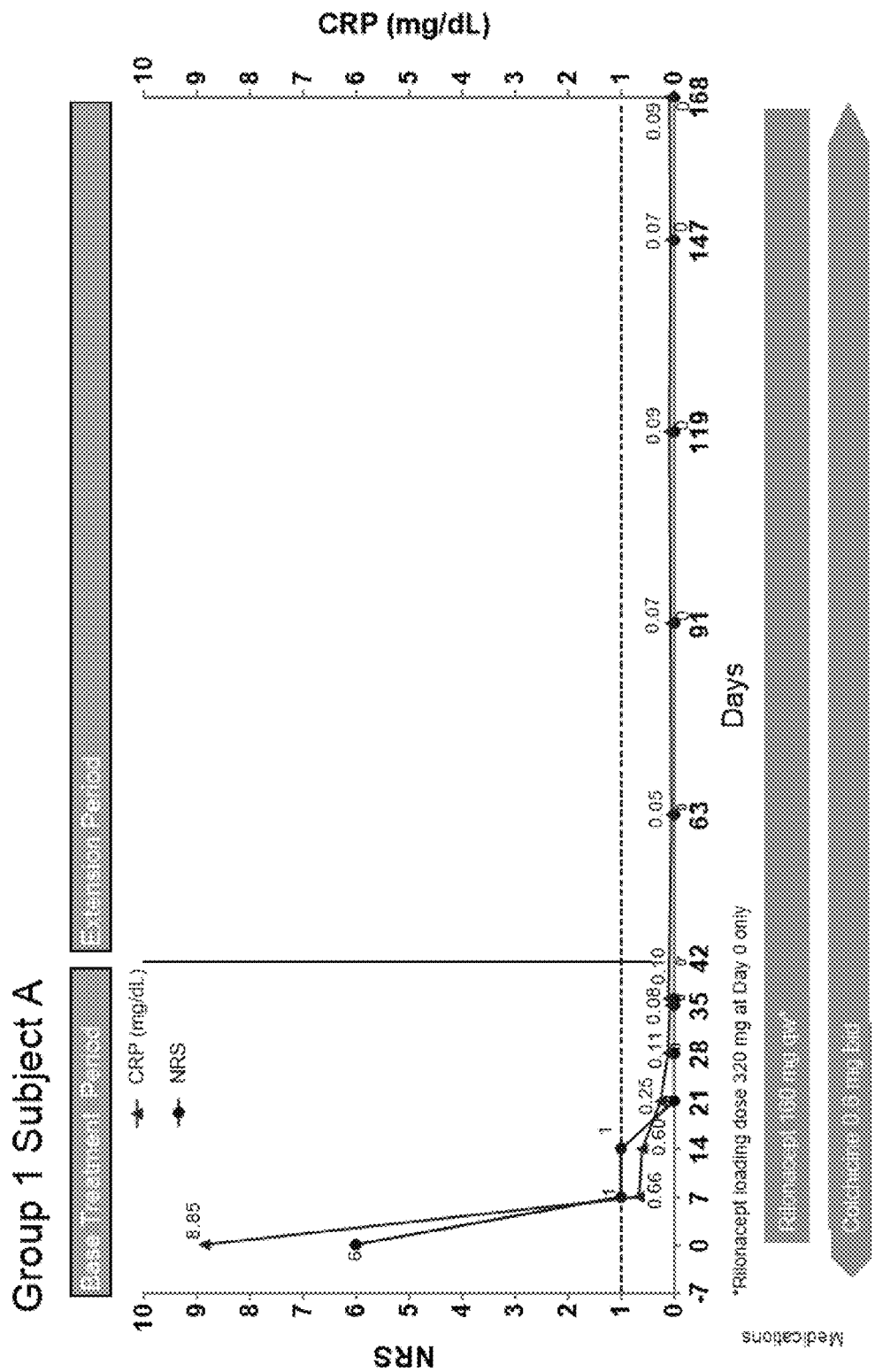

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues. In some embodiments, amelioration includes decreasing levels of relevant protein or its activity that is pathologically elevated in relevant disease tissues.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein, e.g., a subject who is administered a placebo. A "control subject" is a subject with the same disease as the subject being treated, but who received no treatment, or who received placebo.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLAS TN for nucleotide sequences and BLASTP, gapped BLAST, and PSI-BLAST for amino acid sequences. Exemplary such programs are described in Altschul, et al., Basic local alignment search tool, *J Mol. Biol.*, 215(3): 403-410, 1990; Altschul, et al., Methods in Enzymology; Altschul et al., *Nucleic Acids Res.* 25:3389-3402, 1997; Baxevanis et al., *Bioinformatics: A Practical Guide to the Analysis of Genes and Proteins, Wiley*, 1998; and Misener, et al., (eds.), *Bioinformatics Methods and Protocols (Methods in Molecular Biology*, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suitable for subcutaneous delivery: As used herein, the phrase "suitable for subcutaneous delivery" or "formulation for subcutaneous delivery" as it relates to the pharmaceutical compositions of the present invention generally refers to the stability, viscosity, tolerability and solubility properties of such compositions, as well as the ability of such compositions to deliver an effective amount of antibody contained therein to the targeted site of delivery.

Patient: As used herein, the term "patient" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Recurrence: As used herein, the term "recurrence" is defined as the recurrence of typical pericarditis pain associated with supportive objective evidence of pericarditis. Recurrence is often used interchangeably with "flare" and "relapse". A pericarditis recurrence is usually indicated by any one or more of the following: an increase in the CRP level of ≥1 mg/dl in peripheral blood; or an increase in pain, determined in an NRS scale of ≥4; or occurrence of pericardial effusion; a pericardial rub; or fever or any other symptomatic indication of the pericardial disease.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Target tissues: As used herein, the term "target tissues" refers to any tissue that is affected by a disease or disorder to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods of treating pericarditis comprising a step of administering to a subject in need of treatment an interleukin-1 receptor-Fc fusion protein at a therapeutically effective dose and an administration interval for a treatment period sufficient to improve, stabilize or reduce one or more symptoms of pericarditis relative to a control.

Various aspects of the invention are described in detail in the following sections. The use of sections is not meant to limit the invention. Each section can apply to any aspect of the invention. In this application, the use of "or" means "and/or" unless stated otherwise.

Post-Cardiac Injury Syndromes

Post-cardiac injury syndrome (PCIS) refers to an aetiologic heterogeneous group of autoimmune-mediated conditions of pericardial, epicardial, and myocardial inflammation. An invasive cardiac procedure or accidental trauma may give rise to myocardial, epicardial and pericardial damage. Inflammation of the epicardium and pericardium can lead to obvious symptoms such as pain, effusions, and fever. Patients suffering from PCIS may present with chest pain, low grade fever and dyspnoea. Clinical symptoms include mild to moderate effusions both in the pericardium and in the pleural space, and, in certain cases, pericardial friction rubs on auscultation. Laboratory analysis shows systemic inflammation with elevation of CRP and blood leucocytes.

In some cases, PCIS represents a leading cause of pericarditis. The resulting tissue damage can lead to accumulation of debris and blood in the pericardium. This results in immune responses, in which the inflammation persists in certain patients susceptible to this condition.

Symptom of PCISs include non-idiopathic pericarditis. As a group, PCISs, are an emerging cause of pericarditis and pericardial diseases, especially in developed countries and have been reported recently in about 10% of unselected cases of acute pericarditis (Imazio, Int. J. Cardiol. 2013; 168:648-652). PCIS develops within days to months after cardiac, pericardial injury or both and unlike post-myocardial infarction syndrome, post-cardiac injury syndrome may acutely provoke a greater anti-heart antibody response (anti-sarcolemmal and antifibrillary). PCIS includes post-infarction pericarditis (Maisch et al, Eur Heart J. 2004; 25:587-610). Post-myocardial infarction pericarditis includes two distinct forms; an "early" form (pericarditis epistenocardica) and a "delayed" form (Dressler's syndrome). Epistenocardiac pericarditis, caused by direct exudation, occurs in 5-20% of transmural myocardial infarctions, but is clinically discovered rarely, and Dressler's syndrome occurs from one week to several months after clinical onset of myocardial infarction with symptoms and manifestations similar to the post-cardiac injury syndrome (Maisch et al, 2004; 25:587-610). PCIS also includes post-pericardiotomy syndrome (PPS). PPS is a relatively frequent complication of cardiac surgery with an incidence of 10-40% in patients undergoing cardiac operation and often occurs days to several weeks after cardiac surgery (Finkelstein et al, Herz. 2002; 27(8): 791-794; Imazio et al, Eur. Heart. J. 2010; 31(22):2749-2754; Imazio et al, JAMA. 2014; 312(10):1016-1023). PCISs also include post-traumatic pericarditis, including non-iatrogenic trauma (i.e., following accidental blunt or penetrating thoracic trauma) and iatrogenic trauma (i.e., after percutaneous coronary or intracardiac interventions, such as pacemaker lead insertion, radiofrequency ablation). Without wishing to be bound by any theory, PCISs are presumed to have an autoimmune pathogenesis triggered by an initial damage of pericardial and/or pleural mesothelial cells, caused by the foregoing clinical conditions.

Pericarditis

Pericarditis is swelling and irritation of the pericardium, the thin saclike membrane surrounding the heart. Pericarditis often causes chest pain and sometimes other symptoms. The sharp chest pain associated with pericarditis occurs when the irritated layers of the pericardium rub against each other. Signs and symptoms of pericarditis may include some or all of the following: sharp, piercing chest pain over the center or left side of the chest, which is generally more intense when breathing in or reclining; shortness of breath when reclining; heart palpitations; low-grade fever; an overall sense of weakness, fatigue or feeling sick; cough; and abdominal or leg swelling.

Pericarditis accounts for 5% of emergency department visits for chest pain in the absence of myocardial infarction (Khandaker et al, Mayo Clin Proc. 2010; 85:572-593). In 80% of cases in developed countries, the cause of pericarditis is either post viral or "idiopathic," in that it cannot be attributed to a specific condition (Imazio et al, Circulation. 2010; 121:916-928; Zayas et al, Am J Cardiol. 1995; 75:378-382). Diagnosis is based on the presence of typical chest pain (improved by sitting up and leaning forward) along with fever, pericardial friction rub, electrocardiographic (ECG) changes, pericardial effusion, or elevated markers of inflammation (white blood cell [WBC] count, C-reactive protein [CRP], or erythrocyte sedimentation rate [ESR]) (Imazio, Revista Espanola de Cardiologia. 2014; 67(5):345-348). The European Society of Cardiology (ESC) Guidelines for the Diagnosis and Management of Pericardial Diseases define a pericarditis episode as the presence of at least 2 of the 4 following criteria: pericarditic chest pain, pericardial rubs, new widespread ST-elevation or PR depression on ECG, and pericardial effusion (new or worsening). Elevations of markers of inflammation (i.e., CRP, ESR, and WBD) or evidence of pericardial inflammation by an imaging technique (e.g., magnetic resonance imaging [MM]) are used as supportive findings (Adler et al, Eur Heart J. 2015 Nov. 7; 36(42):2921-64). Recurrent pericarditis is a common complication of acute pericarditis and affects 20-30% of patients (Imazio, Revista Espanola de Cardiologia. 2014; 67(5):345-348). It is characterized by the recurrence of signs and symptoms of pericarditis after a symptom-free interval of at least 4-6 weeks (Adler et al, Eur Heart J. 2015 Nov. 7; 36(42):2921-64). The underlying pathogenesis of idiopathic recurrent pericarditis (RIP) remains unclear, although immune-mediated mechanisms are believed to play a key role in the pathogenesis (Imazio et al, American Journal of Cardiology, 2005; 96(5):736-739). A growing body of evidence suggests that these immune responses consist of both pathogenic autoimmune and auto-inflammatory processes (Cantarini et al, Autoimmunity Reviews 2015; 14:90-97; Doria et al, Autoimmunity Reviews 2012; 12:22-30). The presence of pro-inflammatory cytokines in the pericardial fluid of RIP patients lends direct support to both an auto-immune and/or auto-inflammatory etiopathogenesis (Pankuwait et al, 2000).

Currently available treatments for pericarditis include nonsteroidal anti-inflammatory drugs (NSAIDs), colchicine, and glucocorticoids (Lilly, 2013). Aspirin and other NSAIDs are the first-line approach. Several other NSAID commonly used are, ibuprofen, celecoxib, diclofenac, diflunisal, indomethacin, to name a few. Because high doses are often required, consideration has to be given to gastric protection therapy. Colchicine is another mainstay therapy for RIP and is commonly used with NSAIDs, but a subset of patients has refractory symptoms and significant gastrointestinal side effects, including severe diarrhea, leading to discontinuation for intolerability. Glucocorticoids should be prescribed only to patients with idiopathic pericarditis who are refractory or intolerant to treatment with NSAIDs plus colchicine, because of the side effects associated with long-term corticosteroid therapy and because of a high rate of relapse when the corticosteroid is tapered or stopped (Maisch et al, Eur Heart J. 2004; 25:587-610; Imazio et al, Circulation. 2005; 112:2012-2016; Lotrionte et al, Am Heart J. 2010; 160:662-670), particularly in the absence of colchicine treatment. Patients with refractory symptoms can be particularly challenging to manage, and multiple immunosuppressive medications have been used without consistent benefit (Baskar et al, Cardiol Res Pract. 2016; 2016:7840724).

The cause of pericarditis is often hard to determine. In most cases, doctors either are unable to determine a cause (idiopathic) or suspect a viral infection. Although the underlying pathogenesis of idiopathic recurrent pericarditis (RIP) (sometimes used interchangeably with recurrent idiopathic pericarditis) remains unclear, immune-mediated mechanisms are believed to play a key role in the pathogenesis (Imazio et al, 2005; 96(5):736-739). A growing body of evidence suggests that these immune responses consist of both pathogenic autoimmune and auto-inflammatory processes (Cantarini et al, Autoimmunity Reviews 2015; 14:90-97; Doria et al, Autoimmunity Reviews 2012; 12:22-30). The presence of pro-inflammatory cytokines in the pericardial fluid of RIP patients lends direct support to both an autoimmune and/or auto-inflammatory etiopathogenesis (Pankuwait et al, 2000).

Interleukin-1 (IL-1) is a key cytokine that drives the pathophysiology of many inflammatory processes. It is implicated as a causative factor in various inflammatory human diseases. Although the pathogenic mechanism of auto-inflammatory disease is not completely understood, there is a growing body of evidence that IL-1 may be a primary driver of the symptomology and that targeting this cytokine may provide important benefits (Hoffman & Patel, Arthritis and Rheum. 2004 February; 50(2): 345-349). In fact, a study of once-daily anakinra (KINERET®), a recombinant form of the human IL-1 receptor antagonist (IL-1RA), showed promising effects in RIP patients when colchicine failed and corticosteroid dependence (or intolerance) developed, with C-reactive protein (CRP) normalization within a mean of 7.1 days in 21 consecutively treated patients (Brucato et al, JAMA. 2016 Nov. 8; 316(18):1906-1912; Lazaros et al, J Cardiovasc Med 2016; 17(4):256-62). However, anakinra is a once-daily injection and is known to cause injection site reaction among other adverse events. Thus, an IL-1 antagonist, with an improved product profile that provides for one or more of patient convenience; less treatment discomfort; effective withdrawal or weaning of NSAIDs, colchicine and/or corticosteroid therapies; and a dosing frequency that facilitates a safe and effective weaning regimen prescribed by a physician, such as the interleukin-1 receptor-Fc fusion proteins described herein, that antagonize binding of both IL-1α and IL-1β and prevents their interaction with IL-1 cell surface receptors, provides a therapeutic opportunity for the treatment of PCISs and pericarditis.

There are several different methods for assessing symptoms of pericarditis. In one embodiment, one or more symptoms of pericarditis are assessed by a Numerical Rating Scale (NRS) for assessment of pericarditis pain. NRS score is a self-reported assessment of the level of pain a patient experiences in a scale of 0 to 10. In this 11-point NRS scale, a score of 0 is interpreted as no pain, and a score of 10 is the most severe pain. In one embodiment, one or more signs of pericarditis are assessed by an echocardiogram. In one embodiment, the one or more signs of pericarditis assessed by an echocardiogram comprise pericardial effusion. In one embodiment, one or more signs of pericarditis are assessed by an electrocardiogram (ECG). In one embodiment, the one or more signs of pericarditis assessed by an ECG comprise widespread ST-elevation and/or PR depression. In one embodiment, one or more signs of pericarditis comprise fever and/or pericardial rub. In one embodiment, one or more signs and/or symptoms of pericarditis are assessed by cardiac magnetic resonance imaging (MRI). In one embodiment, one or more signs of pericarditis are assessed by measuring blood levels of C-reactive protein (CRP). In one embodiment, measuring blood levels of CRP comprises measuring blood levels of CRP at several time points after an administering an initial loading dose of the interleukin-1 receptor-Fc fusion protein, wherein a linear regression is performed to determine the change of CRP levels from baseline, change of CRP levels from baseline adjusted for placebo effect and/or the slope of blood levels of CRP over time. In some embodiments, a CRP level of greater than 1 mg/dL is considered positive for inflammation. In one embodiment, one or more symptoms of pericarditis are assessed by a Quality of Life Questionnaire.

Treatment

Among other things, methods according to the invention include treating subjects having PCIS or pericarditis by administering a therapeutically effective amount of an IL-1 receptor-Fc fusion protein. In certain cases, the pericarditis may be associated with, or a symptom of a PCIS, while in other cases the cause of the pericarditis may be of uncertain or unknown origin (i.e., idiopathic). In some embodiments of the invention, a PCIS or pericarditis is treated by administering to a subject in need of treatment an interleukin-1 receptor-Fc fusion protein at a therapeutically effective dose and an administration interval for a treatment period sufficient to improve, stabilize or reduce one or more signs and/or symptoms of pericarditis relative to a control. In some embodiments, the invention provides a method of treating subjects having post-pericardiotomy syndrome (PPS). Post-pericardiotomy is known to cause pericarditis. In some embodiments, PPS and/or PPS associated pericarditis is treated by administering to a subject in need of treatment an IL-1 antagonist, such as an interleukin-1 receptor-Fc fusion protein at a therapeutically effective dose and an administration interval for a treatment period sufficient to improve, stabilize or reduce one or more signs and/or symptoms of pericarditis relative to a control. In some embodiments, treatment of PPS with an interleukin-1 receptor-Fc fusion protein at a therapeutically effective dose and an administration interval for a period can result in prevention of pericarditis, or delay in the appearance one or more signs and/or symptoms of pericarditis. The terms, "treat" or "treatment," as used herein, refers to amelioration of one or more signs and/or symptoms associated with the disease or disorder, prevention or delay of the onset of one or more signs and/or symptoms of the disease or disorder, and/or lessening of the severity or frequency of one or more signs and/or symptoms of the disease or disorder.

In some embodiments of the invention, the subject has one or more of the following: recurrent or refractory pericarditis, idiopathic pericarditis, recurrent idiopathic pericarditis, refractory idiopathic pericarditis, non-idiopathic pericarditis, recurrent non-idiopathic pericarditis, refractory non-idiopathic pericarditis. In other embodiments, the subject has a PCIS. In certain embodiments, a subject with PCIS has pericarditis. In various embodiments, the PCIS is, for example, post-myocardial infarction pericarditis, PPS or post-traumatic pericarditis. In certain embodiments, the post-myocardial infarction pericarditis is early post-myocardial infarct-associated pericarditis (pericarditis epistenocardica) or late post-myocardial infarction pericarditis (Dressler's Syndrome). In other embodiments, the post-traumatic pericarditis is non-iatrogenic trauma or iatrogenic trauma. In one embodiment, a subject with PPS, e.g., recurrent PPS, has pericarditis. In certain embodiments, the subject to be treated is selected from:

(i) a symptomatic subject with pericarditis with an elevated level of a marker of systemic inflammation (e.g., CRP≥1 mg/dL);

(ii) a symptomatic subject with pericarditis with non-elevated levels of an inflammatory marker (e.g., CRP<1 mg/dL) and with pericardial inflammation present using an imaging technique (e.g., MRI);

(iii) the subject of (i) or (ii), where the subject is NSAID-, corticosteroid- and/or colchicine-resistant or intolerant;

(iv) a subject with NSAID, corticosteroid- and/or colchicine-dependent pericarditis not experiencing symptoms that would meet the diagnostic criteria for a recurrence of pericarditis;

(v) a symptomatic subject with PCIS with or without an elevated marker of systemic inflammation (e.g., CRP≥1 mg/dL);

(vi) the subject of (v), where the subject is NSAID-, corticosteroid- and/or colchicine-resistant or intolerant; and (vii) a subject with NSAID-, corticosteroid- and/or colchicine-dependent PCIS not experiencing symptoms that would meet the diagnostic criteria for PCIS, such as, for example, criteria for a recurrence of pericarditis.

In certain embodiments, the subject administered a therapeutically effective amount of an IL-1 receptor-Fc fusion protein may be treated with concomitant medications, such as NSAIDs, colchicine or corticosteroids, and combinations thereof, and optionally weaned from one or more of such concomitant medications following treatment with the IL-1 receptor-Fc fusion protein. Typically, exemplary NSAIDs include but are not limited to ibuprufen, aspirin, indomethaxin, celecoxib, diclofenac. Exemplary corticosteroids include prednisone, cortisone, methyl prednisolone, and others.

In certain embodiments, the subject administered a therapeutically effective amount of an IL-1 receptor-Fc fusion protein may also be treated with concomitant medications, such as NSAIDs, colchicine or corticosteroids, and combinations thereof, and optionally weaned from one or more of such concomitant medications following treatment with the IL-1 receptor-Fc fusion protein.

In some embodiments, the administration of an interleukin-1 receptor-Fc fusion protein results in a statistically-significant drop on a Numerical Rating Scale (NRS) for assessment of pericarditis pain. In some embodiments, the administration of an interleukin-1 receptor-Fc fusion protein results in a statistically-significant change on a composite endpoint that includes two or more of the following: NRS, blood levels of CRP, ECHO, pericardial rub, ECG, WBD, ESR and MRI.

In some embodiments, the step of administering comprises subcutaneous administration. In some embodiments, subcutaneous administration is through subcutaneous injection. In some embodiments, subcutaneous administration is through a subcutaneous pump. In some embodiments, subcutaneous injection of the interleukin-1 receptor-Fc fusion protein can be performed in the upper arm, the anterior surface of the thigh, the lower portion of the abdomen, the upper back or the upper area of the buttock. In some embodiments, the site of injection is rotated.

In some embodiments, the effect of an interleukin-1 receptor-Fc fusion protein on pericarditis is measured relative to a control. In some embodiments, a control is indicative of the one or more symptoms of pericarditis in the subject before the treatment (also referred to as a baseline). In some embodiments, the control is indicative of the one or more symptoms of pericarditis as determined by evaluating health information from pericarditis patients over time, demonstrating the natural progress of the condition, which can be obtained, for example, from a natural history study of pericarditis. In some embodiments, a control is indicative of the one or more symptoms of pericarditis in a subject with comparable disease status without treatment. In some embodiments, a control is indicative of the one or more symptoms of pericarditis in a subject with comparable disease status, who is treated with a placebo. In some embodiments, a control is indicative of a disease state in a subject with comparable disease status, who receives a standard of care therapy, in absence of IL-1 receptor-Fc fusion protein administration.

In some embodiments, one or more symptoms of pericarditis in a subject before treatment comprises a CRP value equal to or greater than 1 mg/dL. In some embodiments, a subject in need of treatment has had an index episode of pericarditis. In some embodiments, an index episode of pericarditis met at least two criteria for an acute pericarditis event, wherein the criteria comprise pericarditic chest pain, pericardial rubs, new widespread ST-segment elevation or PR-segment depression on ECG, and new or worsening pericardial effusion. In some embodiments, a subject in need of treatment has had at least one recurrent episode of pericarditis. In some embodiments, a subject in need of treatment has had at least two recurrent episodes of pericarditis. In some embodiments, a subject in need of treatment has had at least three recurrent episodes of pericarditis. In some embodiments, a recurrent episode is defined as at least 1 day with pericarditis pain with pericarditis pain measurement ≥4 on the 11-point Numerical Rating Scale (NRS) and/or C-reactive protein (CRP) level ≥1 mg/dL. In some embodiments, pericarditis pain ≥4 and CRP≥1 mg/dL are present on the same day. In some embodiments, pericarditis pain ≥4 and CRP≥1 mg/dL are not present on the same day. In some embodiments, a subject being treated has at least one recurrent episode within 7 days prior to first administration. In some embodiments, a subject in need of treatment has an ongoing symptomatic episode of pericarditis.

Dosage

A therapeutically effective dose of an interleukin-1 receptor-Fc fusion protein for treating pericarditis can occur at various dosages. In some embodiments of the invention, a therapeutically effective dose is equal to or greater than 20 mg, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, 500 mg, 520 mg, 540 mg, 560 mg, 580 mg, 600 mg, 620 mg, 640 mg, 660 mg, 680 mg, 700 mg, 720 mg, 740 mg, 760 mg, 780 mg, 800 mg, 820 mg, 840 mg, 860 mg, 880 mg, 900 mg, 920 mg, 940 mg, 960 mg, 980 mg, or 1000 mg.

In some embodiments, a therapeutically effective dose is approximately 20-800 mg, approximately 40-700 mg, approximately 60-600 mg, approximately 80-500 mg, approximately 100-400 mg, or approximately 80-400 mg, 100-400 mg, 120-400 mg, approximately 140-400 mg, approximately 160-400 mg, approximately 180-400 mg, approximately 200-400 mg, approximately 220-400 mg, approximately 240-400 mg, approximately 260-400 mg, approximately 280-400 mg, approximately 300-400 mg, approximately 320-400 mg, approximately 340-400 mg, approximately 360-400 mg, approximately 380-400 mg, approximately 20-380 mg, approximately 20-360 mg, approximately 20-340 mg, approximately 20-320 mg, approximately 20-300 mg, approximately 20-280 mg, approximately 20-260 mg, approximately 20-240 mg, approximately 20-220 mg, approximately 20-200 mg, approximately 20-180 mg, approximately 20-160 mg, approximately 20-140 mg, approximately 20-120 mg, approximately 20-100 mg, approximately 20-80 mg, approximately 20-60 mg, or approximately 20-40 mg. In one embodiment, a therapeutically effective dose is approximately 80-160 mg.

In some embodiments, a therapeutically effective dose is equal to or greater than 320 mg/mL. In some embodiments, a therapeutically effective dose comprises an initial loading dose equal to or greater than 320 mg. In some embodiments, the initial loading dose is delivered as two injections of 160 mg. In some embodiments, a therapeutically effective dose is equal to or greater than 160 mg. In some embodiments, a therapeutically effective dose comprises a maintenance dose equal to or greater than 160 mg. In some embodiments, a therapeutically effective dose comprises an initial loading dose equal to or greater than 160 mg. In some embodiments, the initial loading dose is delivered as two injections of 80 mg. In some embodiments, a therapeutically effective dose is equal to or greater than 80 mg. In some embodiments, a therapeutically effective dose comprises a maintenance dose equal to or greater than 80 mg.

In some embodiments, a therapeutically effective dose is delivered as a volume of less than or equal to 2.0 mL for each subcutaneous injection. In some embodiments, a therapeutically effective dose is delivered as a volume of less than or equal to 1.8 mL. In some embodiments, a therapeutically effective dose is delivered as a volume of less than or equal to 1.6 mL. In some embodiments, a therapeutically effective dose is delivered as a volume of less than or equal to 1.4 mL. In some embodiments, a therapeutically effective dose is delivered as a volume of less than or equal to 1.2 mL. In some embodiments, a therapeutically effective dose is delivered as a volume of less than or equal to 1.0 mL. In some embodiments, a therapeutically effective dose is delivered as a volume of less than or equal to 0.8 mL. In some embodiments, a therapeutically effective dose is delivered as a volume of less than or equal to 0.6 mL.

In one embodiment, the therapeutically effective dose is equal to or greater than 0.1 mg/kg, 0.5 mg/kg, 1 mg/kg, 2 mg/kg, 3 mg/mg, 4 mg/kg, 5 mg/kg, 6, mg/kg, 7 mg/kg, 8 mg/kg, 9 mg/kg or 10 mg/kg. In one embodiment, the therapeutically effective dose is approximately 0.1-10 mg/kg, approximately 0.5-10 mg/kg, approximately 1-10 mg/kg, approximately 2-10 mg/kg, approximately 3-10 mg/kg, approximately 4-10 mg/kg, approximately 5-10 mg/kg, approximately 6-10 mg/kg, approximately 7-10 mg/kg, approximately 8-10 mg/kg, approximately 9-10 mg/kg, approximately 0.1-10 mg/kg, approximately 0.1-9 mg/kg, approximately 0.1-8 mg/kg, approximately 0.1-7 mg/kg, approximately 0.1-6 mg/kg, approximately 0.1-5 mg/kg, approximately 0.1-4 mg/kg, approximately 0.1-3 mg/kg, approximately 0.1-2 mg/kg, approximately 0.1-1 mg/kg, approximately 0.1-0.5 mg/kg.

In some embodiments, a therapeutically effective dose for a pediatric subject (e.g., aged 2 to 17 years, aged 6 to <18 years) comprises an initial loading dose of approximately 4 mg/kg, (e.g., 4.0 mg/kg, 4.1 mg/kg, 4.2 mg/kg, 4.3 mg/kg, 4.4 mg/kg, or 4.5 mg/kg), up to a maximum of approximately 320 mg, delivered, for example, as one or two subcutaneous injections with a maximum single-injection volume of 2 mL. In some embodiments, the initial loading dose described herein (e.g., 4.4 mg/kg) is delivered as two injections of equal dose amount (e.g., 2 injections of 2.2 mg/kg). In some embodiments, a therapeutically effective dose for a pediatric subject (e.g., aged 2 to 17 years, aged 6 to <18 years) comprises a maintenance dose of approximately 2 mg/kg (e.g., 2.0 mg/kg 2.1 mg/kg, 2.2 mg/kg, 2.3 mg/kg 2.4 mg/kg or 2.5 mg/kg), up to a maximum of approximately 160 mg, administered, for example, as a single subcutaneous injection, up to 2 mL in volume. In some embodiments, the therapeutically dose for a pediatric subject comprises a maintenance dose of approximately 1.5 mg/kg to 2.5 mg/kg per week, or 1.8 mg/kg to 2.4 mg/kg per week, or 2 mg/kg to 2.2 mg/kg per week.

In some embodiments, administering comprises an initial loading dose, followed by at least one maintenance dose. In some embodiments, multiple maintenance doses are administered following the initial loading dose. Typically, the maintenance dose is administered periodically (e.g., weekly, once every two weeks, once every three weeks, once every four weeks, monthly, once every five weeks). In some embodiments, the initial loading dose is greater than the at least one maintenance dose. In some embodiments, the initial loading dose is at least one-fold, two-fold, three-fold, four-fold or five-fold greater in dosage than the dosage of the at least one maintenance dose. In some embodiments, the initial loading dose is two-fold greater in dosage than the dosage of the at least one maintenance dose.

Administration Interval

An administration interval of an interleukin-1 receptor-Fc fusion protein in the treatment of pericarditis can occur at various durations. In some embodiments, the administration interval is every other day. In some embodiments, the administration interval is multiple times a week. In some embodiments, the administration interval is at least five days. In some embodiments, the administration interval is once every week. In some embodiments, the administration interval is once every two weeks. In some embodiments, the administration interval is once every three weeks. In some embodiments, the administration interval is once every four weeks. In some embodiments, the administration interval is once every five weeks.

Treatment Period

A treatment period of pericarditis with an interleukin-1 receptor-Fc fusion protein can vary in duration. In some embodiments, the treatment period is 1 week. In some embodiments, the treatment period with interleukin-1 receptor-Fc fusion protein lasts for more than 1 week. In some embodiments the treatment period with interleukin-1 receptor-Fc fusion protein lasts for 2 weeks, 3 weeks, 4 weeks, 5 weeks, 6 weeks, 7 weeks, 8 weeks, 9 weeks or 10 weeks. In some embodiments, the treatment period lasts 1 month, 2 months, 3 months, 4 months, 5 months, 6 months, 7 months, 8 months, 9 months, 10 months, 11 months, 12 months, 13 months, 14 months, 15 months, 16 months, 17 months or 18 months. In some embodiments, the treatment period lasts for more than 18 months. In some embodiments, the treatment period lasts for 2 years. The treatment period encompasses administering the interleukin-1 receptor-Fc fusion protein at a dose and a time interval in accordance to the invention.

In some embodiments, the treatment period is at least one month. In some embodiments, the treatment period is at least two months. In some embodiments, the treatment period is at least three months. In some embodiments, the treatment period is at least six months. In some embodiments, the treatment period is at least nine months. In some embodiments, the treatment period is at least one year. In some embodiments, the treatment period is at least two years. In some embodiments, the treatment period continues throughout the subject's life.

Pharmacokinetics and Pharmacodynamics

Evaluation of interleukin-1 receptor-Fc fusion protein concentration-time profiles in serum of subjects with pericarditis may be evaluated directly by measuring systemic serum interleukin-1 receptor-Fc fusion protein concentration-time profiles. Typically, interleukin-1 receptor-Fc fusion protein pharmacokinetic and pharmacodynamic profiles are evaluated by sampling the blood of treated subjects periodically. The following standard abbreviations are used to represent the associated pharmacokinetic parameters.

$C_{max}$ maximum concentration $t_{max}$ time to maximum concentration $AUC_{0-t}$ area under the concentration-time curve (AUC) from time zero to the last measurable concentration, calculated using the linear trapezoidal rule for increasing concentrations and the logarithmic rule for decreasing concentrations $AUC_{0-\infty}$ AUC from time zero to infinity calculated using the formula:

$$AUC_{0-\infty} = AUC_{0-t} + \frac{C_t}{\lambda_z}$$

where $C_t$ is the last measurable concentration and $\lambda_z$ is the apparent terminal elimination rate constant $\lambda_z$ apparent terminal elimination rate constant, where $\lambda_z$ is the magnitude of the slope of the linear regression of the log concentration versus time profile during the terminal phase $t_{1/2}$ apparent terminal elimination half-life (whenever possible), where $t_{1/2}$=natural log (ln)(2)/$\lambda_z$ CL clearance Vd volume of distribution (IV doses only)

Vd/F apparent volume of distribution (SC doses only)

Typically, actual blood sample collection times relative to the start of interleukin-1 receptor-Fc fusion protein administration are used in PK analysis. For example, blood samples are typically collected, for example, within 15 or 30 minutes prior to interleukin-1 receptor-Fc fusion protein administration (pre-injection baseline or time 0) and at periodic intervals following administration, e.g., hours 1, 4, 8 or 12, or days 1 (24 hours), 2, 3, 4, 5, 6, 7, 10, 14, 17, 21, 24, 28, 31, 38, 45, 52, 60, 70 or 90 days, following administration. In some embodiments, the blood samples are collected prior to an administration timepoint.

Various methods may be used to measure interleukin-1 receptor-Fc fusion protein concentration in serum. As a non-limiting example, enzyme-linked immunosorbent assay (ELISA) methods are used.

Pharmacokinetic parameters may be evaluated at any stage during the treatment, for example, at day 1, day 2, day 3, day 4, day 5, day 6, week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or later. In some embodiments, pharmacokinetic parameters may be evaluated at month 1, month 2, month 3, month 4, month 5, month 6, month 7, month 8, month 9, month 10, month 11, month 12, month 13, month 14, month 15, month 16, month 17, month 18, month 19, month 20, month 21, month 22, month 23, month 24, or later during the treatment.

Effectiveness Assessment

In some embodiments, the effectiveness of the treatment using interleukin-1 receptor-Fc fusion protein is determined by measuring inflammation, such as measuring the CRP level in peripheral blood. In some embodiments administration of the interleukin-1 receptor-Fc fusion protein results in a reduction of the CRP level compared to a score observed prior to the administration. In some embodiments, the CRP level is reduced to 2 mg/dL or less, 1.5 mg/dL or less, 1 mg/dL or less, 0.8 mg/dL or less, 0.6 mg/dL or less, 0.5 mg/dL or less, 0.4 mg/dL or less, 0.3 mg/dL or less, 0.2 mg/dL or less, 0.1 mg/dL or less in the subject. In some embodiments the reduction of CRP level is observed within 2 weeks from the first administration. In some embodiments, the CRP level is maintained at 2 mg/dL or less for longer than 2 weeks. In some embodiments, the CRP level is maintained at 2 mg/dL or less for longer than 1 month, 2 months, 3 months, 4 months, 5 months, 6 months, 7 months, 8 months, 9 months, 10 months, 11 months or for longer than 1 year. In some embodiments, the CRP level is maintained at 1 mg/dL or less for longer than 1 month, 2 months, 3 months, 4 months, 5 months, 6 months, 7 months, 8 months, 9 months, 10 months, 11 months or for longer than 1 year. In some embodiments, the CRP level is maintained at 1 mg/dL or less for the indicated period, while the patient continues to receive a therapeutic dose of interleukin-1 receptor-Fc fusion protein. In some embodiments, the CRP level is maintained at less than 1 mg/dL for the above-indicated periods while the subject receives interleukin-1 receptor-Fc fusion protein in absence of any concurrent therapy.

In some embodiments, the effectiveness of the treatment using interleukin-1 receptor-Fc fusion protein is determined by assessment of pain in the subject, such as by determination of 11-point NRS score. In some embodiments administration of the interleukin-1 receptor-Fc fusion protein results in a reduction of the NRS score compared to a score observed prior to administration. In some embodiments, an NRS score of 3 or less is interpreted as mild to no pain. In some embodiments, a reduction in NRS score to a value of 2 or less after administration of the interleukin-1 receptor-Fc fusion protein from a higher score observed prior to the administration is considered an improvement of the disease in the patient. In some embodiments the NRS score is reduced to 2 or less within 2 weeks of the first administration. In some embodiments the NRS score is reduced to 1 or less. In some embodiments, the NRS score is maintained at 2 or less for longer than 2 weeks, 1 month, 2 months, 3 months, 4 months, 5 months, 6 months, 7 months, 8 months, 9 months, 10 months, 11 months or for longer than 1 year. In some embodiments, the subject remains pain free for the duration of the extension period of the study. In some embodiments, the NRS score is maintained at 2 or less for while the patient continues to receive a therapeutic dose of interleukin-1 receptor-Fc fusion protein at an administration interval and treatment period according to the invention. In some embodiments, the NRS score is maintained at 2 or less for while the patient continues to receive a therapeutic dose of interleukin-1 receptor-Fc fusion protein in absence of any concurrent therapy.

In some embodiments, administration of the interleukin-1 receptor-Fc fusion protein results in improved cardiac function, such as decreased or ameliorated pericardiac effusion, compared to a control. Pericardial effusion (also known as "fluid around the heart") is an abnormal accumulation of fluid in the pericardial cavity that is indicative of inflammation, which leads to an increased intrapericardial pressure and can negatively affect heart function. Cardiac health parameters, particularly pericardiac effusion, may be evaluated by echocardiography (ECHO), cardiac magnetic resonance imaging (MRI), and/or CT scanning. In some embodiments, administration of the interleukin-1 receptor-Fc fusion protein results in a decrease, absence or amelioration of pericardiac effusion.

A control is a reference cardiac parameter such as a reference pericardiac effusion level measured in a subject with comparable disease status but without treatment. For example, a control may be a baseline cardiac function such as a baseline pericardiac effusion measured in the subject being treated prior to the treatment. A control may also be a reference cardiac parameter such as a reference pericardiac effusion level measured in a subject with comparable disease status but treated with a placebo. In some embodiments, a control may be a reference value or graph indicative of cardiac parameters such as pericardiac effusion in a subject with comparable disease status without treatment based on historical data. In some embodiments, a control may be a reference value or graph indicative of a cardiac parameter such as pericardiac effusion in a subject with comparable disease status who receives a standard of care therapy, in absence of IL-1 receptor-Fc fusion protein administration.

In some embodiments, administration of the interleukin-1 receptor-Fc fusion protein results in improvement of cardiac parameters as indicated by ECG measurements. A reduction in the ST elevation and/or reduction in the depression after administration of the interleukin-1 receptor-Fc fusion protein is considered an improvement in the cardiac parameter.

In some embodiments, administration of the interleukin-1 receptor-Fc fusion protein results in improvement of cardiac effusion as determined by echocardiography (ECHO).

In some embodiments, administration of the interleukin-1 receptor-Fc fusion protein results in improvement of cardiac parameters as determined by CT scanning.

In some embodiments, administration of the interleukin-1 receptor-Fc fusion protein results in improvement of cardiac parameters as determined by cardiac magnetic resonance imaging (MM).

In some embodiments, administration of the interleukin-1 receptor-Fc fusion results in successful taper of steroids and other concurrent therapies, while the subject continues to receive interleukin-1 receptor-Fc fusion protein at an administration interval and treatment period according to the invention. In some embodiments, administration of the interleukin-1 receptor-Fc fusion protein results in weaning the subject of steroids and/or other concurrent therapies starting at about 4 weeks, or 5 weeks, 6 weeks, 7 weeks, 8 weeks, 9 weeks, 10 weeks, 11 weeks, 12 weeks, 14 weeks, 16 weeks, 18 weeks, 20 weeks, 22 weeks or 24 weeks after first administration, while the subject continues to receive interleukin-1 receptor-Fc fusion protein at an administration interval and treatment period according to the invention. In some embodiments, administration of the interleukin-1 receptor-Fc fusion results in a successful taper of steroids and/or other concurrent therapies which lasts for at least two weeks. In some embodiments, administration of the interleukin-1 receptor-Fc fusion results in a successful taper of steroids and other concurrent therapies that lasts for at least three weeks. In some embodiments, administration of the interleukin-1 receptor-Fc fusion results in a successful taper of steroids and other concurrent therapies that lasts for at least four weeks. In some embodiments, administration of the interleukin-1 receptor-Fc fusion results in a successful taper of steroids and other concurrent therapies that lasts for at least five weeks. In some embodiments, administration of the interleukin-1 receptor-Fc fusion results in a successful taper of steroids and other concurrent therapies that lasts for at least six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty one weeks, twenty two weeks, twenty three weeks, or twenty four weeks. In some embodiments, administration of the interleukin-1 receptor-Fc fusion results in a successful taper of steroids and other concurrent therapies that lasts for at least 6 months, 7 months, 8 months, 9 months, 10 months, 11 months, or 1 year. In some embodiments, administration of the interleukin-1 receptor-Fc fusion results in a successful taper of steroids and other concurrent therapies for more than 1 year. In some embodiments, administration of the interleukin-1 receptor-Fc fusion results in the subject being free of steroids and other concurrent therapies for greater than 1 year. In some embodiments, the subject continues to receive interleukin-1 receptor-Fc fusion protein administration at a therapeutic dose and administration interval in accordance to the invention. In some embodiments, the subject continues to receive interleukin-1 receptor-Fc fusion protein administration without any concurrent therapy.

In some embodiments, administration of the interleukin-1 receptor-Fc fusion protein results in improvement of QoL scores. Typically, QoL scores comprise one or more assessments selected from: Patient Global Impression of Pericarditis Severity (PGIPS); Physician Global Assessment of Pericarditis Activity (PGA-PA); 36-Item Short Form Health Survey (SF-36); 5-Level EuroQoL-5D (EQ-5D-5L) and Insomnia severity Index (ISI).

In some embodiments, the effectiveness of treatment using an interleukin-1 receptor-Fc fusion protein is determined by Patient Global Impression of Pericarditis Severity (PGIPS), and/or Physician Global Assessment of Pericarditis Activity (PGA-PA). The PGIPS is a single-item patient reported outcome (PRO) measure that assesses the subject's impression of overall severity of pericarditis symptoms at the time the questionnaire is administered, using a 7-point rating scale ranging from absent (no recurrent pericarditis symptoms) to very severe (recurrent pericarditis symptoms cannot be ignored). The PGA-PA is a single-item clinician-reported outcome measure that investigators use to rate their impression of the patient's overall pericarditis disease activity at the time the assessment is completed, using a 7-point rating scale ranging from absent to very severe. In some embodiments, administration of the interleukin-1 receptor-Fc fusion protein results in an improved PGIPS and/or PGA-PA compared to a control.

In some embodiments, at least 50% of the subjects undergoing treatment with interleukin-1 receptor-Fc fusion protein report an absence or minimal pericarditis symptoms as determined by PGIPS. In some embodiments, at least 75% of the subjects undergoing treatment with interleukin-1 receptor-Fc fusion protein report an absence or minimal pericarditis symptoms as determined by PGIPS. In some embodiments, at least 80% of the subjects undergoing treatment with interleukin-1 receptor-Fc fusion protein report an absence or minimal pericarditis symptoms as determined by PGIPS. In some embodiments, at least 90% of the subjects undergoing treatment with interleukin-1 receptor-Fc fusion protein report an absence or minimal pericarditis symptoms as determined by PGIPS. In some embodiments, at least 95% of the subjects undergoing treatment with interleukin-1 receptor-Fc fusion protein report an absence or minimal pericarditis symptoms as determined by PGIPS. In some embodiments, 97%, 98%, 99% or 100% of the subjects undergoing treatment with interleukin-1 receptor-Fc fusion protein report an absence or minimal pericarditis symptoms as determined by PGIPS.

In some embodiments, at least 50% of the subjects receiving interleukin-1 receptor-Fc fusion protein show an absence or minimal pericarditis symptoms as determined by PGA-PA. In some embodiments, at least 75% of the subjects undergoing treatment with interleukin-1 receptor-Fc fusion protein show an absence or minimal pericarditis symptoms as determined by PGA-PA. In some embodiments, at least 80% of the subjects undergoing treatment with interleukin-1 receptor-Fc fusion protein show an absence or minimal pericarditis symptoms as determined by PGA-PA. In some embodiments, at least 90% of the subjects undergoing treatment with interleukin-1 receptor-Fc fusion protein show an absence or minimal pericarditis symptoms as determined by PGA-PA. In some embodiments, at least 95% of the subjects undergoing treatment with interleukin-1 receptor-Fc fusion protein show an absence or minimal pericarditis symptoms as determined by PGA-PA. In some embodiments, 96%, 97%, 98%, 99% or 100% of the subjects undergoing treatment with interleukin-1 receptor-Fc fusion protein show an absence or minimal pericarditis symptoms as determined by PGA-PA.

In some embodiments, the effectiveness of the treatment using interleukin-1 receptor-Fc fusion protein is determined by a 5-Level EuroQoL-5D (EQ-5D-5L)(additional information in: www.euroqol.org). The EQ-5D-5L is a standardized instrument developed by the EuroQol Group as a measure of health-related quality of life that can be used in assessing a wide range of health conditions and treatments. The EQ-5D-5L includes a descriptive system and the EQ VAS. The descriptive system comprises 5 dimensions: mobility, self-care, usual activities, pain/discomfort and anxiety/depression. The rating scale records the subject's self-rated health on a vertical Visual Analog Scale (VAS). The scores on these 5 dimensions can be presented as a health profile or can be converted to a single summary index number (utility) reflecting preferability compared to other health profiles (euroqol.org/eq-5d-instruments).

In some embodiments, the EQ-5D-5L is collected in subjects ≥18 years or older.

In some embodiments, administration of the interleukin-1 receptor-Fc fusion protein results in an improved EQ-5D-5L. In some embodiments, at least 50% of the subjects receiving interleukin-1 receptor-Fc fusion protein show a clinical relevant improved EQ-5D-5L score. In some embodiments, at least 75% of the subjects undergoing treatment with interleukin-1 receptor-Fc fusion protein show a clinical relevant improved EQ-5D-5L score. In some embodiments, at least 80% of the subjects undergoing treatment with interleukin-1 receptor-Fc fusion protein show a clinical relevant improved EQ-5D-5L score. In some embodiments, at least 90% of the subjects undergoing treatment with interleukin-1 receptor-Fc fusion protein show a clinical relevant improved EQ-5D-5L score. In some embodiments, at least 95% of the subjects undergoing treatment with interleukin-1 receptor-Fc fusion protein show a clinical relevant improved EQ-5D-5L score. In some embodiments, 96%, 97%, 98%, 99% or 100% of the subjects undergoing treatment with interleukin-1 receptor-Fc fusion protein a clinical relevant improved EQ-5D-5L score.

In some embodiments, a control for a QoL measurements indicated in the preceding sections, is a baseline QoL scores determined in the subject prior to the treatment. In some embodiments, a control is reference QoL scores in a subject with comparable disease status but treated with a placebo. In some embodiments, a control is a reference indicative of QoL scores in a subject with comparable disease status without treatment. In some embodiments, a control is indicative of the QoL when a subject having the disease receives a standard of care therapy, in absence of IL-1 receptor-Fc fusion protein administration.

In some embodiments, administration of the interleukin-1 receptor-Fc fusion results in an improved Insomnia Severity Index (ISI). The ISI is a 7-item self-report questionnaire assessing the nature, severity, and impact of insomnia. The usual recall period is the "last 2 weeks" and the dimensions evaluated are severity of sleep onset, sleep maintenance, early morning awakening problems, sleep dissatisfaction, interference of sleep difficulties with daytime functioning, noticeability of sleep problems by others, and distress caused by the sleep difficulties. A 5-point Likert scale is used to rate each item (e.g., 0=no problem; 4=very severe problem), yielding a total score ranging from 0 to 28. The total score is interpreted as follows: no clinically significant insomnia (0-7); subthreshold insomnia (8-14); clinical (moderate) insomnia (15-21); and clinical (severe) insomnia (22-28) (Morin et al., Sleep. 2011; 34(5):601-608). In some embodiments, the ISI is collected in subjects ≥18 years or older. In some embodiments, the ISI in a subject after administration of an interleukin-1 receptor-Fc fusion is improved to less than 14, or between 8-14, or less than 7. In some embodiments, administration of the interleukin-1 receptor-Fc fusion results in the ISI of less than or equal to 7 in the subject being treated. In some embodiments, ISI score is less than or equal to 7 in at least 50% of the subjects who receive interleukin-1 receptor-Fc fusion protein. In some embodiments, ISI score is less than or equal to 7 in at least 75% of the subjects who receive interleukin-1 receptor-Fc fusion protein. In some embodiments, ISI score is less than or equal to 7 in at least 80%, 90%, 95%, 96%, 97%, 98%, 99% or 100% of the subjects who receive interleukin-1 receptor-Fc fusion protein.

In some embodiments, the effectiveness of treatment with an interleukin-1 receptor-Fc fusion protein is determined by a reduced risk of pericarditis recurrence compared to a no-treatment or placebo control. In some embodiments, administration of the interleukin-1 receptor-Fc fusion results in reduced risk of pericarditis recurrence of less than 50%, less than 40%, less than 30%, less than 20%, less than 10%, less than 5%, less than 2%, or less than 1% or less than 0.5% or less than 0.25% or less than 0.1% based on statistical analysis of patients population being treated with an interleukin-1 receptor-Fc fusion protein according to the present invention.

In some embodiments, the effectiveness of treatment with an interleukin-1 receptor-Fc fusion protein is determined by a recurrence-free period during or subsequent to the treatment. A recurrence-free period of survival typically means that the subject does not experience an episode or occurrence of one or more symptoms of pericarditis or a flare of inflammation during the period. A pericarditis recurrence or flare is usually indicated by any one or more of the following: an increase in the CRP level of ≥1 mg/dl in peripheral blood; or an increase in pain, determined in an NRS scale of ≥4; or occurrence of pericardial effusion (e.g., as determined by ECG or ECHO); a pericardial rub; or fever or any other symptomatic indication of the pericardial disease (e.g., as determined by PGIPS, PGA-PA, SF-36, EQ-5D-5L, or ISI). In some embodiments, a subject continues to receive a therapeutic dose of interleukin-1 receptor-Fc fusion protein at an administrative interval and treatment period in accordance to the invention during the recurrence-free period. In some embodiments, a subject may be gradually weaned of interleukin-1 receptor-Fc fusion protein treatment during the recurrence-free period.

In some embodiments, the effectiveness of treatment with an interleukin 1 receptor-Fc fusion protein is determined by the time period of recurrence-free survival (for examples, Days to flare). In some embodiments, the recurrence-free survival period is at least 30 days, 40 days, 50 days, 60 days, 70 days, 80 days, or 90 days from the first administration of the interleukin-1 receptor-Fc fusion protein. In some embodiments, the recurrence-free survival period is at least 91 days, 92 days, 93 days, 94 days, 95 days, 96 days, 97 days, 98 days, 99 days, 100 days from the first administration of the interleukin-1 receptor-Fc fusion protein. In some embodiments, the recurrence-free survival period is at least 105 days, or at least 110 days, or at least 115 days, or at least 120 days, or at least 130 days, or at least 140 days, or at least 150 days. In some embodiments, the recurrence-free survival period is at least 200 days or more, while receiving interleukin 1 receptor-Fc fusion protein at an administration interval (e.g., a weekly dose) and treatment period according to the invention.

In some embodiments, the recurrence-free survival period is at least 30 days, 40 days, 50 days, 60 days, 70 days, or at least 80 days from the withdrawal of a pain medicine, or NSAID, while receiving weekly dose of the interleukin 1 receptor-Fc fusion protein. In some embodiments, the recurrence-free survival period from the withdrawal of NSAID is at least 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 110 days, 120 days, 130 days, 140 days, 150 days, 160 days, 170 days, 180 days, 190 days or 200 days or more, while receiving interleukin 1 receptor-Fc fusion protein at an administration interval (e.g., a weekly dose) and treatment period according to the invention.

In some embodiments, the recurrence-free survival period is at least 50 days from the withdrawal of a corticosteroid, while receiving weekly dose of interleukin 1 receptor-Fc fusion protein. In some embodiments the flare-free survival period from the withdrawal of NSAID is at least 55 days, 60 days, 65 days, 70 days, 75 days, 80 days, 85 days, 90 days, 95 days, 100 days, 110 days, 120 days, 130 days, 140 days, 150 days, 160 days, 170 days, 180 days, 190 days or 200 days or more, while receiving interleukin 1 receptor-Fc fusion protein at an administration interval (e.g., a weekly dose) and treatment period according to the invention.

Adverse Effects

Adverse effects related to the treatment of pericarditis can include injection-site reaction, upper respiratory tract infection, headache, nausea, vomiting, diarrhea, sinusitis, arthralgia, flu-like symptoms, abdominal pain, pyrexia, herpes, transaminase elevation, ischemic optic neuropathy and nasopharyngitis.

In some embodiments, administration of an interleukin-1 receptor-Fc fusion protein results in no serious adverse events in the subject. In some embodiments, administration of an interleukin-1 receptor-Fc fusion protein does not result in one or more of injection-site reaction, worsening of rheumatoid arthritis, upper respiratory tract infection, headache, nausea, vomiting, diarrhea, sinusitis, ischemic optic neuropathy, arthralgia, flu-like symptoms, abdominal pain, pyrexia, herpes, transaminase elevation and nasopharyngitis.

In some embodiments, the various safety assessments include pharmacokinetic and pharmacodynamic monitoring, including but not limited to: physical examination, measurement of vital signs, monitoring adverse event (AE), monitoring chest X-ray and screening for signs of tuberculosis.

Interleukin-1 (IL-1) Receptor-Fc Fusion Proteins

In some embodiments, inventive compositions and methods provided by the present invention are used to deliver an interleukin-1 receptor-Fc fusion protein to a subject in need. In certain embodiments of the invention, the interleukin-1 receptor-Fc fusion proteins are recombinant fusion proteins that block IL-1 signaling by acting as a soluble decoy receptor that binds IL-1α and IL-1β (i.e., an IL-1 trap) and prevents their interaction with IL-1 cell surface receptors. In certain embodiments, the fusion protein comprises human cytokine receptor extracellular domains and an Fc portion of human immunoglobulin. In some embodiments, the Fc portion is from a human IgG1, IgG2, or IgG4. In some embodiments, the Fc portion comprises CH2 and CH3 domains derived from a human IgG1, IgG2 or IgG4. In one embodiment, the Fc portion comprises a CH2 domain derived from a human IgG4 and a CH3 domain derived from a human IgG1. In some embodiments, the Fc portion comprises at least a portion of the hinge region derived from a human IgG1. In some embodiments, the fusion protein comprises the extracellular domains of IL-1R Type 1 and IL-1R accessory protein (IL-1RAcP). In some embodiments, two identical fusion proteins comprising the extracellular domains of IL1R Type 1 and IL-1RAcP and an Fc portion of human IgG1 are covalently linked by disulfide bonds in the Fc region to form a homodimer. In one embodiment, the interleukin-1 receptor-Fc fusion protein is rilonacept.

```
Interleukin-1 Receptor-Fc Fusion Protein Sequence
                                                    (SEQ ID NO: 1)
SERCDDWGLDTMRQIQVFEDEPARIKCPLFEHFLKFNYSTAHSAGLTLIW

YWTRQDRDLEEPINFRLPENRISKEKDVLWFRPTLLNDTGNYTCMLRNTTYCSKVAFPL

EVVQKDSCFNSPMKLPVHKLYIEYGIQRITCPNVDGYFPSSVKPTITWYMGCYKIQNFNN

VIPEGMNLSFLIALISNNGNYTCVVTYPENGRTFHLTRTLTVKVVGSPKNAVPPVIHSPN

DHVVYEKEPGEELLIPCTVYFSFLMDSRNEVWWTIDGKKPDDITIDVTINESISHSRTEDE

TRTQILSIKKVTSEDLKRSYVCHARSAKGEVAKAAKVKQKVPAPRYTVEKCKEREEKIIL

VSSANEIDVRPCPLNPNEHKGTITWYKDDSKTPVSTEQASRIHQHKEKLWFVPAKVEDS

GHYYCVVRNSSYCLRIKISAKFVENEPNLCYNAQAIFKQKLPVAGDGGLVCPYMEFFKN

ENNELPKLQWYKDCKPLLLDNIHFSGVKDRLIVMNVAEKHRGNYTCHASYTYLGKQYP

ITRVIEFITLEENKPTRPVIVSPANETMEVDLGSQIQLICNVTGQLSDIAYWKWNGSVIDE

DDPVLGEDYYSVENPANKRRSTLITVLNISEIESRFYKHPFTCFAKNTHGIDAAYIQLIYP

VTNSGDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSPGK

Interleukin-1 Receptor-Fc Fusion Protein Sequence with
N-Terminus Signal Sequence
                                                    (SEQ ID NO: 2)
MVLLWCVVSLYFYGILQSDASERCDDWGLDTMRQIQVFEDEPARIKCPLF

EHFLKFNYSTAHSAGLTLIWYWTRQDRDLEEPINFRLPENRISKEKDVLWFRPTLLNDTG

NYTCMLRNTTYCSKVAFPLEVVQKDSCFNSPMKLPVHKLYIEYGIQRITCPNVDGYFPSS

VKPTITWYMGCYKIQNFNNVIPEGMNLSFLIALISNNGNYTCVVTYPENGRTFHLTRTLT

VKVVGSPKNAVPPVIHSPNDHVVYEKEPGEELLIPCTVYFSFLMDSRNEVWWTIDGKKP

DDITIDVTINESISHSRTEDETRTQILSIKKVTSEDLKRSYVCHARSAKGEVAKAAKVKQK

VPAPRYTVEKCKEREEKIILVSSANEIDVRPCPLNPNEHKGTITWYKDDSKTPVSTEQAS

RIHQHKEKLWFVPAKVEDSGHYYCVVRNSSYCLRIKISAKFVENEPNLCYNAQAIFKQK

LPVAGDGGLVCPYMEFFKNENNELPKLQWYKDCKPLLLDNIHFSGVKDRLIVMNVAEK
```

```
-continued
HRGNYTCHASYTYLGKQYPITRVIEFITLEENKPTRPVIVSPANETMEVDLGSQIQLICNV

TGQLSDIAYWKWNGSVIDEDDPVLGEDYYSVENPANKRRSTLITVLNISETESRFYKHPF

TCFAKNTHGIDAAYIQLIYPVTNSGDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEA

LHNHYTQKSLSLSPGK

Extracellular Domain of IL-1RAcP Amino Acid Sequence
                                                    (SEQ ID NO: 3)
SERCDDWGLDTMRQIQVFEDEPARIKCPLFEHFLKFNYSTAHSAGLTLIW

YWTRQDRDLEEPINFRLPENRISKEKDVLWFRPTLLNDTGNYTCMLRNTTYCSKVAFPL

EVVQKDSCFNSPMKLPVHKLYIEYGIQRITCPNVDGYFPSSVKPTITWYMGCYKIQNFNN

VIPEGMNLSFLIALISNNGNYTCVVTYPENGRTFHLTRTLTVKVVGSPKNAVPPVIHSPN

DHVVYEKEPGEELLIPCTVYFSFLMDSRNEVWWTIDGKKPDDITIDVTINESISHSRTEDE

TRTQILSIKKVTSEDLKRSYVCHARSAKGEVAKAAKVKQKVPAPRYTVE

Extracellular Domain of IL-1R1 Amino Acid Sequence
                                                    (SEQ ID NO: 4)
KCKEREEKIILVSSANEIDVRPCPLNPNEHKGTITWYKDDSKTPVSTEQAS

RIHQHKEKLWFVPAKVEDSGHYYCVVRNSSYCLRIKISAKFVENEPNLCYNAQAIFKQK

LPVAGDGGLVCPYMEFFKNENNELPKLQWYKDCKPLLLDNIHFSGVKDRLIVMNVAEK

HRGNYTCHASYTYLGKQYPITRVIEFITLEENKPTRPVIVSPANETMEVDLGSQIQLICNV

TGQLSDIAYWKWNGSVIDEDDPVLGEDYYSVENPANKRRSTLITVLNISETESRFYKHPF

TCFAKNTHGIDAAYIQLIYPVTN

Fc (IgG1) Amino Acid Sequence
                                                    (SEQ ID NO: 5)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPGK
```

In some embodiments of the invention, an interleukin-1 receptor-Fc fusion protein comprises an amino acid sequence of SEQ ID NO: 1. In some embodiments of the invention, an interleukin-1 receptor-Fc fusion protein comprises an amino acid sequence of SEQ ID NO: 2. In some embodiments of the invention, an interleukin-1 receptor-Fc fusion protein comprises an amino acid sequence at least 90% identical SEQ ID NO: 1. In some embodiments of the invention, an interleukin-1 receptor-Fc fusion protein comprises an amino acid sequence with at least 75%, 80%, 85%, 90%, 91%, 92%, 93%, 94%, 95%, 96%, 97%, 98%, 99% or more identity to SEQ ID NO: 1.

In some embodiments of the invention, an interleukin-1 receptor-Fc fusion protein comprises an amino acid sequence with at least 75%, 80%, 85%, 90%, 91%, 92%, 93%, 94%, 95%, 96%, 97%, 98%, 99% or more identity to SEQ ID NO: 3. In some embodiments of the invention, an interleukin-1 receptor-Fc fusion protein comprises an amino acid sequence with at least 75%, 80%, 85%, 90%, 91%, 92%, 93%, 94%, 95%, 96%, 97%, 98%, 99% or more identity to SEQ ID NO: 4. In some embodiments of the invention, an interleukin-1 receptor-Fc fusion protein comprises an amino acid sequence with at least 75%, 80%, 85%, 90%, 91%, 92%, 93%, 94%, 95%, 96%, 97%, 98%, 99% or more identity to SEQ ID NO: 5.

The invention contemplates treatment of pericarditis using an agent capable of reducing interleukin 1 receptor engagement, activity or expression, thereby achieving the biological effect comparable to the interleukin-1 receptor-Fc fusion protein treatment. In some aspects, the pericarditis is related to PCIS. In some aspects, the pericarditis is related to PPS. In some embodiments, the agent capable of reducing interleukin receptor engagement is an interleukin-1 antagonist. In some embodiments, the invention provides a method of treating PCIS or PPS pericarditis by administering to the subject in need a therapeutically effective amount of an interleukin-1 antagonist at a suitable administration interval for a period as to improve, stabilize or decrease at least one or more symptoms associated with the disease. In some embodiments, the interleukin-1 antagonist is an interleukin-1 binding protein. In some embodiments, the interleukin-1 antagonist is a receptor for interleukin-1 or a fragment thereof. In some embodiments, the interleukin-1 antagonist is an antibody or a fragment thereof. In some embodiments, the interleukin-1 antagonist is an interleukin-1 receptor fusion protein. In some embodiments the agent is an interleukin-1 receptor antagonist (IL-1ra).

As is easily comprehensible by one of skill in the art, the agent can be an IL-1 receptor blocking antibody or fragment thereof, an IL-1 antigen-binding protein, an IL-1 antibody or a fragment thereof, an antagonist of IL-1 receptor, an inhibitor of IL-1 receptor, an inhibitor of IL-1 receptor activation, an inhibitor of the IL-1 receptor mediated signaling, an inhibitor peptide capable of blocking IL-1 receptor signaling, an inhibitor peptide capable of blocking or otherwise reducing IL-1 interaction with IL-1 receptor, an inhibitor RNA or nucleic acid which reduces the expression of an IL-1 receptor ligand or an IL-1 receptor. The present disclosure therefore encompasses obvious variants of the invention that achieves the same purpose by using one or more of conventional methods known to one of skill in the art to target IL-1 receptor activation pathway for treating pericarditis.

EXAMPLES

While certain methods of the present invention have been described with specificity in accordance with certain embodiments, the following examples serve only to illustrate the methods of the invention and are not intended to limit the same.

Example 1: Treatment of Pericarditis with IL-1 Receptor-Fc Fusion Protein

The study in this example was a Phase II clinical trial designed to evaluate the safety, tolerability, and PK of rilonacept, an interleukin-1 receptor-Fc fusion protein, in subjects with pericarditis. The study also included exploratory investigations of the effect of the interleukin-1 receptor-Fc fusion protein on clinical effect assessments in symptomatic patients.

Rilonacept is a recombinant fusion protein including the extracellular domains of human IL-1 cytokine receptor and the Fc portion of human immunoglobulin G1 (IgG1) (SEQ ID NO:1). It acts as a soluble decoy receptor binding IL 1α/IL 1β and prevents their interaction with the IL 1 cell surface receptor.

Study drug (rilonacept or placebo) is supplied in a single use, 20 ml glass vial containing a sterile, white to off white, lyophilized powder. Each vial is to be reconstituted with 2.3 ml sterile Water for Injection (WFI). A volume up to 2 ml can be withdrawn, which is designated to deliver up to 160 mg of rilonacept or up to 2 ml of placebo for SC injection only. The resulting solution is clear, colorless to pale yellow, and essentially free of particulates.

Each rilonacept vial contains 220 mg of rilonacept lyophilized powder. After reconstitution with 2.3 ml WFI, the rilonacept vial contains 80 mg/ml rilonacept, 40 mM histidine, 50 mM arginine, 3.0% (w/v) polyethylene glycol 3350, 2.0% (w/v) sucrose, and 1.0% (w/v) glycine at a pH of 6.5. No preservatives are present.

Study Design

Participating subjects receive a total of 6 weekly doses of the interleukin-1 receptor-Fc fusion protein. Dosing is initiated with a loading dose of 320 mg administered subcutaneously as two 160 mg doses, followed by 160 mg maintenance doses administered subcutaneously once a week. Pericarditis improvement data and safety information are collected. If subjects are deemed to be responsive to treatment, participation in an optional 18 week extension period may be offered. For the duration of the Treatment Period, concomitant NSAIDs and/or colchicine and/or corticosteroids, if present, should be continued at pre-study dose levels until after the 6 dose Treatment Period has concluded; however, should if it is determined that a reduction/tapering of the NSAID, colchicine, and/or corticosteroid dose is medically indicated, the NSAID, colchicine, and/or corticosteroid dose can be down-titrated.

Opioid analgesics, non-narcotic analgesics (e.g., tramadol), and acetaminophen are allowed as rescue medication for ancillary pain control on an as-needed basis throughout the Treatment Period. Although it is recommended that NSAID dose levels (if present) should remain constant during the active Treatment Period, the concomitant NSAID dose may be temporarily increased (or an NSAID initiated) for ancillary pain control if deemed necessary. At the discretion of the Investigator, "Treatment Responders" (defined by the investigator as a clinically significant reduction in pericardial pain using the 11-point NRS, normal or near-normal CRP levels, and/or absent or decreasing echocardiographic effusion at the End-of-Trial Visit), will be offered participation in an optional 18-week Extension Period (EP), in which weekly administration of interleukin-1 receptor-Fc fusion protein can be continued at the same dose as in the Treatment Period for a total duration of treatment of up to 24 weeks. During the EP, the Investigator may choose to wean concomitant NSAIDs, colchicine, and/or corticosteroids according to standard of care paradigms.

Study Treatments

The interleukin-1 receptor-Fc fusion protein was prepared as a lyophilized formulation. For subcutaneous (SC) administration, the interleukin-1 receptor-Fc fusion protein was manufactured in a dosage form containing 160 mg per vial. The lyophilized powder was reconstituted with 2.3 mL of sterile Water for Injection (WFI) and drug was delivered in 2 mL at a concentration of 80 mg/mL. Dosing initiated with a loading dose of 320 mg administered subcutaneously as two 160 mg doses, followed by 160 mg maintenance doses were administered subcutaneously once a week. After an initial group of subjects were treated, depending on the safety profile observed as well as the magnitude and speed of treatment response (e.g., if an informative number of subjects achieve treatment responded early in the Treatment Period), the protocols allows for the dose administered to a subsequent group of subjects to be decreased to loading dose of 160 mg (2×80 mg) administered SC, followed by 80 mg maintenance dose administered SC once a week for 5 additional weeks, in order to determine efficacy at a lower dose.

Subject Inclusion Criteria

Subjects who have had an index episode of pericarditis which, based on the available data, met the criteria for an acute pericarditis event, using the 2015 ESC Guidelines for the Diagnosis and Management of Pericardial Diseases (Adler et al, European Heart Journal, Volume 36, issue 42, 7 Nov. 2015, Pages 2921-2964) as a frame of reference—i.e., met at least 2 of the 4 following criteria: pericarditic chest pain, pericardial rubs, new widespread ST-segment elevation or PR-segment depression on ECG, and pericardial effusion (new or worsening). Additional supporting findings included elevations of markers of inflammation (i.e., CRP, erythrocyte sedimentation rate, and white blood cell count) or evidence of pericardial inflammation by an imaging technique (e.g., MRI).

Subjects also had to have had at least one prior recurrent episode of pericarditis, and subjects had to have an ongoing symptomatic episode of pericarditis at the time of study enrollment, both based upon the available diagnostic information. Also, if a subject used NSAIDs, and/or colchicine and/or corticosteroids (in any combination), they must have received at stable dose levels for at least 7 days prior to initial dosing (although stable doses for at least 3 days were acceptable if a shorter period of stability was not anticipated to alter the baseline CRP values) with the interleukin-1 receptor-Fc fusion protein and the subject was expected to continue these concomitant medications at these dose levels for the duration of the active Treatment Period.

The phase 2 open-label pilot study is a 24-week study in up to 40 subjects in total, age 6 to 75 years old, including the following categories of subjects with recurrent pericarditis, referred as the following Groups:

Group 1 enrolling symptomatic subjects with recurrent idiopathic pericarditis (RIP) with an elevated marker of systemic inflammation (C-reactive protein [CRP]≥1 mg/dL);

Group 2 enrolling symptomatic subjects with RIP with CRP<1 mg/dL which, in the opinion of the investigator could be attributed to concomitant medications (e.g., corticosteroids) and with pericardial inflammation present on cardiac magnetic resonance imaging (MM), confirmed by the imaging core lab;

Group 3 enrolling subjects with corticosteroid-dependent RIP not experiencing symptoms which would meet the diagnostic criteria for a flare of pericarditis;

Group 4 enrolling symptomatic subjects with recurrent post pericardiotomy syndrome (PPS) with an elevated marker of systemic inflammation (CRP≥1 mg/dL); and Group 5 enrolling subjects with corticosteroid-dependent recurrent PPS not experiencing symptoms which would meet the diagnostic criteria for a flare of pericarditis.

Study Assessments

Blood samples were collected and C-reactive protein (CRP) levels were determined both before study inclusion of a subject and during the study. Some subjects presented with elevated CRP values ≥1 mg/dL at the time of study enrollment. CRP changes and the time course to decrease and resolution of CRP to normal values <0.5 mg/dL were assessed.

The following clinical response assessments were also conducted during the study.

Echocardiograms (ECHOS) including assessment of pericardial effusion were performed at screening (SCV1); at Study Site/Clinic visits during the Treatment Period (Interval Evaluation Visit, which, if applicable, occurred during approximately weeks 3-4 of the Treatment Period and Visit 7/End-of-Trial); at the Interval Evaluation Visit during the EP [if applicable]; and at the Final Study Visit/Visit 8 (SCV8). Pericardial effusion was characterized by accumulation of excess fluid in the pericardial space surrounding the heart and was one of the common features of pericarditis. Echocardiography is a sensitive tool and the most widely used imaging technique for the detection of pericardial effusion and/or thickening. For the purposes of the analysis of treatment response in all subjects at the end of the study, all ECHO images were assessed by a central reader.

Twelve-lead electrocardiograms (ECGs) were performed at screening (SCV1 and optional SCV2), at Study Site/Clinic visits during the Treatment Period (Interval Evaluation Visit [if applicable] and Visit 7/End-of-Trial), at the Interval Evaluation Visit during the Extension Period (EP) [if applicable], and at the Final Study Visit/Visit 8. Pericarditis commonly involves changes in the electrophysiologic activity of the heart, resulting in typical ECG findings, namely widespread ST-elevation or PR depression. Changes in ECG findings help determine the pericarditis status of a subject. For the purposes of the analysis of treatment response in all subjects at the end of the study, all ECG tracings were assessed by a central reader.

Common pericarditis signs include fever and pericardial rub. These pericarditis signs were assessed via documentation of vital signs and physical examinations. Physical examinations and vital signs assessments for pericarditis signs were performed at screening (SCV1 and optional SCV2), at Study Site/Clinic visits during the Treatment Period (Interval Evaluation Visit [if applicable] and Visit 7/End-of-Trial), at the Interval Evaluation Visit during the EP [if applicable], and the Final Study Visit/Visit 8. If applicable, assessment of pericarditis signs were also performed at unscheduled visits.

Common pericarditis symptoms include chest discomfort (pericarditis pain). A validated 11-point Numerical Rating Scale (NRS) was used to measure the subject's level of pericarditis (chest) pain intensity (Mannion et al, Nature Clinical Practice Rheumatology 2007; 3 (11): 610-18). The assessment was performed at all study visits on-site during Study Site/Clinic visits and as part of telephone calls/virtual visits during outpatient visits/treatment weeks (weekly during the Treatment Period and monthly during the EP).

Cardiac MRI was an optional assessment and could be performed at study entry (SCV1) and at the final study visit (Visit 8) to assess any changes in pericardial inflammation. For the purposes of the analysis of treatment response in all subjects at the end of the study, all cardiac Mill images was to be assessed by a central reader.

A validated Quality of Life Questionnaires was used to assess changes in the subject's overall well-being (Hays et al, Qual Life Res (2009) 18:873-880). The patient's global assessment was performed at screening (SCV1), at Visit 1 (Day 0), at the end of the Treatment Period (Visit 7/End-of-Trial), at the Interval Evaluation Visit during the EP, and at the Final Visit (Visit 8).

An adverse event (AE) is any untoward medical occurrence in a subject or clinical investigation subject administered a pharmaceutical product. An AE does not necessarily have a causal relationship with this treatment. An AE can therefore be any unfavorable and/or unintended sign (including an abnormal laboratory finding), symptom or disease temporally associated with the use of a medicinal (investigational) product, whether or not related to the medicinal (investigational) product.

AEs also include: any worsening (i.e., any clinically significant change in frequency and/or intensity) of a pre-existing condition that is temporally associated with the use of the interleukin-1 receptor-Fc fusion protein; abnormal laboratory findings considered by the reporting investigator to be clinically significant; and any untoward medical occurrence.

In this study, individual elements of pericarditis symptomatology (including pain) are captured as an efficacy parameter. Pericarditis pain is not required to be reported as an AE. However, if the subject experiences new symptoms that had not been previously reported in the constellation of symptoms recorded at baseline, these new symptoms should be reported as an adverse event.

Primary efficacy endpoints include inter- and intra-subject variability estimates for CRP and the 11-point NRS instrument in symptomatic subjects with RIP both at baseline and while on the interleukin-1 receptor-Fc fusion protein treatment. Exploratory endpoints include the following: time course of improvement of measures of pericarditis symptomatology, including pericarditis pain, CRP, and/or resolution of echocardiographic and ECG abnormalities; differential response to different interleukin-1 receptor-Fc fusion protein doses (e.g., 160 mg or 80 mg maintenance doses); time to CRP normalization (≤0.5 mg/dL); change over time in CRP levels; number (percentage) of subjects with normalization of CRP; change over time in subjects' assessments of pericarditis pain; explore Patient-Reported Outcome (PRO), biochemical (CRP), and imaging correlates of clinical improvement of pericarditis symptomatology in order to develop a suitable composite primary endpoint for subsequent clinical trials in RIP; number (percentage) of subjects with pericarditis improvement (based on investigator assessment); change over time in subjects' global assessments of overall well-being (using the QoL instrument); change in pericardial inflammation as assessed by cardiac MRI; number of subjects weaned off NSAIDs, colchicine, and/or corticosteroids at end of the EP; time to pericardial flare, the number of patients experiencing recurrence of pericarditis and the number of recurrences of pericarditis.

Example 2: Reduction in CRP Levels and Pain with Interleukin-1 Receptor-Fc Fusion Protein This example demonstrates that the Phase II clinical trial described in Example 1 resulted in clinically meaningful efficacy, particularly clinically significant reduction in CRP levels and pain.

Figure 1B:
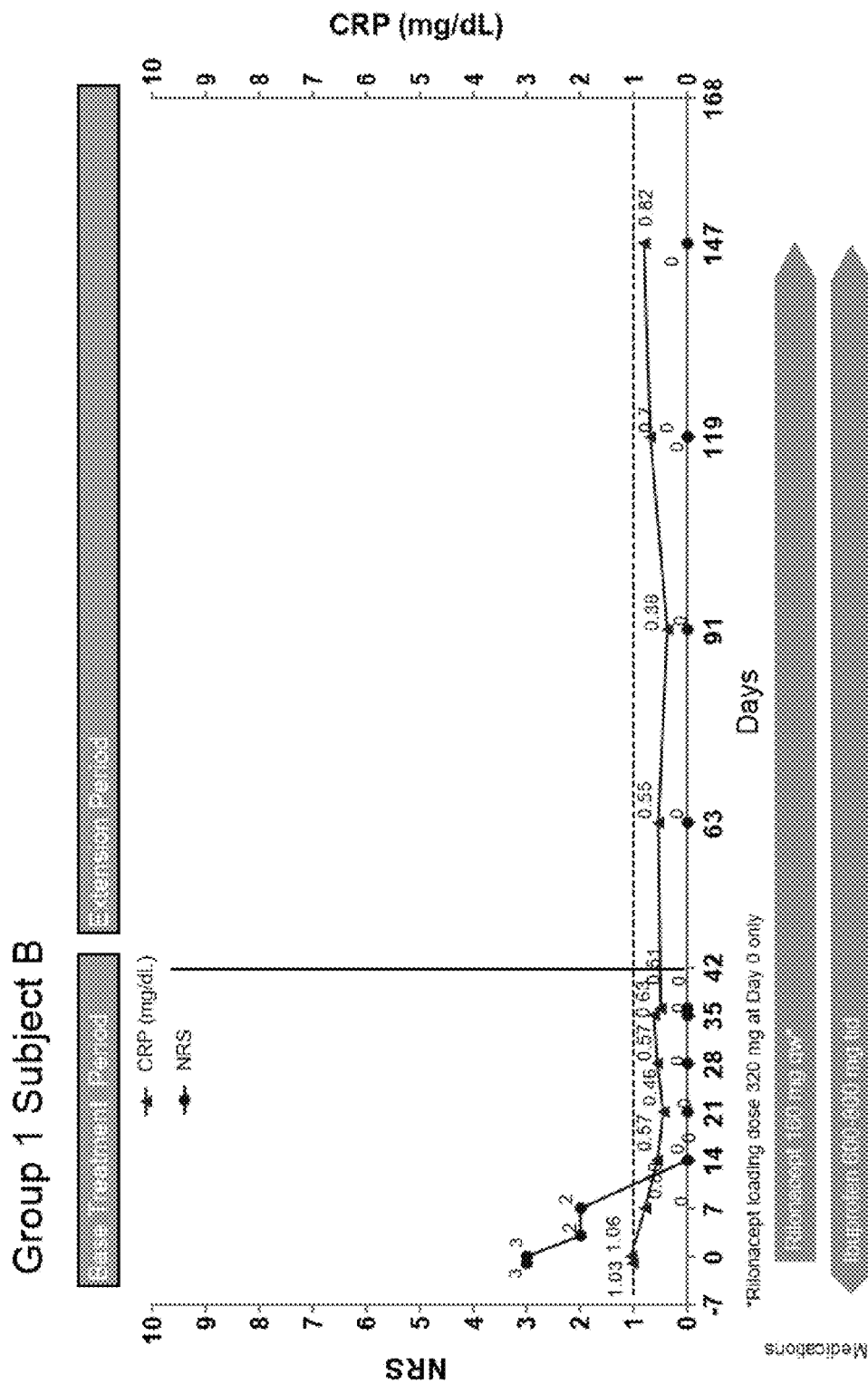
Figure 1C:
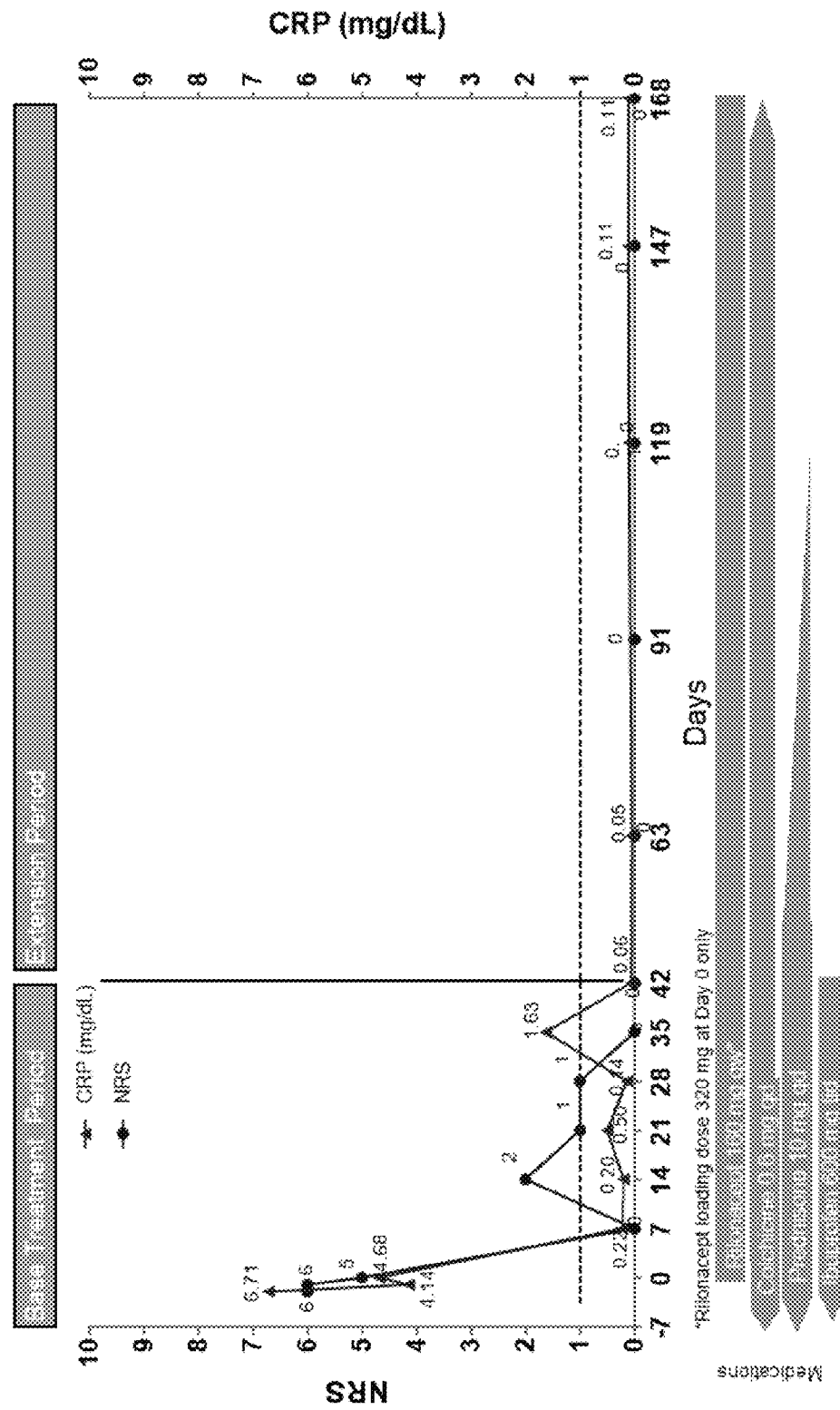
Figure 1D:
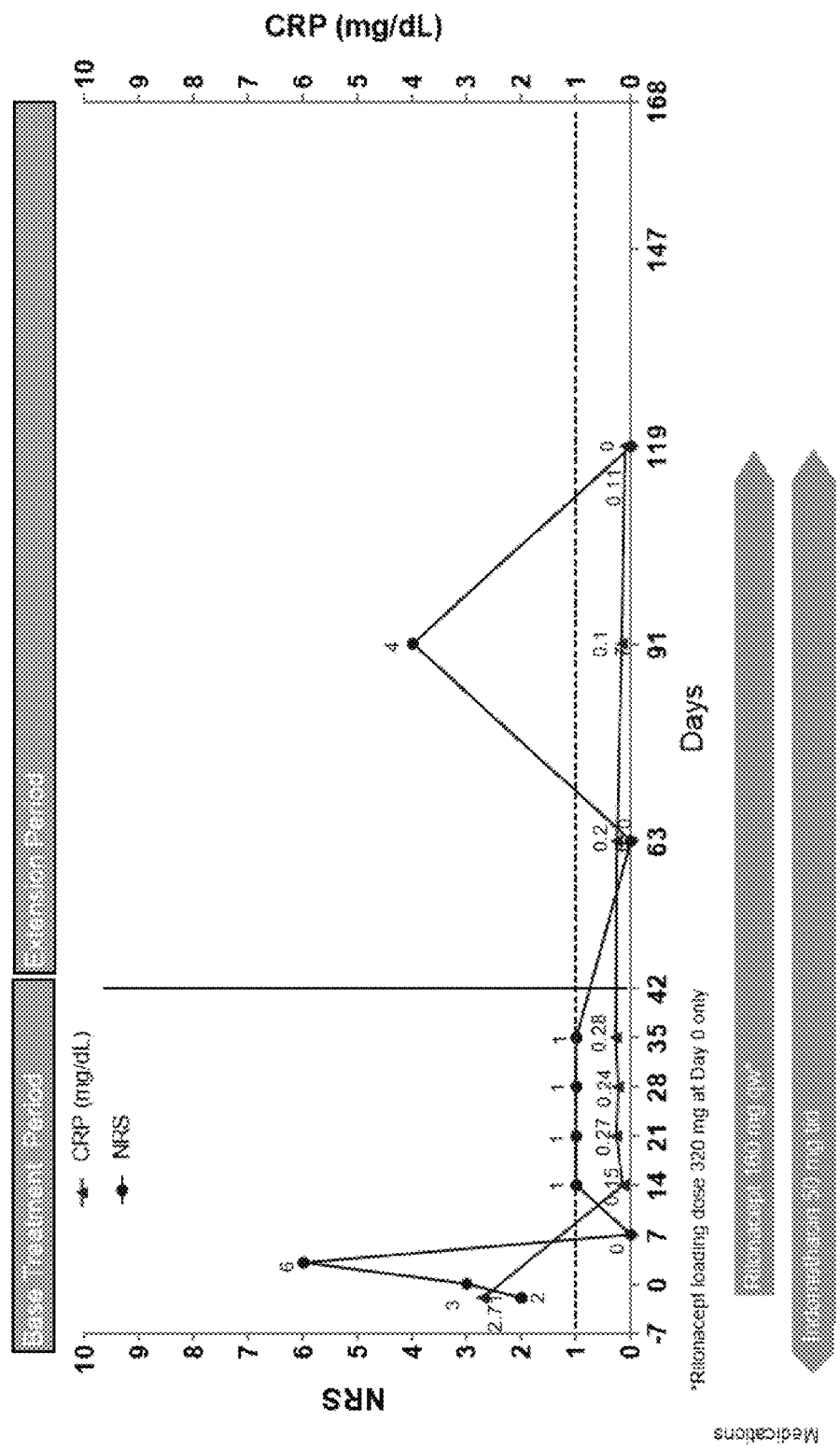
Figure 1E:
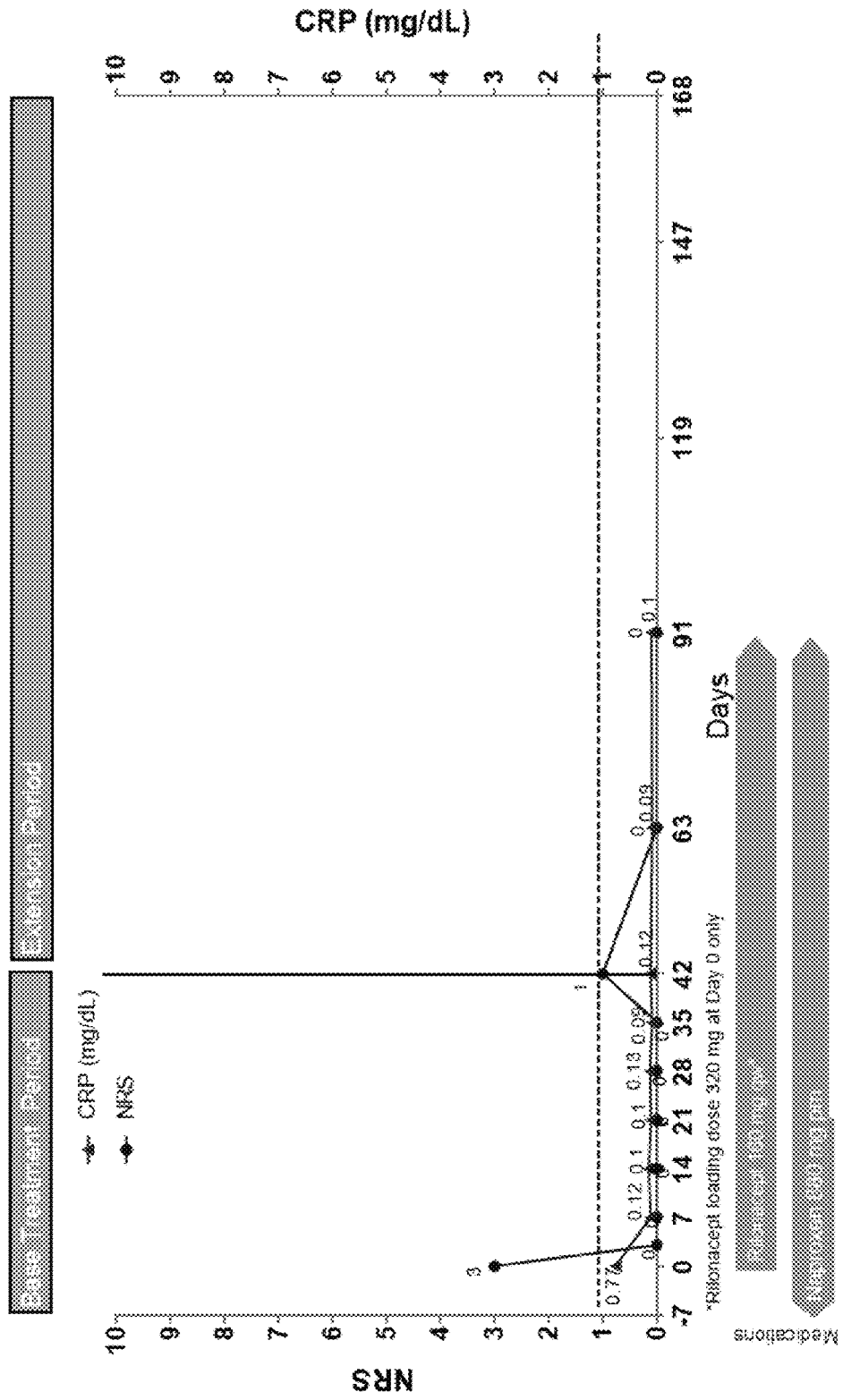
Figure 1F:
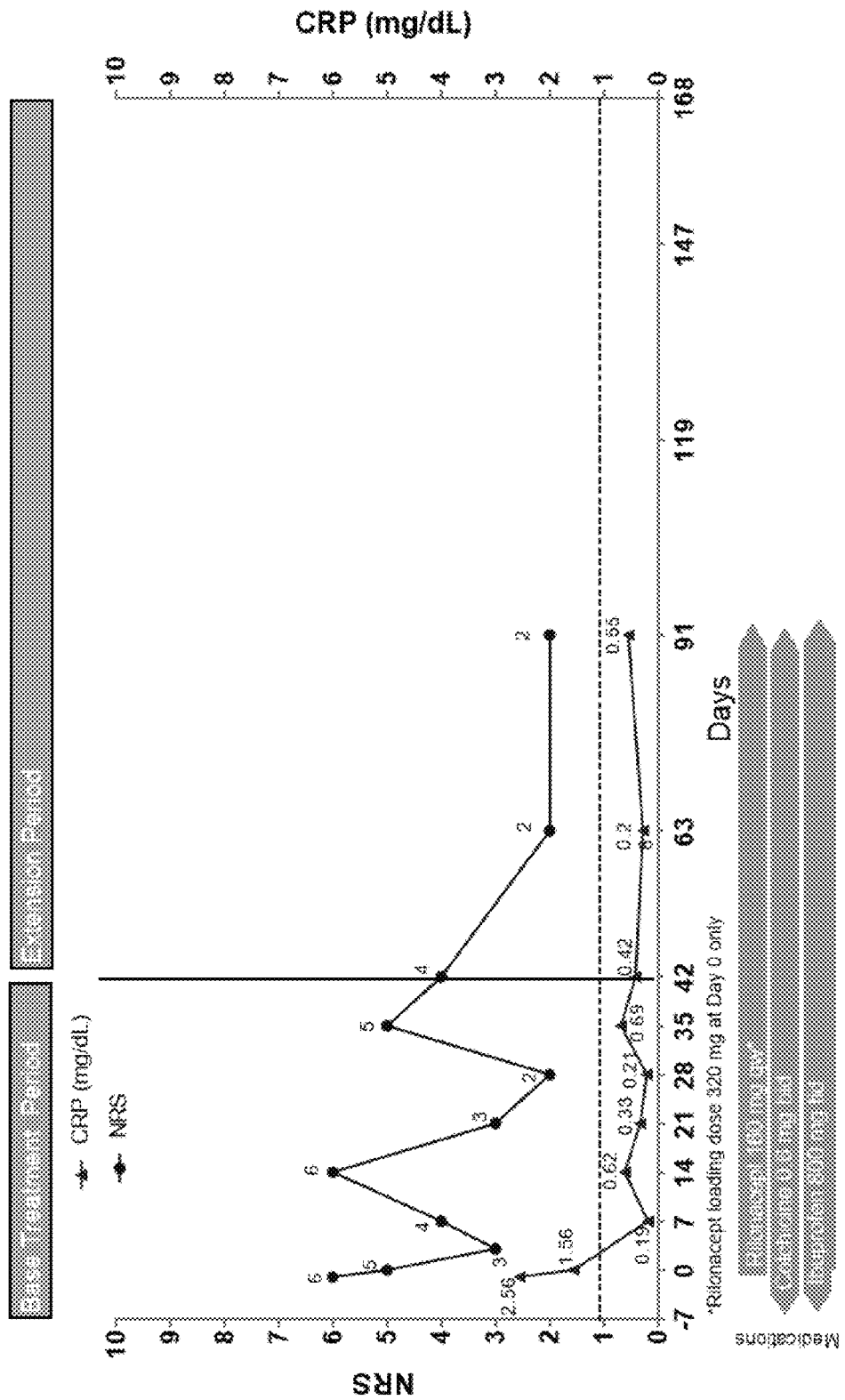
Figure 1G:
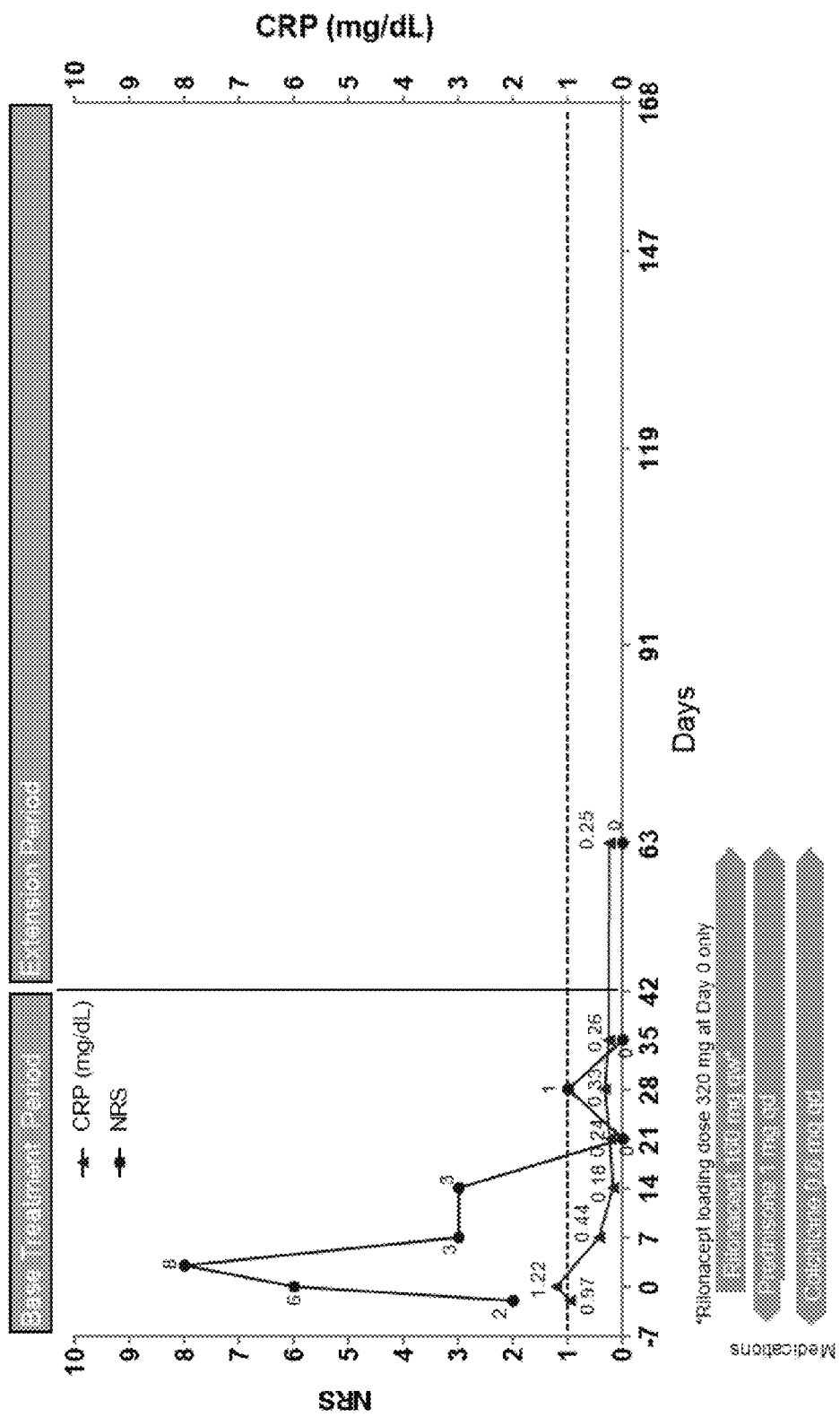
Figure 1H:
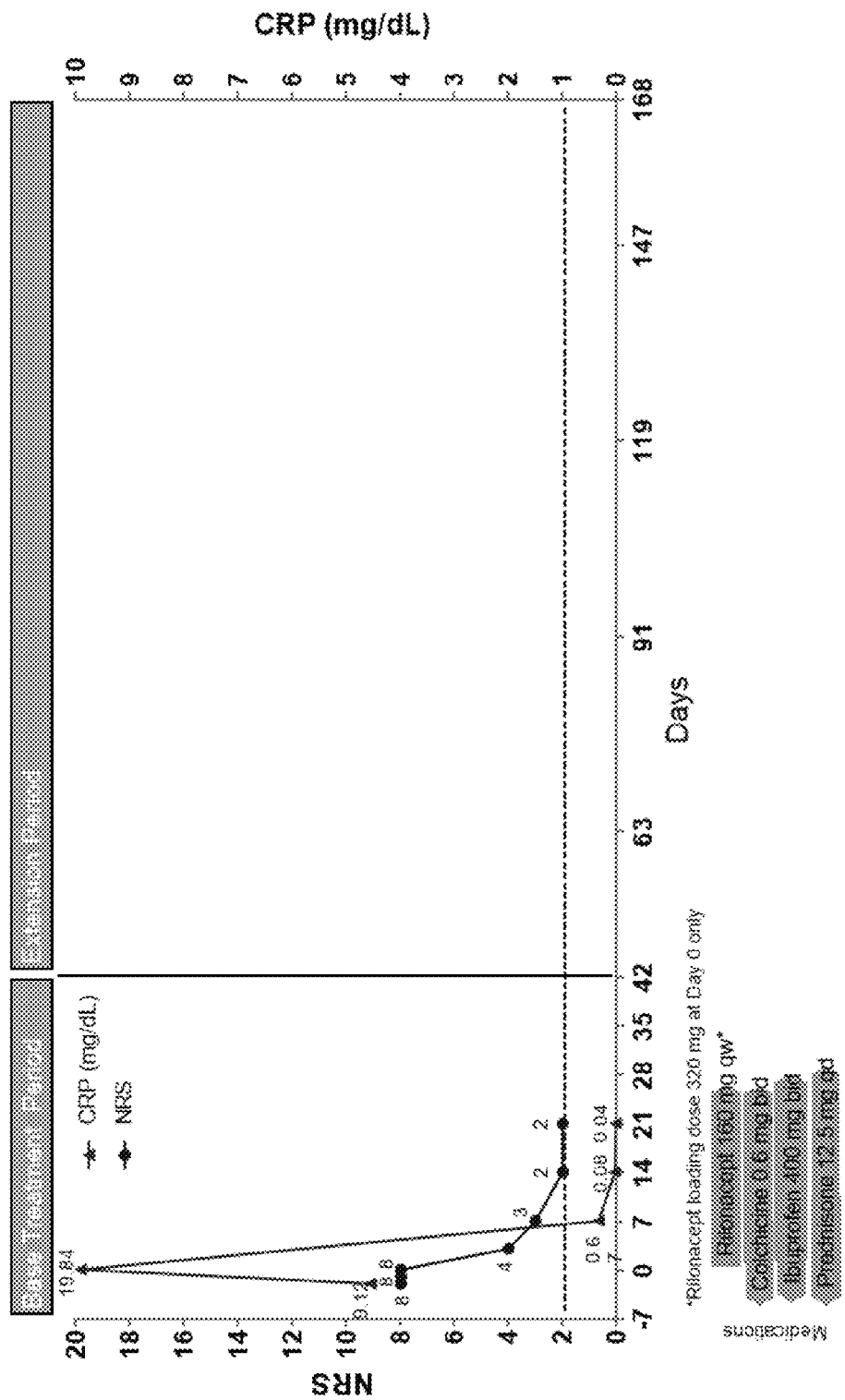
Figure 11:
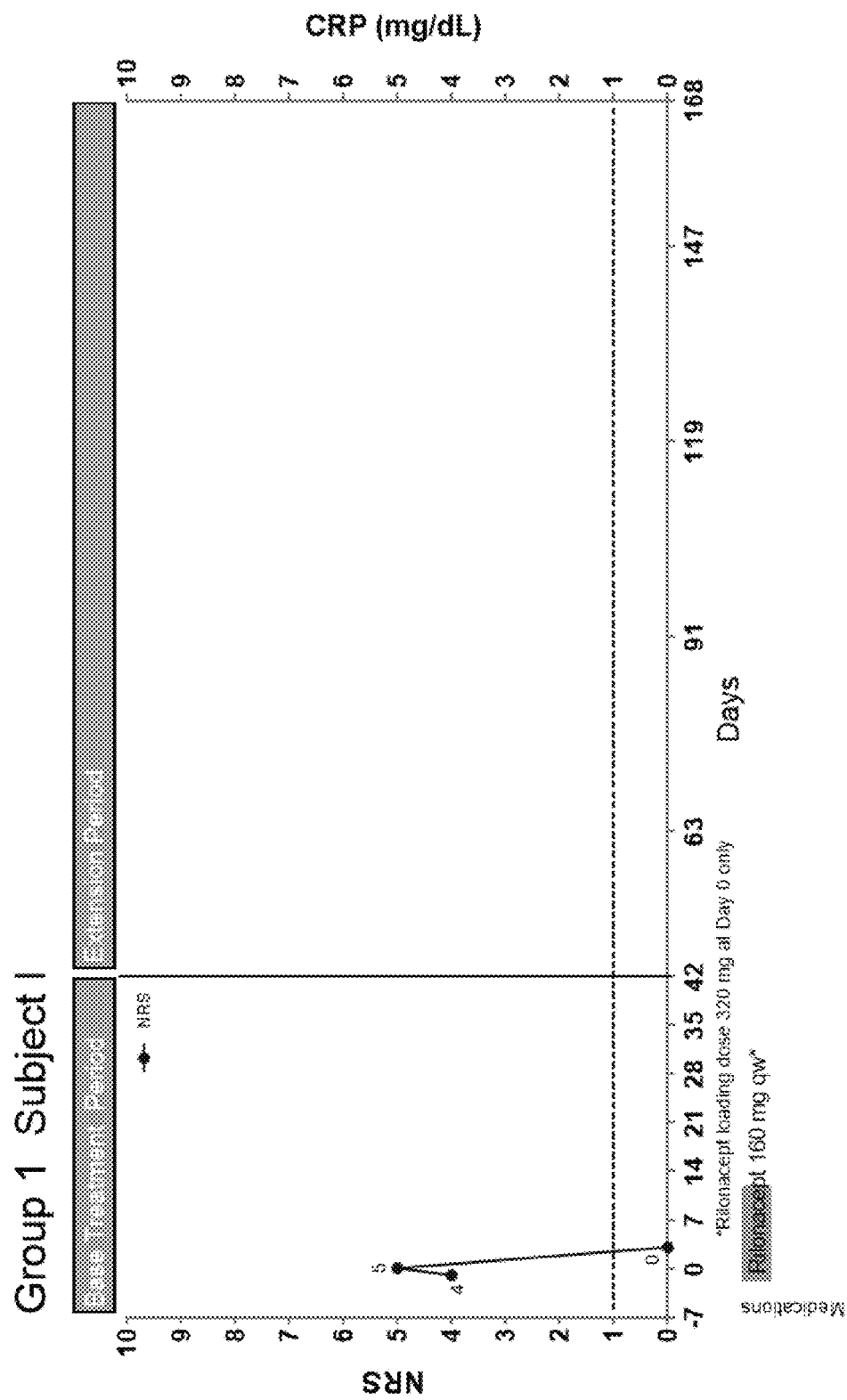

Specifically, fourteen patients (subjects) having pericarditis were treated with a 320 mg loading dose of subcutaneously injected interleukin-1 receptor-Fc fusion protein (rilonacept) at day 0, followed by 160 mg maintenance dose of subcutaneously injected rilonacept once a week. CRP levels and pain scores (using an 11-point Numerical Rating Scale (NRS)) for these patients are shown in FIGS. 1A-3C. Nine patients were enrolled in Group 1 (symptomatic idiopathic recurrent pericarditis subjects with elevated CRP), and six patients showed a reduction in CRP and NRS (pain) values even after a single dose of the treatment as shown in FIGS. 1A-C, E, and H-I. In the case of Subject D, the CRP level was not tested one week after the initial dose of rilonacept; however, at the second week of treatment, the CRP value showed a marked reduction compared to baseline (FIG. 1D). Subject F and G showed reduction in CRP levels as shown in FIGS. 1F and 1G. Each patient was being treated with prior medications for pain and/or inflammation at the indicated doses shown in FIGS. 1A-I. All Group 1 patients showed a trend towards a persistent reduction in pain and CRP values during subsequent dosing periods compared to baseline as shown in FIGS. 1A-I. As shown in FIG. 1C, after 6 weeks of rilonacept therapy, Subject C in Group 1 stopped taking ibuprofen and after approximately 8 weeks (55 days) of being treated with rilonacept this subject began a six week taper of prednisone. The subject's dose was reduced by 2.5 mg every other week. The subject has remained asymptomatic in the absence of ibuprofen and during the steroid weaning period, while continuing rilonacept therapy during the extension period. As shown in FIG. 1C, the subject proceeded through the next 77 days with neither ibuprofen nor prednisone, exhibiting no flare or recurrence, CRP level <0.5 mg/dl, and no pain.

Figure 2A:
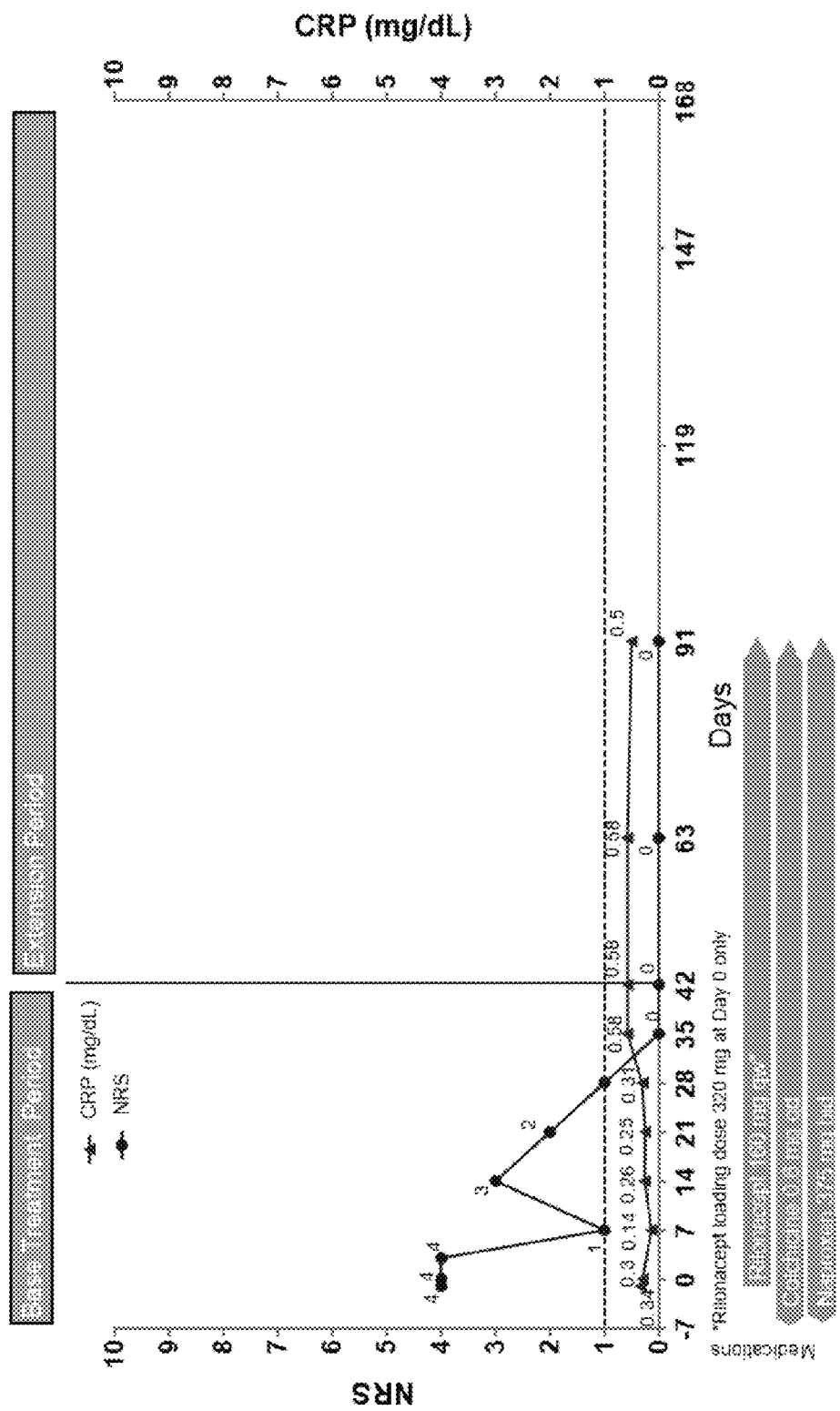
FIG. 2A-B depicts serum CRP levels and pain in NRS units in a Subject A and Subject B respectively after being administered 320 mg loading dose of interleukin-1 receptor-Fc fusion protein at day 0, followed by 160 mg once a week. X-axis shows days after treatment. Subject A and Subject B in this figure was enrolled under Group 2. The respective concurrent treatments and duration are designated graphically below the X-axis.
Figure 2B:
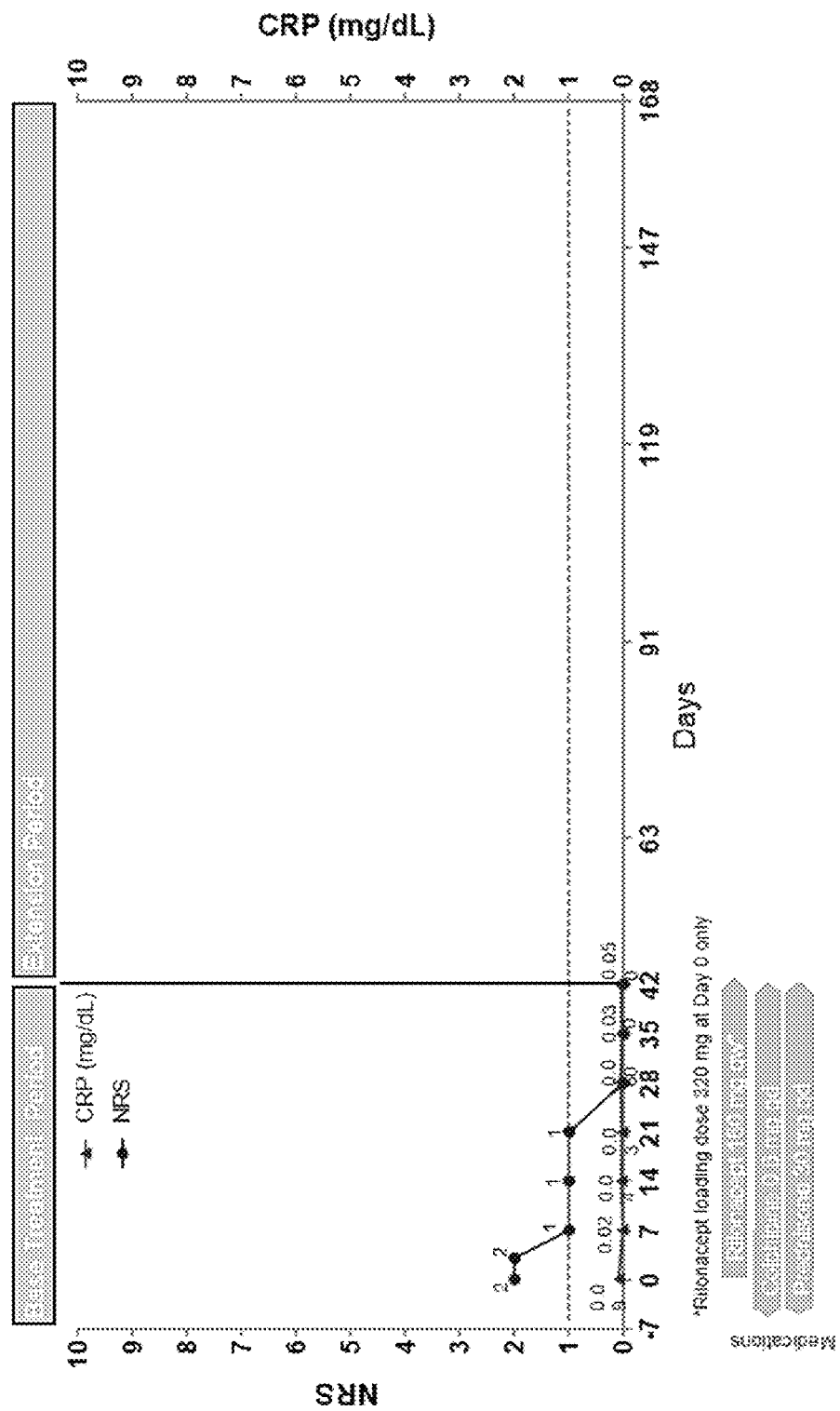
Figure 3A:
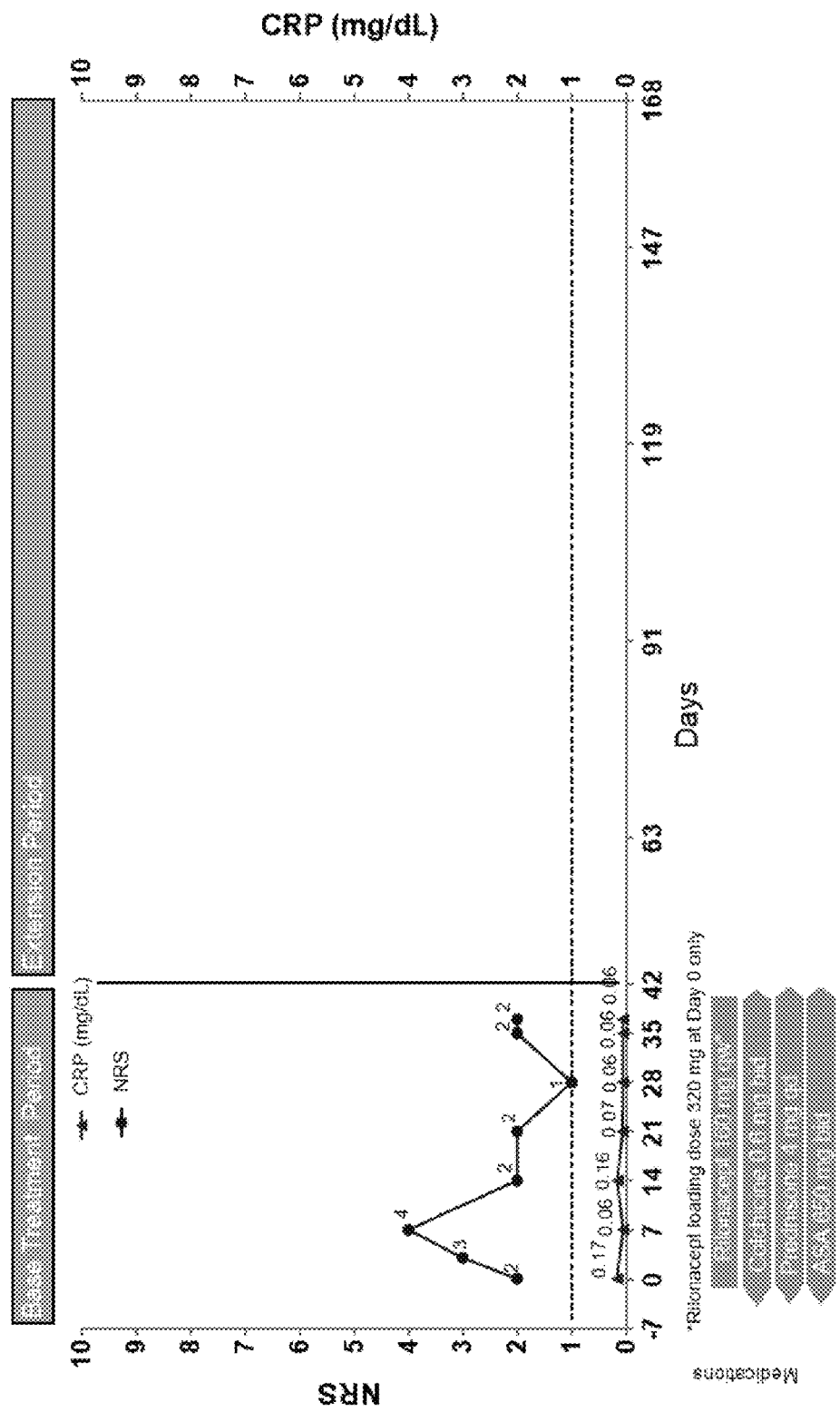
FIG. 3A-C depicts serum CRP levels and pain in NRS units in Subjects A-C after being administered 320 mg loading dose of interleukin-1 receptor-Fc fusion protein at day 0, followed by 160 mg once a week. X-axis shows days after treatment. Subjects A-C in this figure were enrolled under Group 3. The respective concurrent treatments and duration are designated graphically below the X-axis.
Figure 3B:
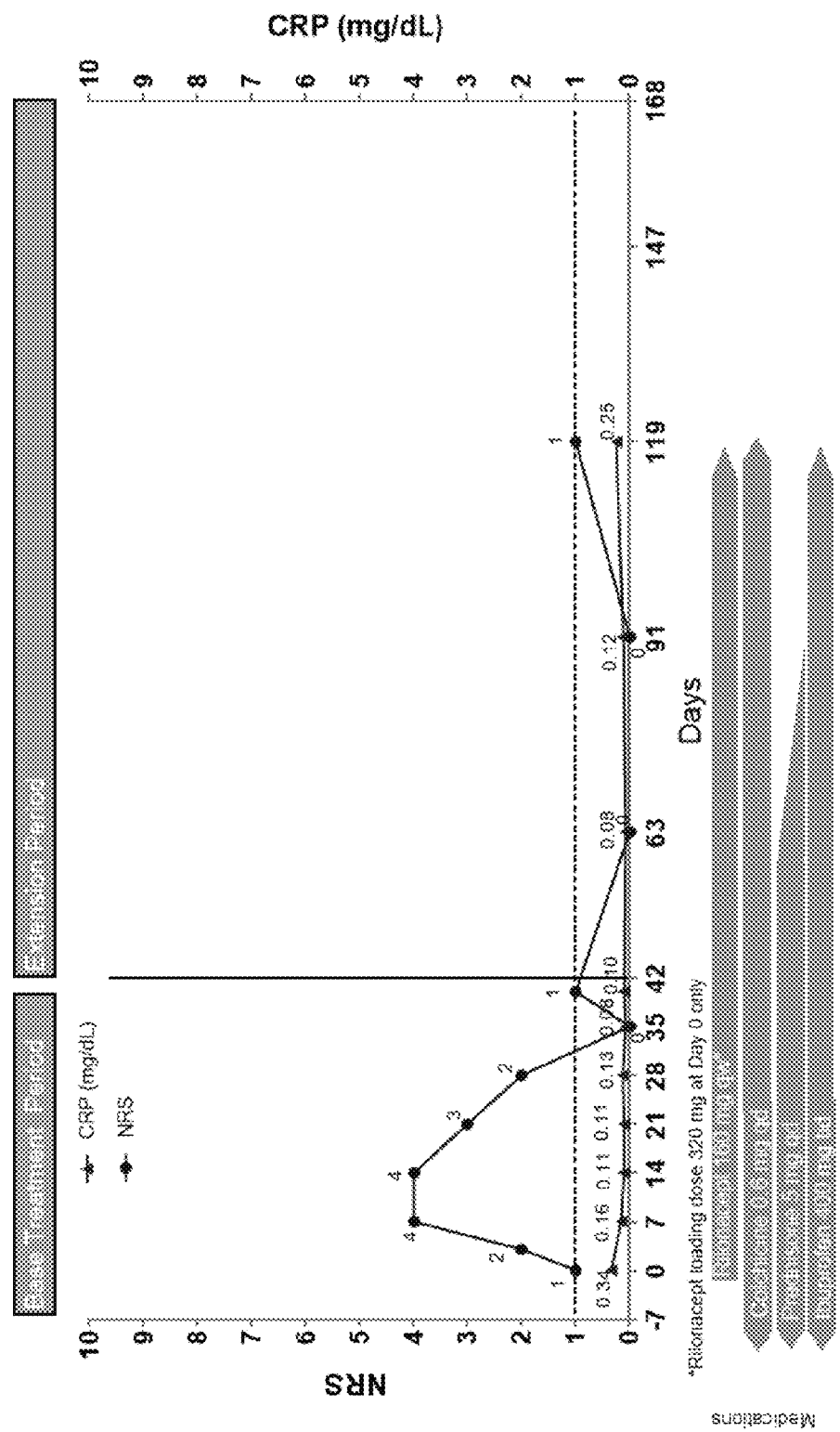
Figure 3C:
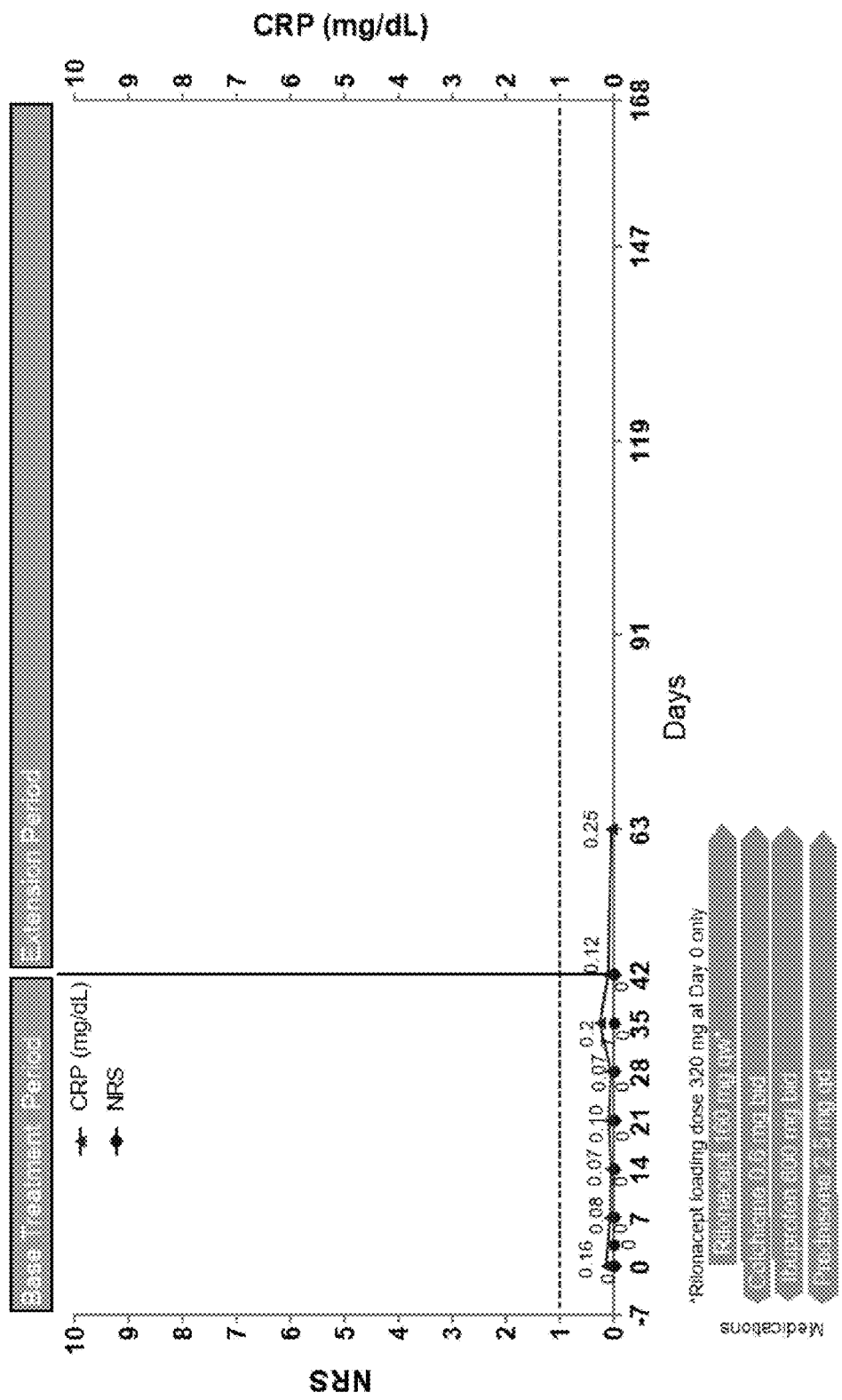

Two patients were enrolled in Group 2 (symptomatic RIP subjects with CRP<1 mg/dL and with pericardial inflammation present on cardiac MiII) and showed a reduction in CRP and pain even after a single dose of the treatment, and continued to show a trend towards a reduction in pain and CRP values during the subsequent dosing period compared to baseline as shown in FIGS. 2A and 2B. These patients were being treated with prior medications for pain and inflammation at the indicated doses shown in the figures. Three patients were enrolled in Group 3 (subjects with corticosteroid-dependent RIP not experiencing symptoms which would meet the diagnostic criteria for a flare of pericarditis), but were judged by the investigator as corticosteroid-dependent, i.e., based upon prior history and experience that the signs and symptoms of pericarditis would return if the corticosteroids were withdrawn. These patients were being treated with prior medications for pain and inflammation at the indicated doses shown in FIGS. 3A, 3B and 3C. After receiving rilonacept (320 mg) at day 0 and prior to withdrawal of concurrent therapies, the patient remained asymptomatic as observed on day 7. During the extension period of the study, the protocol allows the subjects enrolled in Group 3 to be weaned from concomitant pericarditis medications, including steroids, while remaining on rilonacept at the discretion of the medical practitioner. For example, FIG. 3B shows that the patient exhibited reduced CRP level and NRS score even at the tapering of prednisone dose to complete weaning at 91 days after the first dose of rilonacept. Subject B continued to show the reduced CRP level and NRS score over the next 28 days of prednisone-free regime, as shown in FIG. 3B. Subject A of Group 3 opted out of the extension study at completion of the base treatment period. Additional outcome measures, such as presence of effusion, QoL and ECG changes, acquired from subjects in Groups 1-3 are reported in FIG. 5. Adverse events reports for these subjects are shown in Table 2.

Twelve subjects treated with rilonacept have reported some mild adverse events (AEs) (Table 2). None were serious, and none led to discontinuation of study drug. The most commonly reported AEs were injection-site reactions, and all were mild and transient in nature. These results demonstrate that interleukin-1 receptor-Fc fusion protein is safe and efficacious for human treatment.

TABLE 2

| Subject ID | Reported Term for Adverse Event | Severity | Serious | Relationship to Study Drug | Action Taken on Study Drug | Outcome of Adverse Event |
|---|---|---|---|---|---|---|
| Group 1 Subject B | ISR Redness | Mild | No | Possibly Related | None | Recovered/ Resolved |
| Group 1 Subject B | ISR Warmness | Mild | No | Possibly Related | None | Recovered/ Resolved |
| Group 1 Subject E | Headache | Mild | No | Not Related | None | Recovered/ Resolved |
| Group 1 Subject E | Vertigo | Mild | No | Possibly Related | None | Recovered/ Resolved |

TABLE 2-continued

| Subject ID | Reported Term for Adverse Event | Severity | Serious | Relationship to Study Drug | Action Taken on Study Drug | Outcome of Adverse Event |
|---|---|---|---|---|---|---|
| Group 1 Subject E | Toothache | Mild | No | Not Related | None | Recovered/ Resolved |
| Group 1 Subject F | RT Dry Eye | Mild | No | Not Related | None | Not Recovered/ Not Resolved |
| Group 1 Subject D | Application site redness | Mild | No | Not Related | None | Recovered/ Resolved |
| Group 1 Subject D | Application site bruise | Mild | No | Not Related | None | Recovered/ Resolved |
| Group 1 Subject A | Heartburn | Mild | No | Unlikely Related | None | Recovered/ Resolved |
| Group 1 Subject A | Common cold | Mild | No | Unlikely Related | None | Recovered/ Resolved |
| Group 1 Subject A | Injection site reaction | Mild | No | Related | None | Recovered/ Resolved |
| Group 1 Subject A | Worsening of elevated LFTs** | Mild | No | Possibly Related | None | Recovered/ Resolved |
| Group 1 Subject A | Elevated HDL | Mild | No | Related | None | Not Recovered/ Not Resolved |
| Group 1 Subject A | Elevated CK | Mild | No | Unlikely Related | None | Recovered/ Resolved |
| Group 1 Subject A | Intermittent chest discomfort | Mild | No | Possibly Related | None | Not Recovered/ Resolved |
| Group 3 Subject A | Soreness at injection site | Mild | No | Related | None | Recovered/ Resolved |
| Group 3 Subject A | Pain with inspiration | Mild | No | Not Related | None | Recovered/ Resolved |
| Group 3 Subject A | Dry cough | Mild | No | Unlikely Related | None | Recovered/ Resolved |
| Group 3 Subject A | Hand muscle pain | Mild | No | Unlikely Related | None | Recovered/ Resolved |
| Group 3 Subject A | Worsening shortness of breath when lying flat | Mild | No | Possibly Related | None | Not Recovered/ Not Resolved |
| Group 3 Subject A | Worsening of elevated liver enzymes* | Mild | No | Not Related | None | Not Recovered/ Not Resolved |
| Group 3 Subject B | Shortness of breath | Mild | No | Possibly Related | None | Not Recovered/ Not Resolved |
| Group 3 Subject B | Fatigue | Mild | No | Unlikely Related | None | Not Recovered/ Not Resolved |
| Group 3 Subject B | Worsening pericarditis symptoms | Mild | No | Possibly Related | None | Recovered/ Resolved |
| Group 3 Subject B | Injection site reaction | Mild | No | Related | None | Recovered/ Resolved |
| Group 3 Subject B | Elevated cholesterol | Mild | No | Related | None | Not Recovered/ Not Resolved |
| Group 3 Subject B | Bilateral shoulder pain | Mild | No | Unlikely Related | None | Not Recovered/ Not Resolved |
| Group 3 Subject C | Injection site reaction | Mild | No | Related | None | Recovered/ Resolved |
| Group 1 Subject C | Pain at injection site | Mild | No | Related | None | Recovered/ Resolved |

TABLE 2-continued

| Subject ID | Reported Term for Adverse Event | Severity | Serious | Relationship to Study Drug | Action Taken on Study Drug | Outcome of Adverse Event |
|---|---|---|---|---|---|---|
| Group 1 Subject C | Intermittent muscle twitching - bilateral thighs | Mild | No | Possibly Related | None | Recovered/Resolved |
| Group 1 Subject C | Hemorrhoids | Mild | No | Not Related | None | Recovered/Resolved |
| Group 1 Subject C | Nausea | Mild | No | Not Related | None | Recovered/Resolved |
| Group 1 Subject C | Cold | Mild | No | Possibly Related | None | Recovered/Resolved |
| Group 2 Subject A | Redness at injection site | Mild | No | Related | None | Recovered/Resolved |
| Group 1 Subject G | Atypical Chest Pain | Moderate | Yes | Unlikely Related | None | Recovered/Resolved |
| Group 1 Subject G | Bruising at injection site | Mild | No | Related | None | Recovered/Resolved |
| Group 1 Subject G | Right lower extremity cellulitis | Mild | No | Unlikely Related | None | Recovered/Resolved |
| Group 1 Subject G | Chest pain | Mild | No | Not Related | None | Recovered/Resolved |
| Group 1 Subject H | Diarrhea | Mild | No | Unlikely Related | None | Recovered/Resolved |

Example 3. Long Term Efficacy of Interleukin-1 Receptor-Fc Fusion Protein in Subjects with Recurrent Pericarditis A Phase III, double blind, placebo controlled, randomized withdrawal study with open label extension, is designed to assess the efficacy and safety of rilonacept treatment in subjects with recurrent pericarditis. The primary endpoint is time to pericarditis recurrence, defined as the time from randomization to the date of the first pericarditis recurrence for each subject. Only CEC-confirmed pericarditis recurrence will be considered as an event for the primary analysis. Primary analysis of this study is at the last ($22^{nd}$) CEC-confirmed pericarditis recurrence and all subjects in the RW period have been treated for 24 weeks. Subjects who have not had an adjudicated pericarditis recurrence will be censored on the day of the last available assessment before data cutoff.

Figure 4:
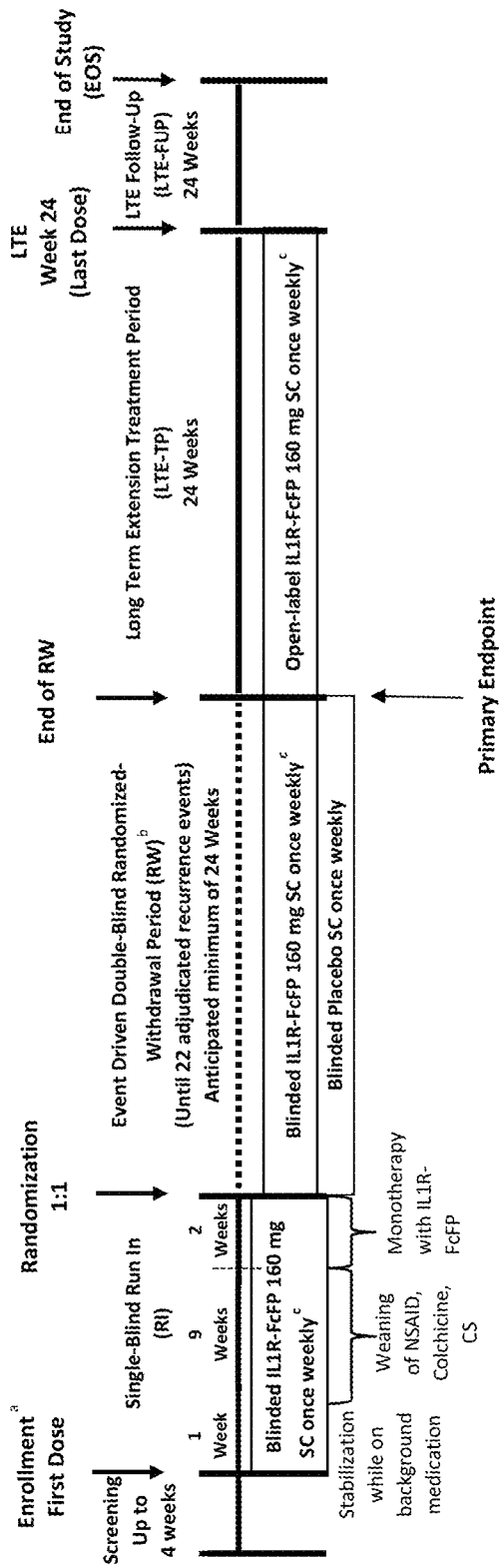
FIG. 4 depicts a graphic representation of the study protocol for long term efficacy of interleukin-1 receptor-Fc fusion protein in subjects with recurrent pericarditis. CS=corticosteroid; EOS=end of study, LTE=Long Term Extension; NSAID=nonsteroidal anti-inflammatory drug; RI=run in, RW=randomized withdrawal, SC=subcutaneously, TP=treatment period. a. The first dose given is a loading dose of IL1R-FcFP. In adult subjects ≥18 years old, 320 mg is given as 2 SC doses of 160 mg. In paediatric subjects ≥12 and <18 years old, 4.4 mg/kg is given as 2 SC doses of 2.2 mg/kg. After the loading dose, IL1R-FcFP will be administered as a 160 mg (adults) or 2.2 mg/kg (paediatric subjects) SC dose once weekly. b. Subject's treatment duration will depend on when the subject is enrolled relative to the end of RW. c. The adult dose is 160 mg SC once weekly. The paediatric dose is 2.2 mg/kg SC once weekly. Note: Figure is not drawn to scale.

All suspected pericarditis recurrence events are formally adjudicated by the Clinical Endpoint Committee (CEC), and only events that are confirmed by the CEC as pericarditis recurrences are used in the Primary Endpoint analysis. A multitude of other endpoints are analyzed at various stages of the study as described in the following sections. The overview of the study is depicted in FIG. 4.

Subjects eligible for the study are subjects with recurrent pericarditis who do not have pericarditis secondary to prohibited conditions. The study population includes both adult subjects ≥18 years old and pediatric subjects ≥12 and <18 years old with a history of at least 2 prior pericarditis episodes (including the first episode and 1 recurrence). Enrollment of pediatric subjects are limited to up to 20% of the study population. To be eligible for the study, subjects must present at screening with at least a third pericarditis episode, defined as at least 1 day with pericarditis pain measurement ≥4 on the 11-point Numerical Rating Scale (NRS) and C-reactive protein (CRP) level ≥1 mg/dL within 7 days prior to first study drug administration. Pericarditis pain ≥4 and CRP≥1 mg/dL are not required to be present on the same day.

Subjects included in the study may be receiving concomitant NSAIDs and/or colchicine and/or oral CS treatment in any combination, provided that the dosages of these medications have been stable (or not increased) for at least 3 days prior to first administration of study drug, and that changes in medications made within this time period (for instance, 1-time use of NSAIDs) are not anticipated by the investigator to significantly alter assessments of baseline disease activity.

The study has 5 periods:
(1) Screening period, during which assessment of disease characteristics, baseline therapy, and the pre-treatment workup is completed (up to 4 weeks)
(2) Single-blind Run-In (RI) period (12 weeks), during which blinded rilonacept (IL-1 receptor-Fc fusion protein, IL1RFcFP) is administered SC once weekly in all subjects. The RI period includes the following:
    1-week Stabilization period, during which blinded rilonacept is administered in addition to standard of care (SOC) pericarditis therapy and the ongoing pericarditis episode is treated.
    9-week Weaning period, during which subjects are weaned off background SOC pericarditis therapy, as applicable, while treatment with blinded rilonacept continues. The dosages of corticosteroids (CS), NSAIDs, and colchicine are tapered according to the weaning protocol in the Pharmacy Manual (for the purpose of the protocol, aspirin is considered an NSAID). In general, CS doses are tapered off starting at RI Week 1 and are withdrawn by RI Week 10 (over a total of 9 weeks). NSAID and colchicine doses are tapered off starting at RI Week 4 and are withdrawn by RI Week 10 (over a total of 6 weeks).

2-week Monotherapy period during which subjects who have successfully weaned off background SOC pericarditis therapy continue to receive blinded rilonacept.

In the single-blind RI period (subjects are blinded regarding the time of transition from the single-blind to the double-blind period), adult subjects ≥18 years old will receive rilonacept as an initial loading dose of 320 mg (2 SC injections of 160 mg each) at the RI baseline visit (2×2 ml), followed by a 160 mg (2 ml) SC dose once weekly throughout the RI period. Pediatric subjects (≥12 and <18 years old) receive an initial loading dose of rilonacept 4.4 mg/kg (2 SC injections of 2.2 mg/kg each) at the RI baseline visit (maximum 2×2 ml), and then 2.2 mg/kg (maximum 2 ml) SC once weekly throughout RI period. Subjects who stopped background pericarditis medications and who achieve Clinical Response at RI Week 12, defined as the weekly average of daily pericarditis pain score ≤2.0 on the 11-point NRS within the 7 days prior to and including the day of randomization on RI Week 12 and a CRP level ≤0.5 mg/dL at RI Week 12/RW baseline visit, proceed into the double-blind placebo-controlled Randomized-Withdrawal (RW) period. Subjects who do not achieve Clinical Response at RI Week 12 on rilonacept monotherapy are discontinued from study drug, transitioned to SOC pericarditis therapy at the investigator's discretion, and followed through the end of the RW period.

The following secondary endpoints are assessed in this period:

Proportion of subjects who achieved Clinical Response. Clinical Response is defined as a weekly average of daily pericarditis pain of ≤2.0 on the 11-point NRS during the week preceding randomization AND CRP level ≤0.5 mg/dL at RI Week 12/RW baseline visit.

Time to CRP normalization (≤0.5 mg/dL)

Number (percentage) of subjects with normalization of CRP at RI Week 12

Change from baseline in pericarditis pain at RI Week 12

Change from baseline in CRP level at RI Week 12

Resolution of ECHO and ECG abnormalities (yes/no) at RI Week 12

Percentage of days with no or minimal pain

Number (percentage) of subjects with absent or minimal pericarditis symptoms based on PGIPS Number (percentage) of subjects with absent or minimal pericarditis activity based on the PGA-PA Change over time in the SF-36 Physical Component Score Change over time in the SF-36 Mental Component Score Change in the EQ-5D-5L Change over time in the subject's sleep quality assessed with the ISI Change over time in ISI categories Number (percentage) of subjects who were off background pericarditis medication at RI Week 12.

(3) Double-blind placebo-controlled RW period (pericarditis recurrence event-driven duration, with a minimum of 24 weeks).

The primary efficacy endpoint, that is the time of pericarditis recurrence for each subject is determined at this stage. Only CEC-confirmed pericarditis recurrence is considered as an event for the primary analysis.

Major secondary efficacy endpoints for the RW period include:

Proportion of subjects who maintained Clinical Response at Week 24 of the RW period Percentage of days with no or minimal pain (pain ≤1 on the 11-point NRS) in the first 24 weeks of the RW period Proportion of subjects with absent or minimal pericarditis symptoms (based on the 7-point rating scale of PGIPS) at Week 24 of the RW period.

Other secondary endpoints for the RW period include:

Proportion of subjects without pericarditis recurrence in the first 24 weeks of the RW period Time to NRS≥4

Time to CRP level≥1 mg/dL

Time to pericardial rub

Time to widespread ST-segment elevation or PR-segment depression on ECG

Time to new or worsening pericardial effusion on ECHO

Change over time in CRP levels

Change over time in subject's assessments of pericarditis pain (weekly average)

Number (percentage) of subjects with absent or minimal pericarditis activity based on the PGA-PA Change over time in SF-36 Physical Component Score Change over time in SF-36 Mental Component Score Change in EQ-5D-5L Change over time in subject's sleep quality assessed with the ISI Change over time in ISI categories Number (percentage) of subjects who receive ORT therapy for pericarditis recurrence (analgesics, NSAIDs, and/or colchicine) in the RW period During this stage, subjects who were able to stop background pericarditis medication and who achieve Clinical Response at RI Week 12 are randomized in a double-blind manner at a 1:1 ratio to the following:

Rilonacept 160 mg (2.2 mg/kg in pediatric subjects) SC injections once weekly

Matching placebo SC injections once weekly

Subjects report pericarditis associated pain daily based on 11-point pericarditis pain NRS scoring. A sensitivity analysis is done based on the investigator's assessment of the event.

All statistical tests for the treatment comparison of efficacy endpoints in the RW period are based on the Intent-To-Treat (ITT) analysis set with 1-sided α=0.025.

Pericarditis Recurrence in the RW Period

Pericarditis recurrence is defined as the recurrence of typical pericarditis pain associated with supportive objective evidence of pericarditis. Upon pericarditis recurrence, subjects who report at least 1 day with pericarditis pain measurement ≥4 on the 11-point NRS and have 1 CRP value ≥1 mg/dL (either on the same day or separated by no more than 7 days) receive bailout rilonacept (2 open-label injections of 160 mg rilonacept [or 4.4 mg/kg for pediatric subjects] followed by once-weekly open-label rilonacept SC injections of 160 mg [or 2.2 mg/kg for pediatric subjects]), irrespective of randomized treatment assignment and as soon as at least 5 days have passed since the last study drug injection. Sequential Oral Rescue Therapy (ORT), i.e., analgesics first, then NSAIDs, and then colchicine, can be added if needed at the discretion of the investigator, as outlined in the protocol and Pharmacy Manual.

Subjects with pericarditis recurrence who do not meet the protocol criteria for bailout rilonacept continue with the blinded study drug until the protocol criteria for bailout rilonacept are met or through the end of the RW period. For those subjects, sequential ORT can be added to blinded study drug at the discretion of the investigator, as outlined in the protocol and Pharmacy Manual.

All suspected pericarditis recurrence events in the RW period are formally adjudicated by the Clinical Endpoint Committee (CEC), and only events that are confirmed by the CEC as pericarditis recurrences are used in the Primary Endpoint analysis.

A subject experiencing a suspected pericarditis recurrence is required to contact the study investigator immediately for evaluation. Required assessments include:

Evaluation of pericarditis pain on 11-point NRS.

Evaluation of concomitant medications as well as pericarditis concomitant medications.

Obtain laboratory samples for CRP (local and central) (the POC device provided by Kiniksa Pharmaceuticals is the preferred method for local laboratory CRP assessment).

Acquisition of a 12-lead ECG.

Acquisition of a cardiac ECHO per core laboratory imaging parameters; this ECHO can be read locally for the purpose of pericarditis recurrence assessment and then requires submission to the ECHO core laboratory for central review.

Performing an abbreviated physical examination, height and body weight.

Having subjects ≥18 years complete the SF-36, EQ-5D-5L, ISI

Having subjects complete the PGIPS score.

The investigator completes the PGA-PA.

Obtaining central laboratory samples for PK, ADAs, and biomarkers.

Other procedures deemed necessary per the investigator or delegated site personnel.

Upon the complete evaluation, if the investigator deems the subject to be having a pericarditis recurrence event, he/she should contact the PPD medical monitor to confirm that all assessments have been performed and collected.

(4) Long Term Extension Treatment Period (LTE-TP) (24 weeks), during which all subjects completing the RW period (including subjects transitioned to open-label rilonacept upon pericarditis recurrence) have an option to receive up to 24 weeks of open-label rilonacept 160 mg (or 2.2 mg/kg for pediatric subjects) SC injections once weekly based on their clinical status and at the discretion of the investigator, after signing LTE informed consent. Any subject who, in the opinion of investigator, should not continue open-label rilonacept are offered participation in the LTE off study drug and after signing LTE informed consent.

The endpoints assessed in this phase are listed below. Each endpoint is summarized through Week 24, by subjects who do and do not have an adjudicated pericarditis recurrence in the RW period, respectively, and overall:

Number (percentage) of subjects with pericarditis recurrences

Proportion of subjects with Clinical Response

Change over time in CRP levels

Change over time in the subject's assessments of pericarditis pain

Percentage of days with no or minimal pain

PGIPS

PGA-PA

Change over time in the SF-36 Physical Component Score

Change over time in the SF-36 Mental Component Score

Change in the EQ-5D-5L

Change over time in the subject's sleep quality assessed with the ISI

Change over time in ISI categories

Number (percentage) of subjects requiring addition of SOC pericarditis therapy.

(5) Long Term Extension Follow-up Period (LTE-FUP) (24 weeks), during which all subjects in the LTE-TP are followed in the LTE-FUP for safety and potential pericarditis recurrences.

Efficacy and Safety Assessments

Efficacy assessments include the following: daily pericarditis pain on the 11 point NRS in the subject's electronic diary, CRP level, electrocardiogram (ECG), echocardiography (ECHO), patient Global Impression of Pericarditis Severity (PGIPS), physician Global Assessment of Pericarditis Activity (PGA-PA), 36 Item Short Form Health Survey (SF 36), 5-Level EuroQoL-5D (EQ 5D 5L), insomnia Severity Index (ISI), cardiac magnetic resonance imaging (in a substudy in approximately 10 subjects).

Pharmacokinetic or pharmacodynamic assessments include: PK analysis, anti-rilonacept antibodies, biomarkers, and/or peripheral blood mononuclear cell isolation (for subjects who sign the separate informed consent for pharmacogenomics assessments)

Safety assessments during the study will include: physical examination, vital signs measurements, adverse event (AE) monitoring, chest x ray, tuberculosis screening.

In order to control the overall 1 sided type I error rate at the 0.025 level, a gatekeeping procedure in combination with Hochberg's procedure will be applied to testing the primary and major efficacy secondary endpoints.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating recurrent pericarditis comprising administering subcutaneously to a patient in need of treatment, an interleukin-1 receptor-Fc fusion protein at 160 mg,
wherein the interleukin-1 receptor-Fc fusion protein comprises an extracellular domain of IL-1R1, and an extracellular domain of IL-1R accessory protein (IL-1RAcP),
wherein the extracellular domain of IL-1R1 comprises an amino acid sequence with at least 99% identity to SEQ ID NO: 4; and
wherein the extracellular domain of IL-1RAcP comprises an amino acid sequence with at least 99% identity to SEQ ID NO: 3.

2. The method of claim 1, wherein the extracellular domain of IL-1R1 comprises an amino acid sequence set forth in SEQ ID NO: 4.

3. The method of claim 1, wherein the extracellular domain of IL-1RAcP comprises an amino acid sequence set forth in SEQ ID NO: 3.

4. The method of claim 1, wherein the interleukin-1 receptor-Fc fusion protein comprises an Fc portion of IgG1.

5. The method of claim 1, wherein the interleukin-1 receptor-Fc fusion protein administered once every week.

6. The method of claim 5, wherein the interleukin-1 receptor-Fc fusion protein is administered for one or more weeks.

7. The method of claim 1, wherein the interleukin-1 receptor-Fc fusion protein is a homodimer.

8. The method of claim 1, wherein the patient in need of treatment has a recurrence of pericarditis with pericarditis pain measurement ≥4 Numerical Rating Scale (NRS) and C-reactive protein (CRP) level ≥1 mg/dL.

9. The method of claim 1, wherein the administration of the interleukin-1 receptor-Fc fusion protein results in a treatment response defined by pericardial pain NRS ≤2 and CRP ≤0.5 mg/dL.

10. The method of claim 9, wherein the NRS score is reduced to 2 or less within 7 days from the first administration of the interleukin-1 receptor-Fc fusion protein.

11. The method of claim 9, wherein CRP level is reduced to <0.5 mg/dL within 7 days from the first administration of the interleukin-1 receptor-Fc fusion protein.

12. The method of claim 1, wherein the administration of the interleukin-1 receptor-Fc fusion protein results in a withdrawal of concurrent therapy or standard of care treatment in the patient.

13. The method of claim 12, wherein the concurrent therapy or standard of care treatment is NSAIDs, steroid, colchicine, corticosteroid, or combinations thereof.

14. The method of claim 13, wherein the administration of the interleukin-1 receptor-Fc fusion protein results in withdrawal of corticosteroid treatment in the patient.

15. The method of claim 14, wherein the withdrawal of the corticosteroid treatment in the patient is at about 4 weeks, 5 weeks, 6 weeks, 7 weeks, 8 weeks or 9 weeks after the first administration.

16. The method of claim 1, wherein the administration of the interleukin-1 receptor-Fc fusion protein results in reduced risk of pericarditis recurrence of less than 5%.

* * * * *